(12) United States Patent
De Taboada et al.

(10) Patent No.: US 10,695,579 B2
(45) Date of Patent: Jun. 30, 2020

(54) APPARATUS AND METHOD FOR INDICATING TREATMENT SITE LOCATIONS FOR PHOTOTHERAPY TO THE BRAIN

(75) Inventors: Luis De Taboada, Carlsbad, CA (US); Jackson Streeter, Reno, NV (US)

(73) Assignee: Pthera LLC

( * ) Notice: Subject to any disclaimer, the term of this patent is extended or adjusted under 35 U.S.C. 154(b) by 1008 days.

(21) Appl. No.: 12/703,653

(22) Filed: Feb. 10, 2010

(65) Prior Publication Data
US 2010/0204762 A1    Aug. 12, 2010

Related U.S. Application Data

(63) Continuation-in-part of application No. 12/403,824, filed on Mar. 13, 2009, now abandoned, which is a
(Continued)

(51) Int. Cl.
*A61N 5/06* (2006.01)
*A61N 5/067* (2006.01)

(52) U.S. Cl.
CPC ...... *A61N 5/0613* (2013.01); *A61N 2005/063* (2013.01); *A61N 2005/067* (2013.01);
(Continued)

(58) Field of Classification Search
CPC ...... A61N 5/06; A61N 5/0613; A61N 5/0618; A61N 5/0622; A61N 2005/0626;
(Continued)

(56) References Cited

U.S. PATENT DOCUMENTS 5,617,258 A    4/1997  Negus et al.
6,214,035 B1   4/2001  Streeter
(Continued)

FOREIGN PATENT DOCUMENTS

EP    2 082 696     7/2009
WO    WO 00/25684   5/2000
(Continued)

OTHER PUBLICATIONS

EPO Extended Search Report re EP Application No. 09170679.6, dated Jan. 4, 2010. in 6 pages.
[No Author Listed]"Optical Absorption Spectra of Melanins—a Comparison of Theoretical and Experimental Results," Acelerys, p. 1-5.
Belevich et al., "Exploring the proton pump mechanism of cytochrome c oxidase in real time," Proc.Nat'l Acad. Sci, 2007, vol. 104, pp. 2685-2690.
(Continued)

*Primary Examiner* — Ahmed M Farah
(74) *Attorney, Agent, or Firm* — Fish & Richardson P.C.

(57) ABSTRACT

An apparatus and method for indicating treatment site locations for phototherapy to the brain are disclosed. In some embodiments, the apparatus is a headpiece wearable by a patient. The headpiece includes a body adapted to be worn over at least a portion of the patient's scalp and a plurality of position indicators corresponding to a plurality of treatment site locations at the patient's scalp where a light source is to be sequentially positioned such that light from the light source is sequentially applied to irradiate at least a portion of the patient's brain. At least one of the position indicators includes an optically transmissive portion having an area of at least 1 cm² through which the light propagates.

34 Claims, 46 Drawing Sheets

Related U.S. Application Data continuation-in-part of application No. 12/389,294, filed on Feb. 19, 2009, now Pat. No. 10,357,662, which is a continuation-in-part of application No. 11/385,980, filed on Mar. 21, 2006, now abandoned.

(60) Provisional application No. 61/037,668, filed on Mar. 18, 2008, provisional application No. 60/763,261, filed on Jan. 30, 2006.

(52) U.S. Cl.
CPC ............... *A61N 2005/0629* (2013.01); *A61N 2005/0647* (2013.01)

(58) Field of Classification Search
CPC .... A61N 2005/0627; A61N 2005/0628; A61N 2005/0629; A61N 2005/0635; A61N 2005/0643; A61N 2005/0647; A61N 2005/065; A61N 2005/0651; A61N 2005/062; A61N 2005/0658; A61N 2005/0659; A61N 2005/0662; A61N 2005/067
USPC ........................... 607/88–91; 606/9; 128/898
See application file for complete search history.

(56) References Cited

U.S. PATENT DOCUMENTS

| | | | |
|---|---|---|---|
| 6,267,780 | B1 | 7/2001 | Streeter |
| 6,273,905 | B1 | 8/2001 | Streeter |
| 6,290,714 | B1 | 9/2001 | Streeter |
| 6,537,304 | B1 | 3/2003 | Oron |
| 6,918,922 | B2 | 7/2005 | Oron |
| 7,303,578 | B2 * | 12/2007 | De Taboada ......... A61N 5/0613 128/898 |
| 7,575,589 | B2 * | 8/2009 | De Taboada ......... A61N 5/0613 607/88 |
| 2003/0216797 | A1 * | 11/2003 | Oron ............................... 607/89 |
| 2004/0030325 | A1 | 2/2004 | Cahir et al. |
| 2004/0138727 | A1 * | 7/2004 | Taboada ............... A61N 5/0613 607/88 |
| 2005/0107851 | A1 | 5/2005 | Taboda |
| 2005/0143792 | A1 * | 6/2005 | Jay ................................. 607/88 |
| 2007/0159592 | A1 * | 7/2007 | Rylander et al. ............... 351/44 |
| 2007/0179570 | A1 | 8/2007 | Taboda |
| 2007/0179571 | A1 | 8/2007 | Taboda |
| 2008/0287930 | A1 * | 11/2008 | Rapoport ......................... 606/9 |
| 2009/0254154 | A1 | 10/2009 | Taboda |

FOREIGN PATENT DOCUMENTS

| | | |
|---|---|---|
| WO | WO 06/115761 | 11/2006 |
| WO | WO 08/049905 | 5/2008 |

OTHER PUBLICATIONS

Belevich et al., "Proton-coupled electron transfer drives the proton pump of cytochrome c oxidase," Nature, 2006, vol. 440, pp. 829-832.
Breugel and Bar in "Power Density and Exposure Time of He—Ne Laser Irradiation Are More Important Than Total Energy Dose in Photo-Biomodulation of Human Fibroblasts In Vitro," Lasers in Surgery and Medicine, vol. 12, pp. 528-537 (1992).
U.S. Appl. No. 12/233,498, filed Sep. 18, 2008, Delapp et al.
Burton et al., "Relation Between Blood Pressure and Flow in the Human Forearm," J. Appl. Physiology, 1951, vol. 4, No. 5, pp. 329-339.
Catanzaro et al., "Managing Tissue Heating in Laser Therapy to Enable Double-Blind Clinical Study," Mechanisms for Low-Light Therapy, Proc. of the SPIE, vol. 6140, 2006, pp. 199-208.
Hamblin et al., "Mechanisms of Low Level Light Therapy.," Proc. of SPIE, 2006, vol. 6140, 614001.
Janssen et al., "Modeling of temperature and perfusion during scalp cooling," Phys. Med. Biol, 2005, vol. 50, pp. 4065-4073.
Karu et al., "Cell Attachment to Extracellular Matrices is Modulated by Pulsed Radiation at 820 nm and Chemicals that Modify the Activity of Enzymes in the Plasma Membrane," Lasers in Surgery and Medicine, 2001, vol. 29, pp. 274-281.
Lampl et al., "Infrared laser therapy for ischemic stroke: a new treatment strategy: Results of the NeuroThera Effectiveness and Safety Trial-I (NEST-I)," Stroke, 2007, 38:1843-1849.
Lapchack & Taboda, "Transcranial near infrared laser treatment (NILT) increases cortical adenosine-5'triphosphate (ATP) content following embolic strokes in rabbits," Brain Research, vol. 1306, pp. 100-105.
Lepselter et al., "Biological and clinical aspects in laser hair removal," J. Dermatological Treatment, 2004, vol. 15, pp. 72-83.
Lisman et al., "Two Light-Induced Processes in the Photoreceptor Cells of Limulus Ventral Eye," J. Gen. Physiology, 1971, vol. 58, pp. 544-561.
Lubart & Karu., "Mechanisms of Low-Power Laser Light Action on Cellular Level, Effects of Low-Power Light on Biological Systems V," Proc. SPIE vol. 4159, 2000, pp. 1-17.
Matas et al., "Eliminating the Issue of Skin Color in Assessment of the Blanch Response," Adv. in Skin & Wound Care, 2001, vol. 14 (4, part 1 of 2), pp. 180-188.
Niitsuma et al., "Experimental study of decubitus ulcer formation in the rabbit ear lobe," J. of Rehab. Res. and Dev, Jan./Feb. 2003, vol. 40, No. 1, pp. 67-72.
Oron et al., "Low-Level Laser Therapy Applied Transcranially to Mice following Traumatic Brain Injury Significantly Reduces Long-Term Neurological Deficits," Journal of Neurotrauma, 2007, vol. 24, No. 4, pp. 651-656.
Wells et al., "Biophysical mechanisms responsible for pulsed low-level laser excitation of neural tissue," Proc. SPIE, Optical Interactions with Tissue and Cells XVII, vol. 6084, Mar. 1, 2006, 60840X.
Zivin et al, "Effectiveness and safety of transcranial laser therapy for acute ischemic stroke," Stroke, 2009, 40:1359-1364.

* cited by examiner

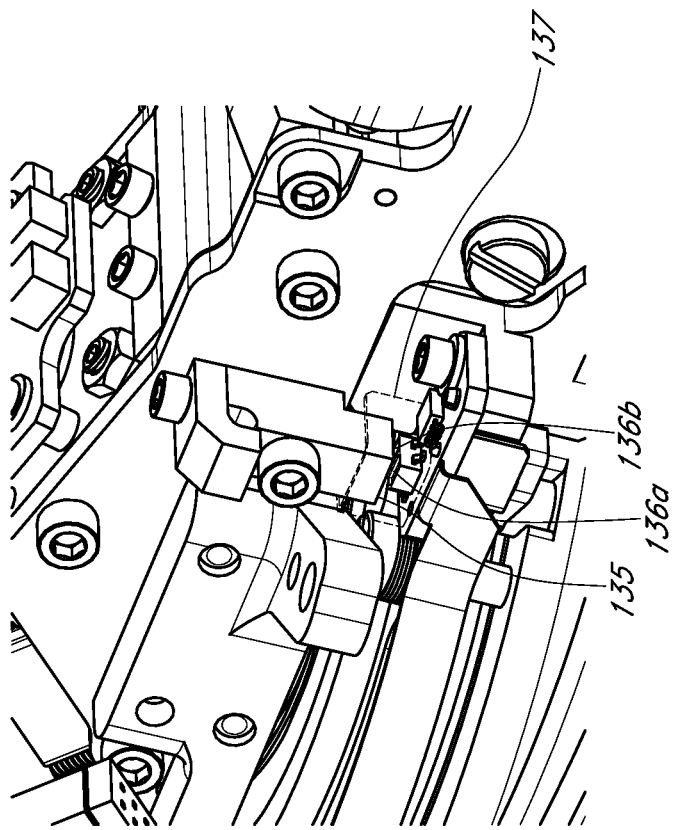
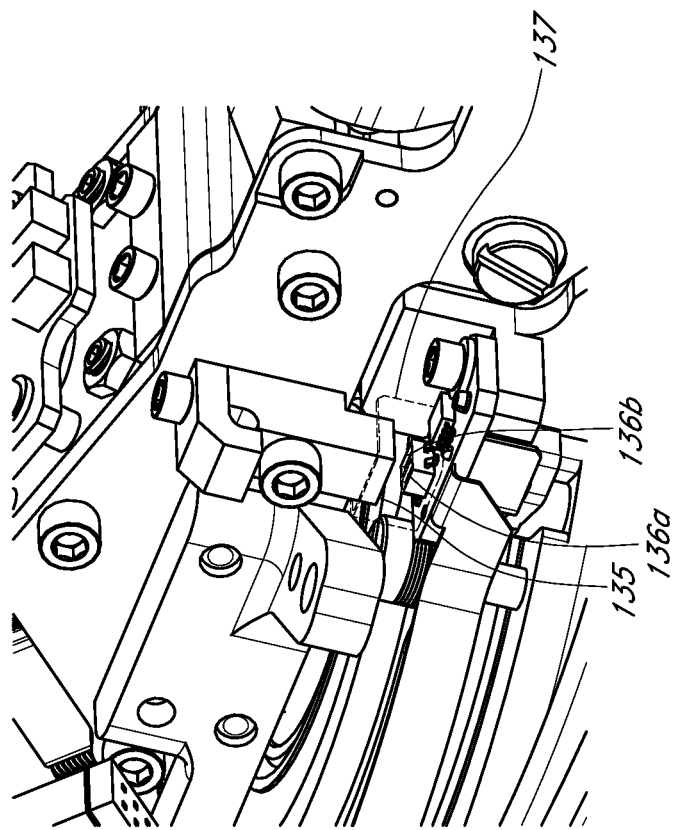

APPARATUS AND METHOD FOR INDICATING TREATMENT SITE LOCATIONS FOR PHOTOTHERAPY TO THE BRAIN

CLAIM OF PRIORITY

This application is a continuation-in-part application of U.S. patent application Ser. No. 11/385,980, filed Mar. 21, 2006, which claims the benefit of U.S. Provisional Application No. 60/763,261, filed Jan. 30, 2006. This application is also a continuation-in-part application of U.S. patent application Ser. No. 12/403,824, filed Mar. 13, 2009, which is a continuation-in-part application of U.S. patent application Ser. No. 12/389,294, filed Feb. 19, 2009, and which claims the benefit of priority to U.S. Provisional Application No. 61/037,668, filed Mar. 18, 2008. The entire content of each of these applications is hereby expressly incorporated herein by reference.

BACKGROUND OF THE INVENTION

Field of the Invention

The present invention relates in general to phototherapy, and more particularly, to novel apparatuses and methods for phototherapy of brain tissue.

Description of the Related Art

There are numerous neurologic conditions, such as neurodegenerative diseases (e.g., Alzheimer's disease, Parkinson's disease, amyotrophic lateral sclerosis), Huntington's disease, demyelinating diseases (e.g., multiple sclerosis), cranial nerve palsies, traumatic brain injury, stroke, depression, and spinal cord injury which could possibly benefit from application of phototherapy. Most of these conditions cause significant morbidity and mortality and involve tremendous burden to society, families and caregivers. Many neurologic conditions have no currently available effective therapies or the therapies that are available are not adequate to restore functional recovery, sustain quality of life, or halt disease progression.

One example of a neurologic condition that remains a major unmet medical need is stroke, also called cerebrovascular accident (CVA). Stroke is caused by a sudden disruption of blood flow to a discrete area of the brain that is brought on by the lodging of a clot in an artery supplying blood to an area of the brain (called an ischemic stroke), or by a cerebral hemorrhage due to a ruptured aneurysm or a burst artery (called a hemorrhagic stroke). There are over 750,000 stroke victims per year in the United States, and approximately 85% of all strokes are ischemic and 15% are hemorrhagic. The consequence of stroke is a loss of function in the affected brain region and concomitant loss of bodily function in areas of the body controlled by the affected brain region. Depending upon the extent and location of the primary insult in the brain, loss of function varies greatly from mild or severe, and may be temporary or permanent. Lifestyle factors such as smoking, diet, level of physical activity and high cholesterol increase the risk of stroke, and thus stroke is a major cause of human suffering in developed nations. Stroke is the third leading cause of death in most developed nations, including the United States.

Stroke treatment is often restricted to providing basic life support at the time of the stroke, followed by rehabilitation. Currently, the only FDA-cleared treatment of ischemic stroke involves thrombolytic therapy using tissue plasminogen activator (tPA). However, tPA can only be used within three hours of stroke onset and has several contraindications, therefore, only a small percentage of stroke victims receive this drug.

Traumatic brain injury (TBI) occurs when a sudden physical trauma (e.g., crush or compression injury in the central nervous system, including a crush or compression injury of the brain, spinal cord, nerves or retina, or any acute injury or insult producing cell death) causes damage to the head. For example, a sudden and/or violent blow to the head or an object piercing the skull and entering brain tissue can result in TBI. The extent of damage to the brain can be severe, however even mild and moderate TBI has been associated with neurological sequelae that can be long lasting. Development of neurodegenerative conditions has been associated with TBI. TBI can result in a sudden disruption of blood flow to a discrete area of the brain. The consequence of stroke or TBI can be a loss of function in the affected brain region and concomitant loss of bodily function in areas of the body controlled by the affected brain region. Depending upon the extent and location of the primary insult in the brain, loss of function varies greatly from mild or severe, and may be temporary or permanent.

A high level of interest and clinical need remains in finding new and improved therapeutic interventions for treatment of stroke and other neurologic conditions that continue to devastate millions of lives each year and where few effective therapies exist.

SUMMARY OF THE INVENTION

In certain embodiments, an apparatus is wearable by a patient for treating the patient's brain. The apparatus comprises a body adapted to be worn over at least a portion of the patient's scalp. The apparatus further comprises a plurality of indicators corresponding to a plurality of treatment site locations at the patient's scalp where a light source is to be sequentially positioned such that light from the light source is sequentially applied to irradiate at least a portion of the patient's brain. At least one of the indicators comprises an optically transmissive portion of the body having an area of at least 1 cm$^2$ through which the light propagates.

In certain embodiments, an apparatus is wearable by a patient for treating the patient's brain. The apparatus comprises means for identifying a plurality of treatment site locations at the patient's scalp where light is to be applied to irradiate at least a portion of the patient's brain. The apparatus further comprises means for indicating to an operator a sequential order for irradiating the treatment site locations.

In certain embodiments, a method of treating a patient's brain comprises noninvasively irradiating a first area of at least 1 cm$^2$ of the patient's scalp with laser light during a first time period. The method further comprises noninvasively irradiating a second area of at least 1 cm$^2$ of the patient's scalp with laser light during a second time period, wherein the first area and the second area do not overlap one another. The first time period and the second time period do not overlap one another.

In certain embodiments, a method for denoting a brain phototherapy procedure comprises identifying a plurality of treatment site locations at a patient's scalp. The method further comprises indicating a sequential order for irradiation of the treatment site locations. At least one of the treatment site locations has an area of at least 1 cm$^2$.

In certain embodiments, a headpiece is wearable by a patient for treating the patient's brain. The headpiece comprises a plurality of position indicators configured to indicate corresponding treatment site locations at which light is to be applied to non-invasively irradiate at least a portion of the patient's brain. At least one position indicator of the plurality of position indicators comprises an optically transmissive region and a mating portion configured to releasably mate with a complementary portion of a light source. The headpiece is configured to conform to at least a portion of the patient's scalp.

In certain embodiments, a headpiece is wearable by a patient for treating the patient's brain. The headpiece comprises a body configured to generally conform to at least a portion of the patient's scalp. The headpiece further comprises a plurality of position indicators configured to indicate corresponding treatment site locations of the patient's scalp at which light is to be applied to non-invasively irradiate at least a portion of the patient's brain. At least one position indicator of the plurality of position indicators comprising an aperture and a mating portion configured to releasably mate with a complementary portion of a light source. The headpiece also comprises a plurality of labels configured to indicate a predetermined treatment sequence for sequentially applying light from the light source to the treatment site locations. The headpiece further comprises a retaining member extending between a first side of the headpiece and a second side of the headpiece. The retaining member is configured to secure the headpiece to the head of the patient.

In certain embodiments, a system for providing phototherapy to at least a portion of a patient's brain comprises a light emitting device and a wearable headpiece. The light source comprises a light source configured to generate light comprising one or more wavelengths in a range of about 630 nm to about 1064 nanometers, an output optical element in optical communication with the light source, and a docking element. The output optical element is configured to emit at least a portion of the light generated by the light source. The wearable headpiece comprises a plurality of position indicators configured to indicate corresponding treatment site locations of the patient's scalp at which the light is to be applied to irradiate at least a portion of the patient's brain. At least one position indicator of the plurality of position indicators comprises an optically transmissive region and a mating portion configured to releasably mate with the docking element of the light emitting device.

In certain embodiments, a method of providing phototherapy to at least a portion of a patient's brain comprises positioning a wearable headpiece on the patient's head. The method further comprises reversibly mechanically coupling a light source to a first portion of the headpiece while the headpiece is on the patient's head, wherein the headpiece applies a first force to the light source such that light emitted by the light source non-invasively irradiates at least a first portion of the patient's brain by propagating through a first treatment site location of the patient's scalp. The method also comprises removing the light source from the first portion of the headpiece while the headpiece remains on the patient's head.

For purposes of summarizing the present invention, certain aspects, advantages, and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIGS. 15C and 15D schematically illustrate two states of another example sensor in accordance with certain embodiments described herein.

DETAILED DESCRIPTION OF THE PREFERRED EMBODIMENT

Figure 1:
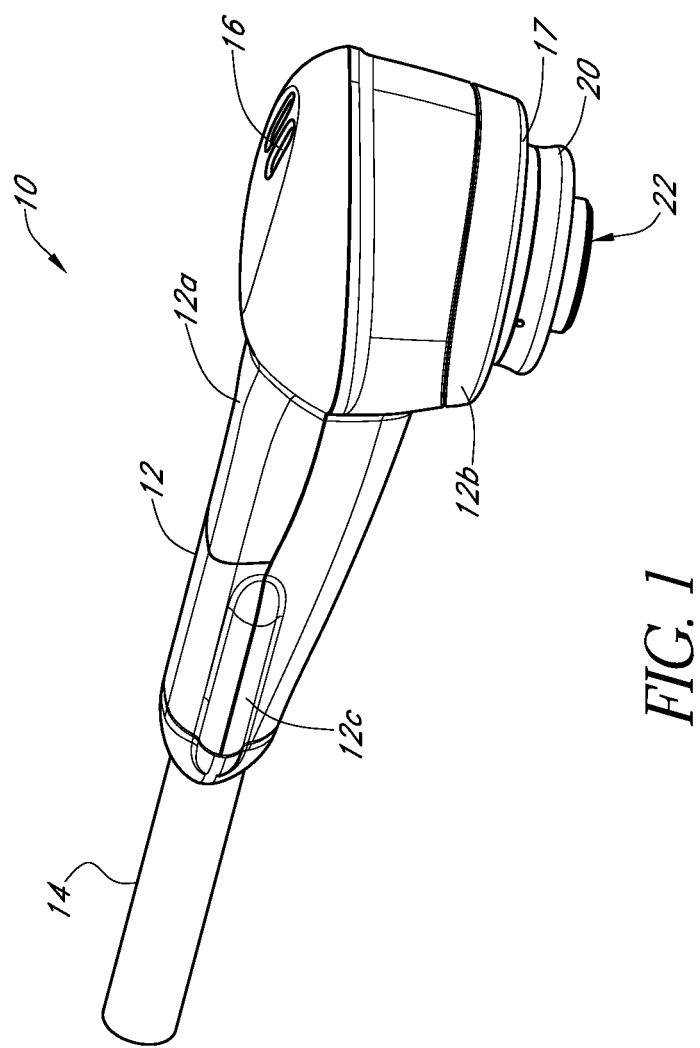
FIG. 1 schematically illustrates an example beam delivery apparatus in accordance with certain embodiments described herein.

Low level light therapy ("LLLT") or phototherapy involves therapeutic administration of light energy to a patient at lower irradiances than those used for cutting, cauterizing, or ablating biological tissue, resulting in desirable biostimulatory effects while leaving tissue undamaged. In non-invasive phototherapy, it is desirable to apply an efficacious amount of light energy to the internal tissue to be treated using light sources positioned outside the body. (See, e.g., U.S. Pat. Nos. 6,537,304 and 6,918,922, both of which are incorporated in their entireties by reference herein.)

Laser therapy has been shown to be effective in a variety of settings, including treating lymphoedema and muscular trauma, and carpal tunnel syndrome. Recent studies have shown that laser-generated infrared radiation is able to penetrate various tissues, including the brain, and to modify function. In addition, laser-generated infrared radiation can induce effects including, but not limited to, angiogenesis, modify growth factor (transforming growth factor-β) signaling pathways, and enhance protein synthesis.

However, absorption of the light energy by intervening tissue can limit the amount of light energy delivered to the target tissue site, while heating the intervening tissue. In addition, scattering of the light energy by intervening tissue can limit the irradiance (or power density) or energy density delivered to the target tissue site. Brute force attempts to circumvent these effects by increasing the power and/or irradiance applied to the outside surface of the body can result in damage (e.g., burning) of the intervening tissue. For example, a patient experiencing TBI can have a significant amount of bleeding within the skull (e.g., "blood in the field"), and this blood can absorb the applied light, thereby inhibiting propagation of light energy to brain tissue below the blood-filled region and heating up.

Non-invasive phototherapy methods are circumscribed by setting selected treatment parameters within specified limits so as to preferably avoid damaging the intervening tissue. A review of the existing scientific literature in this field would cast doubt on whether a set of undamaging, yet efficacious, parameters could be found for treating neurologic conditions. However, certain embodiments, as described herein, provide devices and methods which can achieve this goal.

Such embodiments may include selecting a wavelength of light at which the absorption by intervening tissue is below a damaging level. Such embodiments may also include setting the power output of the light source at low, yet efficacious, irradiances (e.g., between approximately 100 $\mu W/cm^2$ to approximately 10 $W/cm^2$) at the target tissue site, setting the temporal profile of the light applied to the head (e.g., temporal pulse widths, temporal pulse shapes, duty cycles, pulse frequencies), and time periods of application of the light energy at hundreds of microseconds to minutes to achieve an efficacious energy density at the target tissue site being treated. Other parameters can also be varied in the use of phototherapy. These other parameters contribute to the light energy that is actually delivered to the treated tissue and may play key roles in the efficacy of phototherapy. In certain embodiments, the irradiated portion of the brain can comprise the entire brain.

In certain embodiments, the target area of the patient's brain includes the area of injury, e.g., to neurons within the "zone of danger." In other embodiments, the target area includes portions of the brain not within the zone of danger. Information regarding the biomedical mechanisms or reactions involved in phototherapy is provided by Tiin a I. Karu in "Mechanisms of Low-Power Laser Light Action on Cellular Level", Proceedings of SPIE Vol. 4159 (2000), Effects of Low-Power Light on Biological Systems V, Ed. Rachel Lubart, pp. 1-17, and Michael R. Hamblin et al., "Mechanisms of Low Level Light Therapy," Proc. of SPIE, Vol. 6140, 614001 (2006), each of which is incorporated in its entirety by reference herein.

In certain embodiments, the apparatuses and methods of phototherapy described herein are used to treat physical trauma (e.g., TBI or ischemic stroke) or other sources of neurodegeneration. As used herein, the term "neurodegeneration" refers to the process of cell destruction resulting from primary destructive events such as stroke or CVA, as well as from secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amylotrophic lateral sclerosis, heat stroke, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules, including but not limited to, apoptosis, depletion of cellular energy stores because of changes in mitochondrial membrane permeability, release or failure in the reuptake of excessive glutamate, reperfusion injury, and activity of cytokines and inflammation. Both primary and secondary mechanisms contribute to forming a "zone of danger" for neurons, wherein the neurons in the zone have at least temporarily survived the primary destructive event, but are at risk of dying due to processes having delayed effect.

In certain embodiments, the apparatuses and methods described herein are used to provide neuroprotection. As used herein, the term "neuroprotection" refers to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

In certain embodiments, the apparatuses and methods described herein are used to improve neurologic function, to provide neurologic enhancement, or to regain previously lost neurologic function. The term "neurologic function" as used herein includes both cognitive function and motor function. The term "neurologic enhancement" as used herein includes both cognitive enhancement and motor enhancement. The terms "cognitive enhancement" and "motor enhancement" as used herein refer to the improving or heightening of cognitive function and motor function, respectively.

The term "cognitive function" as used herein refers to cognition and cognitive or mental processes or functions, including those relating to knowing, thinking, learning, perception, memory (including immediate, recent, or remote memory), and judging. Symptoms of loss of cognitive function can also include changes in personality, mood, and behavior of the patient. The term "motor function" as used herein refers to those bodily functions relating to muscular movements, primarily conscious muscular movements, including motor coordination, performance of simple and complex motor acts, and the like.

Diseases or conditions affecting neurologic function include, but are not limited to, Alzheimer's disease, dementia, AIDS or HIV infection, Cruetzfeldt-Jakob disease, head trauma (including single-event trauma and long-term trauma such as multiple concussions or other traumas which may result from athletic injury), Lewy body disease, Pick's disease, Parkinson's disease, Huntington's disease, drug or alcohol abuse, brain tumors, hydrocephalus, kidney or liver disease, stroke, depression, and other mental diseases which cause disruption in cognitive function, and neurodegeneration.

Beam Delivery Apparatus

The phototherapy methods for the treatment of neurologic conditions (e.g., ischemic stroke, Alzheimer's Disease, Parkinson's Disease, depression, or TBI) described herein may be practiced and described using various light delivery systems. Such light delivery systems may include a low level laser therapy apparatus such as that shown and described in U.S. Pat. Nos. 6,214,035; 6,267,780; 6,273,905; 6,290,714; 7,303,578; and 7,575,589 and in U.S. Pat. Appl. Publ. Nos. 2005/0107851 A1 and 2009/0254154 A1, each of which is incorporated in its entirety by reference herein. For example, in certain embodiments, the light delivery apparatus can irradiate a portion of the patient's scalp or skull while cooling the irradiated portion of the scalp or skull. In certain other embodiments, the irradiated portion of the patient's scalp or skull is not cooled while irradiating the portion of the scalp or skull.

These previously-disclosed light delivery apparatuses were described primarily in conjunction with phototherapy treatment of stroke, however in certain embodiments, such light delivery apparatuses can also be used for phototherapy treatment of other neurologic conditions (e.g., Alzheimer's Disease, Parkinson's Disease, Huntington's Disease, depression, TBI). A patient who has experienced a TBI may have a portion of their scalp damaged, thereby exposing a portion of their cranium or skull. In certain such embodiments, the light delivery apparatus can irradiate an exposed portion of the cranium or skull without the light propagating through scalp tissue. Certain embodiments described herein are compatible with irradiation of the brain with light applied to at least a portion of the scalp or with light applied to at least a portion of the cranium or skull without propagating through the scalp.

FIG. 1 schematically illustrates an example beam delivery apparatus 10 in accordance with certain embodiments described herein. The apparatus 10 comprises a housing 12, a flexible conduit 14 operatively coupled to the housing 12, and at least one status indicator 16. In certain embodiments, the apparatus 10 comprises an output optical assembly 20 comprising an emission surface 22 through which a light beam 30 is emitted. The output optical assembly 20 is configured to be releasably mechanically coupled to other components of the apparatus 10. The output optical assembly 20 can also be configured to be releasably coupled to a position indicator of a wearable headpiece, as described further herein.

In certain embodiments, the housing 12 is sized to be easily held in one hand (e.g., having a length of approximately 5½ inches). The housing 12 of certain embodiments further comprises one or more portions 12a, 12b comprising a biocompatible material since they may contact the operator, the patient, or both. For example, one or more low durometer elastomer materials (e.g., rubber, polymers, thermoplastic resins) can be used in certain embodiments. The portion 12a is configured to be grasped by a user's hand during operation of the apparatus 10. The housing 12 of certain embodiments is configured so that the emission surface 22 can be held in position and sequentially moved by hand to irradiate selected portions of the patient's skin. In certain embodiments, the housing 12 comprises one or more recesses or protrusions which facilitate the housing 12 being gripped by the user. In certain embodiments, the housing 12 is configured to be placed on a testing system to measure or monitor the operative parameters of the apparatus 10. The housing 12 of certain such embodiments comprises an alignment rib 12c configured to provide a registration protrusion which mates with a corresponding registration recess on the testing system to facilitate proper alignment of the emission surface 22 with the testing system. The housing 12 of certain embodiments comprises two or more portions (e.g., 2-piece cast urethane with 60 A overmolding or 3-piece Lustran® with thermoplastic elastomer overmolding) which fit together to form a shell in which other operative components are held. In certain embodiments, the light used by the apparatus 10 can cause eye damage if viewed by an individual. In such embodiments, the apparatus 10 can be configured to provide eye protection so as to avoid viewing of the light by individuals. For example, opaque materials can be used for the housing 12 and appropriately placed to block the light from being viewed directly. In addition, interlocks can be provided so that the light source is not activated unless the apparatus 10 is in place, or other appropriate safety measures are taken.

In certain embodiments, the housing 12 further comprises a flexible boot 17 generally surrounding the portion of the apparatus 10 which is releasably mounted to the output optical assembly 20. The boot 17 of certain embodiments provides a barrier to control, inhibit, prevent, minimize, or reduce contaminants from entering the housing 12. Thus, by virtue of the boot 17 providing a barrier, the contamination entering the housing 12 is lower than it would otherwise be if the boot 17 did not provide a barrier. Example materials for the flexible boot 17 include but are not limited to, rubber or another elastomer.

In certain embodiments, the conduit 14 is configured to operatively couple the apparatus 10 to various control, power, and cooling systems that are spaced from the housing 12. In certain embodiments, the conduit 14 comprises at least one optical fiber configured to transmit light from a light source to the apparatus 10 to be emitted from the emission surface 22. In certain embodiments, the conduit 14 further comprises one or more electrically conductive wires (e.g., one 20-conductor cable, four 6-conductor cables, ground braid) configured to transmit signals between the apparatus 10 (e.g., trigger switches or temperature sensors within the apparatus 10) and a control system spaced from the apparatus 10 and/or to provide electrical power to the apparatus 10 (e.g., for a thermoelectric cooler) from a power system. In still other embodiments, the apparatus 10 comprises a power source (e.g., a battery). In certain embodiments, the conduit 14 comprises one or more coolant tubes (e.g., 0.125-inch inner diameter) configured to have a coolant (e.g., liquid or gas) flow to the apparatus 10 from a cooling system. In certain embodiments, the conduit 14 comprises one or more connectors which are mechanically coupled to one or more corresponding connectors within the housing 12. For example, the conduit 14 can comprise an SMA connector at an end of the optical fiber which is mechanically coupled to a corresponding SMA mount within the housing 12.

In certain embodiments, the conduit 14 comprises a protective sheath around the one or more fibers, wires, and tubes of the conduit 14. The protective sheath of certain embodiments controls, inhibits, prevents, minimizes, or reduces light from exiting the conduit 14 in the event of a failure of the at least one optical fiber. Thus, by virtue of having the sheath, the light exiting the conduit 14 upon fiber failure is lower than it would otherwise be without the sheath. In certain embodiments, the protective sheath comprises a strain relief apparatus having a plurality of rigid segments (e.g., stainless steel), with each segment having a generally cylindrical tubular shape and a longitudinal axis. Each segment is articulately coupled to neighboring segments such that an angle between the longitudinal axes of neighboring segments is limited to be less than a predetermined angle. In certain embodiments, the protective sheath allows the conduit 14 to be moved and to bend, but advantageously limits the radius of curvature of the bend to be sufficiently large to avoid breaking the one or more fibers, wires, or tubes therein. In certain embodiments, the sheath comprises a flexible compression spring (e.g., 4 inches in length) to provide bend relief and/or a tension line to provide strain relief.

In certain embodiments, the at least one status indicator 16 comprises one, two, or more light-emitting diodes (LEDs) which are lit to visually provide the user with information regarding the status of the apparatus 10. For example, the at least one status indicator 16 can be used in certain embodiments to indicate when the laser source is ready to lase pending engagement of the trigger. In certain embodiments, the LEDs can be lit to show different colors depending on whether the optical power, electrical power, or coolant flow being provided to the apparatus 10 are sufficient for operation of the apparatus 10. In certain embodiments, the at least one status indicator 16 provides information regarding whether the output optical assembly 20 is properly mounted to the apparatus 10. Other types of status indicators (e.g., flags, sound alarms) are also compatible with certain embodiments described herein.

Figure 2A:
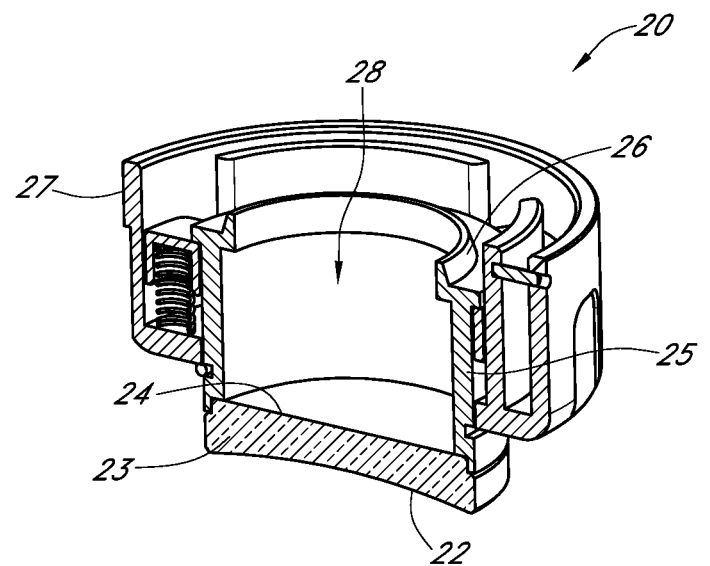
FIG. 2A schematically illustrates a cross-sectional view of an example output optical assembly in accordance with certain embodiments described herein.
Figure 2B:
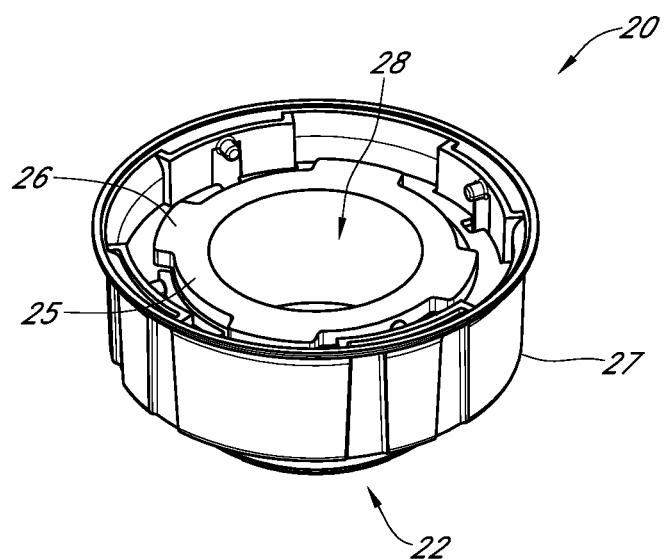
FIG. 2B schematically illustrates another example output optical assembly in accordance with certain embodiments described herein.

FIG. 2A schematically illustrates a cross-sectional view of an example output optical assembly 20 in accordance with certain embodiments described herein. FIG. 2B schematically illustrates another example output optical assembly 20 in accordance with certain embodiments described herein. The output optical assembly 20 comprises an optical element 23 comprising the emission surface 22 and a surface 24 facing generally away from the emission surface 22. As used herein, the term "element" is used in its broadest sense, including, but not limited to, as a reference to a constituent or distinct part of a composite device. The output optical assembly 20 further comprises a thermal conduit 25 in thermal communication with the optical element 23 (e.g., with a portion of the surface 24). The thermal conduit 25 comprises at least one surface 26 configured to be in thermal communication with at least one heat dissipating surface of the apparatus 10 (e.g., a surface of a cooling mechanism). The output optical assembly 20 further comprises a coupling portion 27 (e.g., spring-loaded 3-pin bayonet mount or 4-pin bayonet mount) configured to be releasably attached and detached from the housing 12. In certain embodiments, the output optical assembly 20 comprises one or more springs which provide a sufficient force on the at least one surface 26 towards the at least one heat dissipating surface of the apparatus 10 to have the desired thermal conductivity between the two. Various examples of output optical assemblies 20 compatible with certain embodiments described herein are described more fully in U.S. patent application Ser. No. 12/233,498, which is incorporated in its entirety by reference herein.

In certain embodiments, the output optical assembly 20 is configured to be placed in thermal communication with the patient's scalp or skull (e.g., the optical element 23 is configured to contact the patient's scalp or skull or is configured to be spaced from the patient's scalp or skull but to contact a thermally conductive material in contact with the patient's scalp or skull). In certain embodiments in which the output optical assembly 20 is cooled, the output optical assembly 20 cools at least a portion of the patient's scalp or skull (e.g., the portion of the scalp or skull being irradiated). Thus, in certain embodiments, the output optical assembly 20 is adapted to control, inhibit, prevent, minimize, or reduce temperature increases at the scalp or skull caused by the light. Thus, by virtue of the output optical assembly 20 cooling the portion of the patient's scalp or skull being irradiated, the temperature of the irradiated portion of the patient's scalp or skull is lower than it would otherwise be if the output optical assembly 20 did not cool the irradiated portion of the scalp or skull. For example, by cooling the irradiated portion of the patient's scalp or skull using the output optical assembly 20, the temperature of the irradiated portion of the patient's scalp or skull can be higher than the temperature of the portion of the patient's scalp or skull if it were not irradiated, but lower than the temperature of the portion of the patient's scalp or skull if it were irradiated but not cooled. In certain embodiments, the patient's scalp comprises hair and skin which cover the patient's skull. In other embodiments, at least a portion of the hair is removed prior to the phototherapy treatment, so that the output optical assembly 20 substantially contacts the skin of the scalp.

The optical element 23 of certain embodiments is thermally conductive, and optically transmissive at wavelengths which are transmitted by skin. For example, in certain embodiments, the thermal conductivity of the optical element 23 is sufficient to remove heat from the irradiated portion of the patient's scalp or skull, and the optical transmissivity of the optical element 23, at wavelengths selected to provide the desired irradiance at a target region of the brain, is sufficient to allow the desired irradiance of light to propagate through the optical element 23 to irradiate the patient's scalp or skull. In certain embodiments, the optical element 23 comprises a rigid material, while in certain other embodiments, the optical element 23 comprises a low durometer, thermally conductive, optically transmissive material (e.g., a flexible bag or container filled with a thermally conductive, optically transmissive liquid such as water). Example rigid materials for the optical element 23 include, but are not limited to, sapphire, diamond, calcium fluoride, and zinc selenide. In certain embodiments, the optical element 23 has an emission surface 22 configured to face generally towards the surface to be irradiated (e.g., the patient's scalp or skull). In certain embodiments, the emission surface 22 is adapted to be placed in contact with either the irradiated surface or with a substantially optically transmissive and substantially thermally conductive material which is in contact with the irradiated surface. The emission surface 22 of certain embodiments is configured to be in thermal communication with the surface to be irradiated by the light beam emitted from the emission surface 22. In certain such embodiments, the thermal conductivity of the optical element 23 is sufficiently high to allow heat to flow from the emission surface 22 to the thermal conduit 25 at a sufficient rate to control, inhibit, prevent, minimize, or reduce damage to the skin or discomfort to the patient from excessive heating of the skin due to the irradiation. Thus, by virtue of the thermal conductivity of the optical element 23, any damage to the skin or discomfort to the patient can be lower than it would otherwise be if the optical element 23 did not have a sufficiently high thermal conductivity. For example, the damage to the skin or discomfort to the patient can be higher than it would be if the portion of the patient's scalp were not irradiated, but the damage to the skin or discomfort to the patient would be lower than it would be if the optical element 23 did not have a sufficiently high thermal conductivity.

In certain embodiments, the optical element 23 has a thermal conductivity of at least approximately 10 watts/meter-K. In certain other embodiments, the thermal conductivity of the optical element 23 is at least approximately 15 watts/meter-K. Examples of materials for the optical element 23 in accordance with certain embodiments described herein include, but are not limited to, sapphire which has a thermal conductivity of approximately 23.1 watts/meter-K, and diamond which has a thermal conductivity between approximately 895 watts/meter-K and approximately 2300 watts/meter-K.

In certain embodiments, the emission surface 22 is adapted to conform to the curvature of the scalp or skull. The emission surface 22 of certain embodiments is concave (e.g., generally spherical with a radius of curvature of about 100 millimeters). By fitting to the curvature of the scalp or skull, the emission surface 22 advantageously controls, inhibits, prevents, minimizes, or reduces temperature increases at the scalp or skull that would otherwise result from air-filled gaps between the emission surface 22 and the scalp or skull. Thus, by virtue of the emission surface 22 fitting to the curvature of the portion of the patient's scalp or skull being irradiated, the temperature of the irradiated portion of the patient's scalp or skull is lower than it would otherwise be if the emission surface 22 did not fit to the curvature of the irradiated portion of the scalp or skull. For example, by fitting the emission surface 22 to the curvature of the irradiated portion of the patient's scalp or skull, the temperature of the irradiated portion of the patient's scalp or skull can be higher than the temperature of the portion of the patient's scalp or skull if it were not irradiated, but lower than the temperature of the portion of the patient's scalp or skull if it were irradiated but the emission surface 22 did not fit to the portion of the patient's scalp or skull. The existence of air gaps between the emission surface 22 and the scalp or skull can reduce the thermal conductivity between the emission surface 22 and the scalp or skull, thereby increasing the probability of heating the scalp or skull by the irradiation.

In addition, the refractive-index mismatches between such an air gap and the emission surface 22 and/or the scalp or skull can cause a portion of the light propagating toward the scalp or skull to be reflected away from the scalp or skull. In certain embodiments, the emission surface 22 is placed in contact with the skin of the scalp or skull so as to advantageously substantially reduce air gaps between the emission surface 22 and the scalp or skull in the optical path of the light. In certain other embodiments in which an intervening material (e.g., a substantially optically transmissive and substantially thermally conductive gel) is in contact with the scalp or skull and with the emission surface 22, the emission surface 22 is placed in contact with the intervening material so as to advantageously avoid creating air gaps between the emission surface 22 and the intervening material or between the intervening material and the scalp or skull. In certain embodiments, the intervening material has a refractive index at a wavelength of light impinging the scalp which substantially matches the refractive index of the scalp (e.g., about 1.3), thereby reducing any index-mismatch-generated back reflections between the emission surface 22 and the scalp. Examples of materials compatible with certain such embodiments described herein include, but are not limited to, glycerol, water, and silica gels. Example index-matching gels include, but are not limited to, those available from Nye Lubricants, Inc. of Fairhaven, Mass.

In certain embodiments, the emission surface 22 comprises one or more optical coatings, films, layers, membranes, etc. in the optical path of the transmitted light which are adapted to reduce back reflections. By reducing back reflections, the emission surface 22 increases the amount of light transmitted to the brain and reduces the need to use higher irradiances which may otherwise create temperature increases at the scalp or skull.

Figure 3A:
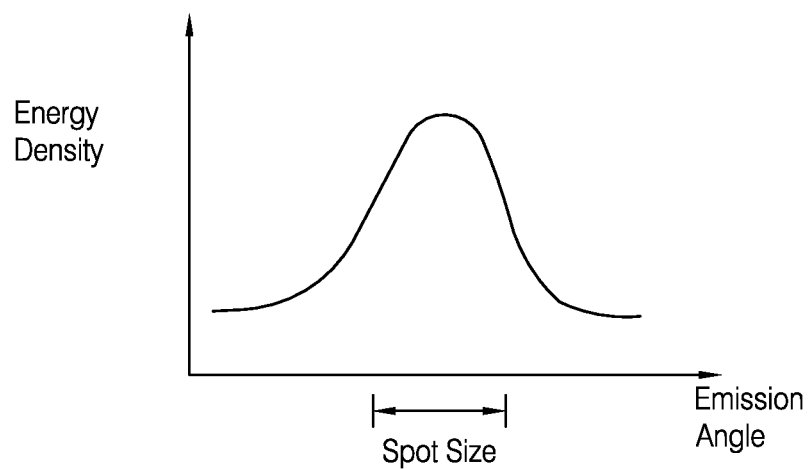
FIGS. 3A and 3B schematically illustrate the diffusive effect on the light by the output optical assembly.
Figure 3B:
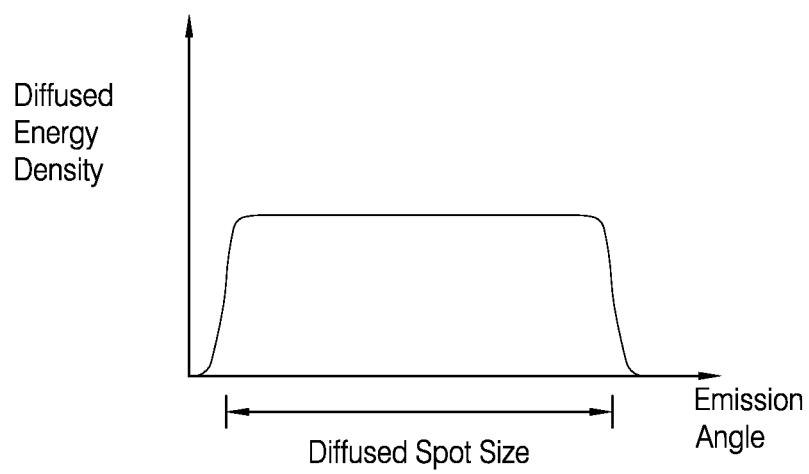

In certain embodiments, the output optical assembly 20 is adapted to diffuse the light prior to reaching the scalp or skull to advantageously homogenize the light beam prior to reaching the emission surface 22. Generally, intervening tissues of the scalp and skull are highly scattering, which can reduce the impact of non-uniform beam intensity distributions on the illumination of the patient's cerebral cortex. However, non-uniform beam intensity distributions with substantial inhomogeneities could result in some portions of the patient's scalp or skull being heated more than others (e.g., localized heating where a "hot spot" of the light beam impinges the patient's scalp or skull). In certain embodiments, the output optical assembly 20 advantageously homogenizes the light beam to have a non-uniformity less than approximately 3 millimeters. FIGS. 3A and 3B schematically illustrate the diffusive effect on the light by the output optical assembly 20. An example energy density profile of the light prior to being transmitted through the output optical assembly 20, as illustrated by FIG. 3A, is peaked at a particular emission angle. After being diffused by the output optical assembly 20, as illustrated by FIG. 3B, the energy density profile of the light does not have a substantial peak at any particular emission angle, but is substantially evenly distributed among a range of emission angles. By diffusing the light, the output optical assembly 20 distributes the light energy substantially evenly over the area to be illuminated, thereby controlling, inhibiting, preventing, minimizing, or reducing "hot spots" which would otherwise create temperature increases at the scalp or skull. Thus, by virtue of the output optical assembly 20 diffusing the light, the temperature of the irradiated portion of the patient's scalp or skull is lower than it would otherwise be if the output optical assembly 20 did not diffuse the light. For example, by diffusing the light using the output optical assembly 20, the temperature of the irradiated portion of the patient's scalp or skull can be higher than the temperature of the portion of the patient's scalp or skull if it were not irradiated, but lower than the temperature of the portion of the patient's scalp or skull if it were irradiated but the light were not diffused by the output optical assembly 20. In addition, by diffusing the light prior to reaching the scalp or skull, the output optical assembly 20 can effectively increase the spot size of the light impinging the scalp or skull, thereby advantageously lowering the irradiance at the scalp or skull, as described in U.S. Pat. No. 7,303,578, which is incorporated in its entirety by reference herein.

In certain embodiments, the output optical assembly 20 provides sufficient diffusion of the light such that the irradiance of the light is less than a maximum tolerable level of the scalp, skull, or brain. For example, the maximum tolerable level of certain embodiments is a level at which the patient experiences discomfort or pain, while in certain other embodiments, the maximum level is a level at which the patient's scalp or skull is damaged (e.g., burned). In certain other embodiments, the output optical assembly 20 provides sufficient diffusion of the light such that the irradiance of the light equals a therapeutic value at the subdermal target tissue. The output optical assembly 20 can comprise example diffusers including, but are not limited to, holographic diffusers such as those available from Physical Optics Corp. of Torrance, Calif. and Display Optics P/N SN1333 from Reflexite Corp. of Avon, Conn.

In certain embodiments, the output optical assembly 20 provides a reusable interface between the apparatus 10 and the patient's scalp or skull. In such embodiments, the output optical assembly 20 can be cleaned or sterilized between uses of the apparatus 10, particularly between uses by different patients. In other embodiments, the output optical assembly 20 provides a disposable and replaceable interface between the apparatus 10 and the patient's scalp or skull. By using pre-sterilized and pre-packaged replaceable interfaces, certain embodiments can advantageously provide sterilized interfaces without undergoing cleaning or sterilization processing immediately before use.

In certain embodiments, the output optical assembly 20 is adapted to apply pressure to at least an irradiated portion of the scalp. For example, the output optical assembly 20 is capable of applying pressure to at least an irradiated portion of the scalp upon a force being applied to the apparatus 10 (e.g., by an operator of the apparatus 10 pressing the apparatus 10 against the patient's scalp by hand or by mechanical means to generate force, such as weights, springs, tension straps). By applying sufficient pressure, the output optical assembly 20 can blanch the portion of the scalp by forcing at least some blood out the optical path of the light energy. (For a general discussion of skin blanching, see, e.g., A. C. Burton et al., "Relation Between Blood Pressure and Flow in the Human Forearm," J. Appl. Physiology, Vol. 4, No. 5, pp. 329-339 (1951); A. Matas et al., "Eliminating the Issue of Skin Color in Assessment of the Blanch Response," Adv. in Skin & Wound Care, Vol. 14(4, part 1 of 2), pp. 180-188 (July/August 2001); J. Niitsuma et al., "Experimental study of decubitus ulcer formation in the rabbit ear lobe," J. of Rehab. Res. and Dev., Vol. 40, No. 1, pp. 67-72 (January/February 2003).) The blood removal resulting from the pressure applied by the output optical assembly 20 to the scalp decreases the corresponding absorption of the light energy by blood in the scalp. As a result, temperature increases due to absorption of the light energy by blood at the scalp are reduced. As a further result, the fraction of the light energy transmitted to the subdermal target tissue of the brain is increased. In certain embodiments, a pressure of at least 0.1 pound per square inch is used to blanch the irradiated portion of the scalp, while in certain other embodiments, a pressure of at least one pound per square inch is used to blanch the irradiated portion of the scalp. In certain embodiments, a pressure of at least about two pounds per square inch is used to blanch the irradiated portion of the scalp. Other values or ranges of pressures for blanching the irradiated portion of the scalp are also compatible with certain embodiments described herein. The maximum pressure used to blanch the irradiated portion of the scalp is limited in certain embodiments by patient comfort levels and tissue damage levels.

Figure 4A:
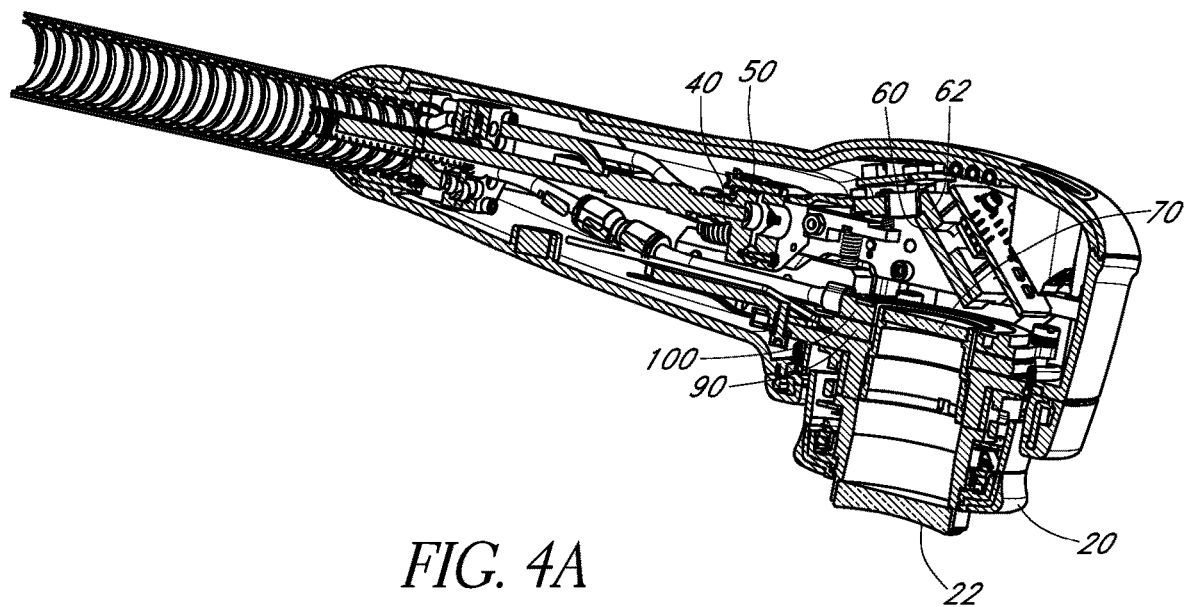
FIGS. 4A and 4B schematically illustrate cross-sectional views of two example beam delivery apparatuses in accordance with certain embodiments described herein.
Figure 4B:
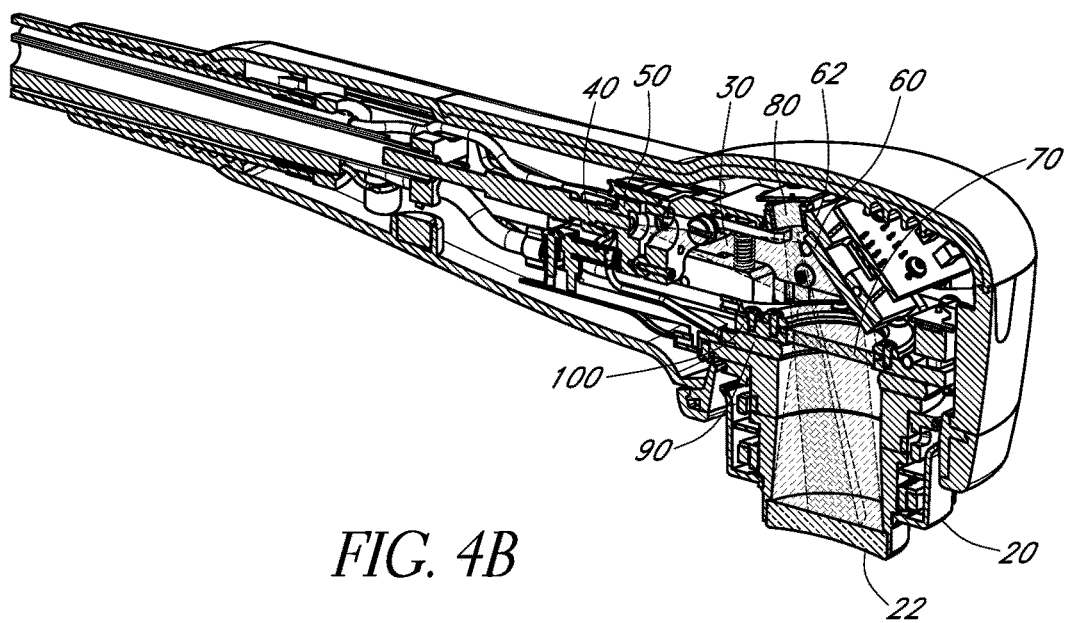

FIGS. 4A and 4B schematically illustrate cross-sectional views of two example beam delivery apparatuses 10 in accordance with certain embodiments described herein. In FIGS. 4A and 4B, the apparatus 10 comprises an output optical assembly 20 having an emission surface 22 and releasably operatively coupled to the other components of the apparatus 10. The apparatus 10 comprises an optical fiber 40, a fiber alignment mechanism 50 operatively coupled to the optical fiber 40, a mirror 60 in optical communication with the optical fiber 40, and a window 70 in optical communication with the mirror 60. During operation of the apparatus 10, light 30 from the optical fiber 40 propagates to the mirror 60 and is reflected by the mirror 60 to propagate through the window 70. The light 30 transmitted through the window 70 propagates through the output optical assembly 20 along a first optical path and is emitted from the emission surface 22. In certain embodiments, the apparatus 10 comprises additional optical elements (e.g., lenses, diffusers, and/or waveguides) which transmit at least a portion of the light received via the optical fiber 40 to the emission surface 22. In certain such embodiments, the additional optical elements of the apparatus 10 shape, format, or otherwise modify the light such that the light beam emitted from the emission surface 22 has the desired beam intensity profile.

In certain embodiments, the optical fiber 40 comprises a step-index or graded-index optical fiber. The optical fiber 40 of certain embodiments is single-mode, while in certain other embodiments, the optical fiber is multimode. An example optical fiber 40 compatible with certain embodiments described herein has a 1000-micron diameter and a numerical aperture of approximately 0.22.

Figure 5:
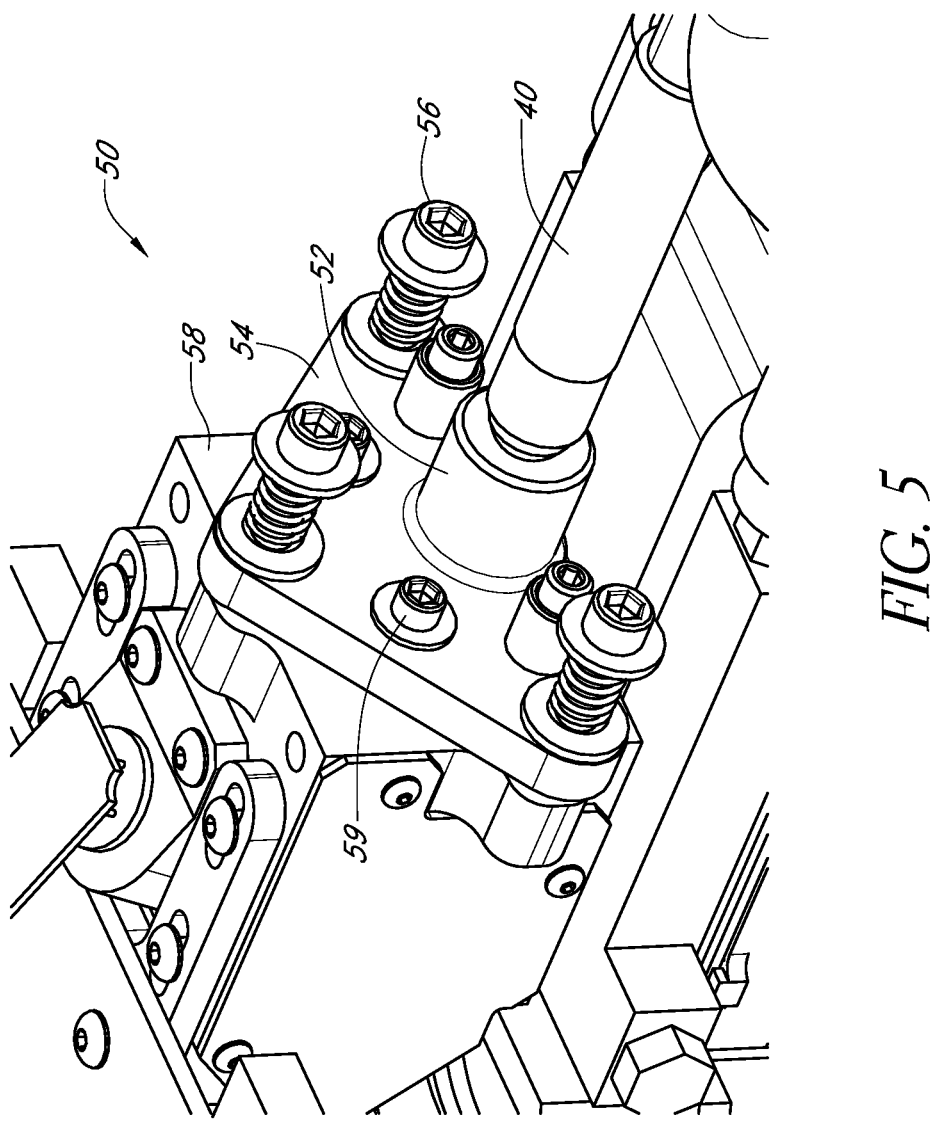
FIG. 5 schematically illustrates an example fiber alignment mechanism in accordance with certain embodiments described herein.

FIG. 5 schematically illustrates an example fiber alignment mechanism 50 in accordance with certain embodiments described herein. In certain embodiments, the fiber alignment mechanism 50 is mechanically coupled to a portion of the optical fiber 40 and is configured to allow adjustments of the position, tilt, or both of the end of the optical fiber 40 from which the light is emitted. In certain embodiments, the fiber alignment mechanism 50 provides an adjustment range of at least ±5 degrees. The fiber alignment mechanism 50 of FIG. 5 comprises a connector 52 (e.g., SMA connector) mechanically coupled to the optical fiber 40, a plate 54 (e.g., a kinematic tilt stage) mechanically coupled to the connector 52, and a plurality of adjustment screws 56 (e.g., 80 turns per inch or 100 turns per inch) adjustably coupled to the plate 54. By turning the adjustment screws 56, a distance between a portion of the plate 54 and a corresponding portion of a reference structure 58 can be adjusted. In certain embodiments, the fiber alignment mechanism 50 comprises one or more locking screws 59 configured to be tightened so as to fix the plate 54 at a position, orientation, or both relative to the reference structure 58. Other configurations of the fiber alignment mechanism 50 are also compatible with certain embodiments described herein.

Figure 6:
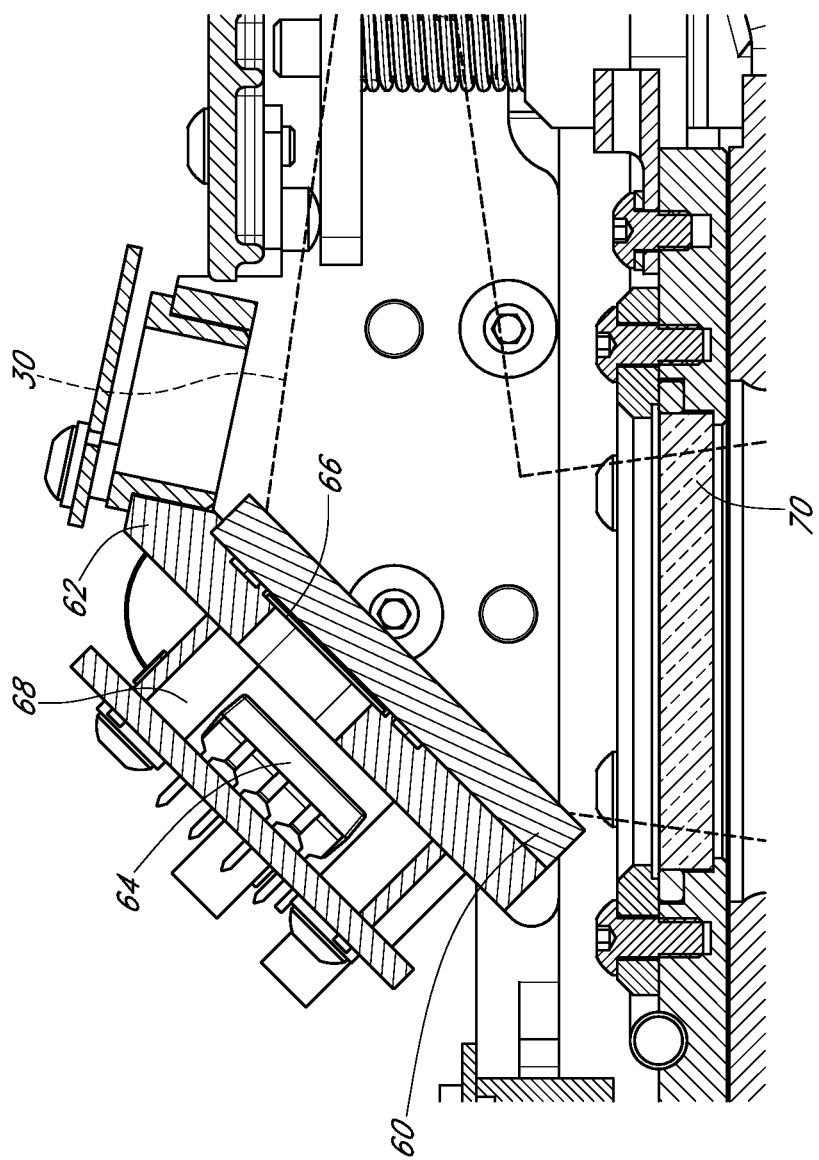
FIG. 6 schematically illustrates an example mirror compatible with certain embodiments described herein.

FIG. 6 schematically illustrates an example mirror 60 compatible with certain embodiments described herein. In certain embodiments, the mirror 60 is substantially reflective of light emitted from the optical fiber 40 to reflect the light through a non-zero angle (e.g., 90 degrees). The mirror 60 of certain embodiments comprises a glass substrate coated on at least one side by a metal (e.g., gold or aluminum). Examples of mirrors 60 compatible with certain embodiments described herein include, but are not limited to, a flat, generally planar glass mirror (e.g., NT43-886 available from Edmund Optics Inc. of Barrington, N.J.). The mirror 60 of certain embodiments can be configured to have an optical power (e.g., the mirror 60 can be concave) and be adapted to shape, format, or otherwise modify the light to produce a desired beam intensity profile. In certain embodiments, the mirror 60 is bonded around its perimeter by an adhesive (e.g., OP-29 adhesive available from Dymax Corp. of Torrington, Conn.) to a support structure 62.

In certain embodiments, the mirror 60 is partially transmissive of light emitted from the optical fiber 40. In certain such embodiments, the support structure 62 comprises an opening and the apparatus 10 comprises at least one light sensor 64 positioned to receive light transmitted through the mirror 60 and the opening of the support structure 62. The at least one light sensor 64 is configured to generate a signal indicative of the intensity of the received light, thereby providing a measure of the intensity of the light reaching the mirror 60. Examples of light sensors 64 compatible with certain embodiments described herein include, but are not limited to, OPT101 photodiode available from Texas Instruments of Dallas, Tex. In certain embodiments, a plurality of light sensors 64 are used to provide operational redundancy to confirm that light with a sufficient intensity for operation of the apparatus 10 is being provided by the optical fiber 40. In certain embodiments, a diffuser 66 is positioned to diffuse the light transmitted through the mirror 60 before the light impinges the light sensor 64. In certain embodiments, the light sensor 64 is protected from stray light by an opaque shroud 68 generally surrounding the light sensor 64.

In certain embodiments, the window 70 is substantially transmissive to infrared radiation. Example windows 70 compatible with certain embodiments described herein include, but are not limited to, a flat, generally planar $CaF_2$ window (e.g., TechSpec® calcium fluoride window available from Edmund Optics Inc. of Barrington, N.J.).

In certain embodiments, the window 70 at least partially bounds a region within the apparatus 10 which contains the mirror 60. The window 70 of certain such embodiments substantially seals the region against contaminants (e.g., dust, debris) from entering the region from outside the region. For example, when the output optical assembly 20 is decoupled from the apparatus 10, the window 70 controls, inhibits, prevents, minimizes, or reduces contaminants entering the region. Thus, by virtue of the window 70 substantially sealing the region, the contamination of the region is lower than it would otherwise be if the window 70 did not substantially seal the region.

Figure 7:
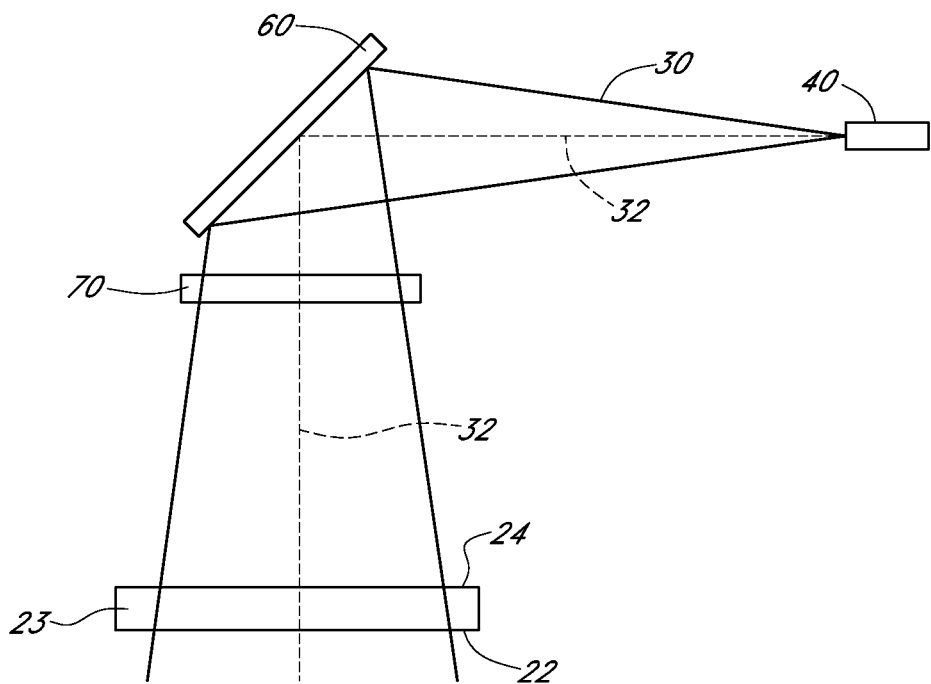
FIG. 7 schematically illustrates an example first optical path of light emitted from the optical fiber in accordance with certain embodiments described herein.

FIG. 7 schematically illustrates an example first optical path 32 of light 30 emitted from the optical fiber 40 in accordance with certain embodiments described herein. The diverging light 30 exiting the optical fiber 40 propagates along the first optical path 32 towards the mirror 60. The light 30 is reflected by the mirror 60 and propagates along the first optical path 32 through the window 70, impinges or is received by the surface 24 of the optical element 23, and is emitted from the emission surface 22 towards the surface to be irradiated. In certain embodiments, the mirror 60 reflects the light 30 through an angle of about 90 degrees. In certain embodiments, the mirror 60 is about 2.3 inches from the face of the optical fiber 40 and the first optical path 32 is about 4.55 inches in length from the fiber output face to the emission surface 22 of the optical element 23.

Figure 8:
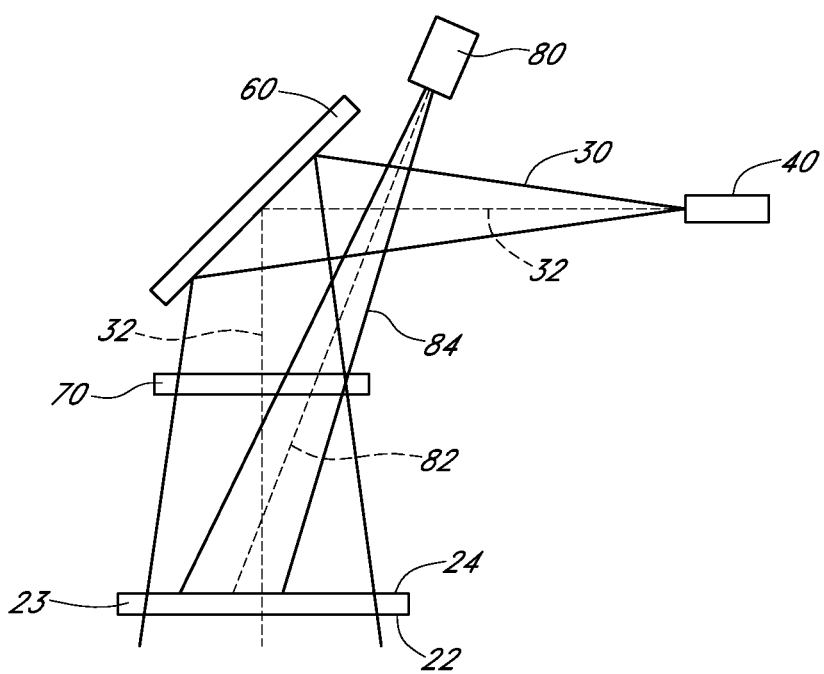
FIG. 8 schematically illustrates an example second optical path of radiation received by the sensor.

In certain embodiments, the apparatus 10 further comprises a sensor 80 spaced from the output optical assembly 20. FIG. 8 schematically illustrates an example second optical path 82 of radiation 84 received by the sensor 80. The sensor 80 is positioned to receive the radiation 84 from the output optical assembly 20 propagating through the output optical assembly 20 along the second optical path 82. The first optical path 32 and the second optical path 82 have a non-zero angle therebetween. In certain embodiments, the second optical path 82 is co-planar with the first optical path 32, while in certain other embodiments, the first optical path 32 and the second optical path 82 are non-co-planar with one another. The sensor 80 of certain embodiments receives radiation 84 propagating along the second optical path 82 from at least a portion of the surface 24 of the optical element 23 during operation of the apparatus 10.

The sensor 80 of certain embodiments comprises a temperature sensor (e.g., thermopile) configured to receive infrared radiation from a region and to generate a signal indicative of the temperature of the region. Examples of temperature sensors compatible with certain embodiments described herein include, but are not limited to, DX-0496 thermopile available from Dexter Research Center, Inc. of Dexter, Mich. In certain embodiments, the field-of-view of the sensor 80 comprises an area of about 0.26 square inches of the surface 24 spaced from the thermal conduit 25 (e.g., by a distance between 0.05 inch and 0.3 inch). In certain other embodiments, the field-of-view of the sensor 80 comprises an area of about 0.57 square inches of the surface 24.

In certain embodiments, the sensor 80 is responsive to the received radiation 84 by generating a signal indicative of a temperature of the skin or of a portion of the output optical assembly 20 (e.g., the optical element 23). In certain such embodiments, the apparatus 10 further comprises a controller configured to receive the signal from the sensor 80 and to cause a warning to be generated, to turn off a source of the light propagating along the first optical path 32, or both in response to the signal indicating that the temperature is above a predetermined threshold temperature (e.g., 42 degrees Celsius).

The sensor 80 of certain embodiments is not in thermal communication with the output optical assembly 20. As shown in FIG. 8, the infrared-transmissive window 70 is between the sensor 80 and the output optical assembly 20. The light 30 propagating along the first optical path 32 and the infrared radiation 84 propagating along the second optical path 82 both propagate through the window 70. In certain embodiments, the sensor 80 is wholly or at least partially within a region of the housing 12 at least partially bound, and substantially sealed by the window 70 against contaminants from entering the region from outside the region.

In certain embodiments, the apparatus 10 is adapted to cool the irradiated portion of the scalp or skull by removing heat from the scalp or skull so as to control, inhibit, prevent, minimize, or reduce temperature increases at the scalp or skull. Thus, by virtue of the apparatus 10 cooling the irradiated portion of the patient's scalp or skull, the temperature of the irradiated portion of the patient's scalp or skull is lower than it would otherwise be if the apparatus 10 did not cool the irradiated portion of the scalp or skull. For example, by cooling the irradiated portion of the patient's scalp or skull using the apparatus 10, the temperature of the irradiated portion of the patient's scalp or skull can be higher than the temperature of the portion of the patient's scalp or skull if it were not irradiated, but lower than the temperature of the portion of the patient's scalp or skull if it were irradiated but not cooled. Referring to FIGS. 4A and 4B, in certain embodiments, the apparatus 10 comprises a thermoelectric assembly 90 and a heat sink 100 in thermal communication with the thermoelectric assembly 90. In certain embodiments, the thermoelectric assembly 90 actively cools the patient's scalp or skull via the output optical assembly 20, thereby advantageously avoiding large temperature gradients at the patient's scalp or skull which would otherwise cause discomfort to the patient. In certain embodiments, the apparatus 10 further comprises one or more temperature sensors (e.g., thermocouples, thermistors) which generate electrical signals indicative of the temperature of the thermoelectric assembly 90.

In certain embodiments, the thermoelectric assembly 90 comprises at least one thermoelectric element 91 and a thermal conduit 92. The at least one thermoelectric element 91 of the thermoelectric assembly 90 is responsive to an electric current applied to the thermoelectric assembly 90 by cooling at least a first surface 93 of the thermoelectric assembly 90 and heating at least a second surface 94 of the thermoelectric assembly 90. The thermoelectric assembly 90 is configured to be releasably mechanically coupled to the output optical assembly 20 so as to have the first surface 93 in thermal communication with the output optical assembly 20. In certain embodiments, the first surface 93 comprises a surface of the thermal conduit 92 and the second surface 94 comprises a surface of the thermoelectric element 91.

Figure 9A:
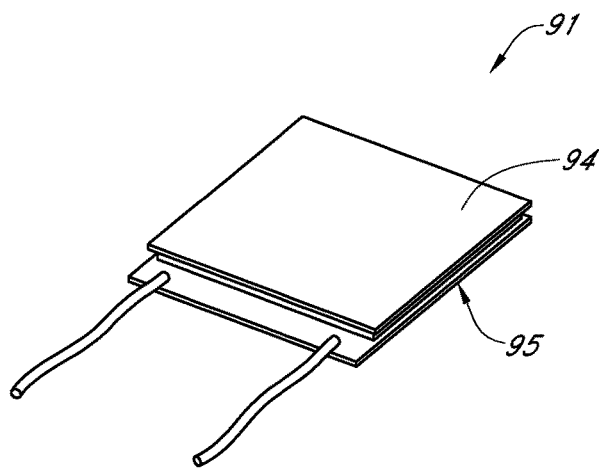
FIG. 9A schematically illustrates an example thermoelectric element and FIG. 9B schematically illustrates two views of an example thermal conduit in accordance with certain embodiments described herein.
Figure 9B:
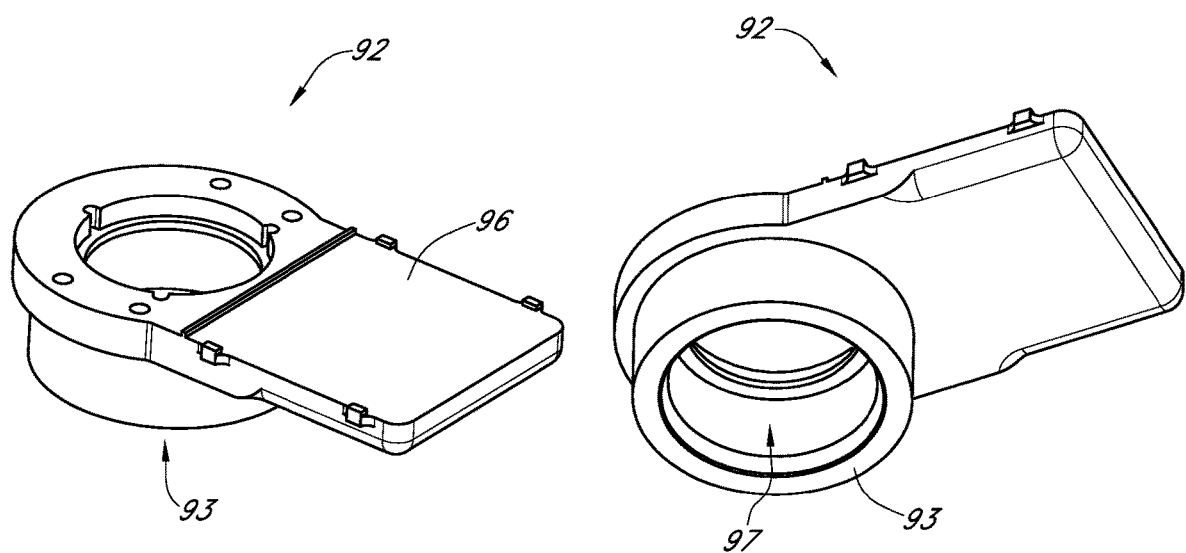
Figure 10A:
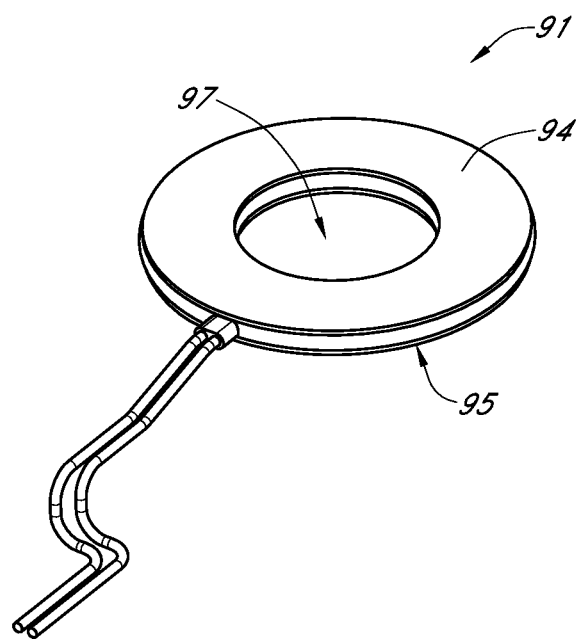
FIG. 10A schematically illustrates another example thermoelectric element and FIG. 10B schematically illustrates two views of another example thermal conduit in accordance with certain embodiments described herein.
Figure 10B:
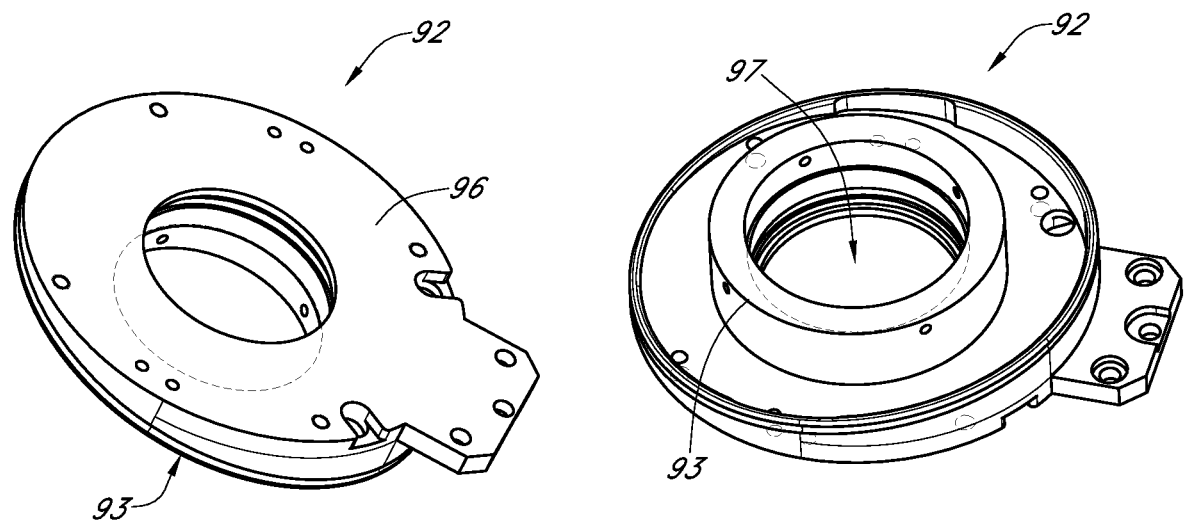

FIG. 9A schematically illustrates an example thermoelectric element 91 and FIG. 9B schematically illustrates two views of an example thermal conduit 92 in accordance with certain embodiments described herein. FIG. 10A schematically illustrates another example thermoelectric element 91 and FIG. 10B schematically illustrates two views of another example thermal conduit 92 in accordance with certain embodiments described herein. The thermoelectric element 91 has a surface 95 configured to be in thermal communication with a corresponding surface 96 of the thermal conduit 92 (e.g., by a thermally conductive adhesive). Upon application of an electric current to the thermoelectric element 91, the second surface 94 is heated and the surface 95 is cooled, thereby cooling the first surface 93. In certain such embodiments, the first surface 93 serves as at least one heat dissipating surface of the apparatus 10 configured to be in thermal communication with the at least one surface 26 of the thermal conduit 25 of the output optical assembly 20 (e.g., by contacting or mating so as to provide a thermally conductive connection between the thermoelectric assembly 26 and the output optical assembly 20). By having the thermally conductive output optical assembly 20 in thermal communication with the thermoelectric assembly 90, certain embodiments advantageously provide a conduit for heat conduction away from the treatment site (e.g., the skin). In certain embodiments, the output optical assembly 20 is pressed against the patient's skin and transfers heat away from the treatment site.

Examples of thermoelectric elements 91 compatible with certain embodiments described herein include, but are not limited to, DT12-6, $Q_{max}$=60 W, square thermoelectric element available from Marlow Industries of Dallas, Tex., and $Q_{max}$=45 W toroidal- or donut-shaped thermoelectric element from Ferrotec Corp. of Bedford, N.H. In certain embodiments, the thermoelectric element 91 removes heat from the output optical assembly 20 at a rate in a range of about 0.1 Watt to about 5 Watts or in a range of about 1 Watt to about 3 Watts. Example temperature controllers for operating the thermoelectric assembly 90 in accordance with certain embodiments described herein include, but are not limited to, MPT-5000 available from Wavelength Electronics, Inc. of Bozeman, Mont. Example materials for the thermal conduit 92 compatible with certain embodiments described herein include, but are not limited to, aluminum and copper. The thermal conduit 92 of certain embodiments has a thermal mass in a range of about 30 grams to about 70 grams, and has a thermal length between surface 93 and surface 96 in a range of about 0.5 inch to about 3.5 inches.

In certain embodiments, the thermoelectric assembly 90 generally surrounds a first region 97, wherein, during operation of the apparatus 10, light irradiating a portion of the patient's skin propagates through the first region 97. As shown in FIGS. 9B and 10B, in certain embodiments, the first region 97 comprises an aperture through the thermal conduit 92. As shown in FIG. 10B, the first region 97 in certain embodiments further comprises an aperture through the thermoelectric element 91. In certain embodiments, the thermoelectric assembly 90 comprises a plurality of thermoelectric elements 91 which are spaced from one another and are distributed to generally surround the first region 97. As used herein, the term "generally surrounds" has its broadest reasonable interpretation, including but not limited to, encircles or extends around at least one margin of the region, or being distributed around at least one margin of the region with one or more gaps along the at least one margin.

Figure 11A:
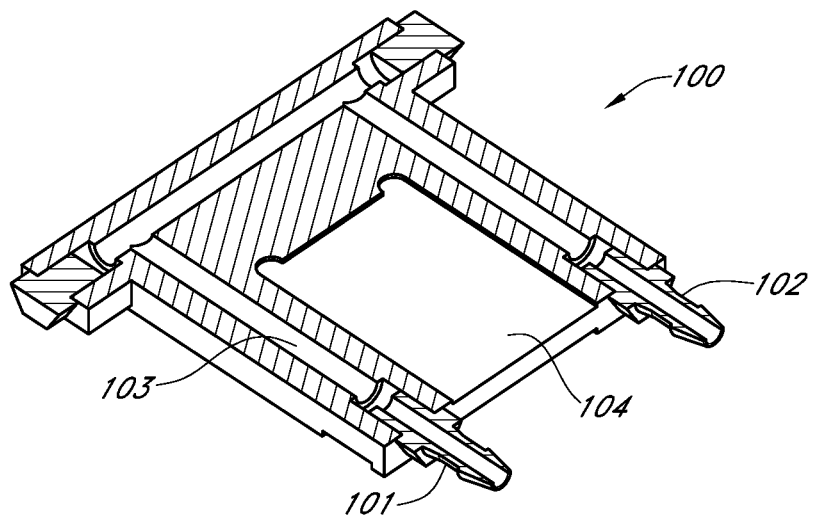
FIG. 11A schematically illustrates a cross-sectional view of an example heat sink and FIG. 11B schematically illustrates another example heat sink in accordance with certain embodiments described herein.
Figure 11B:
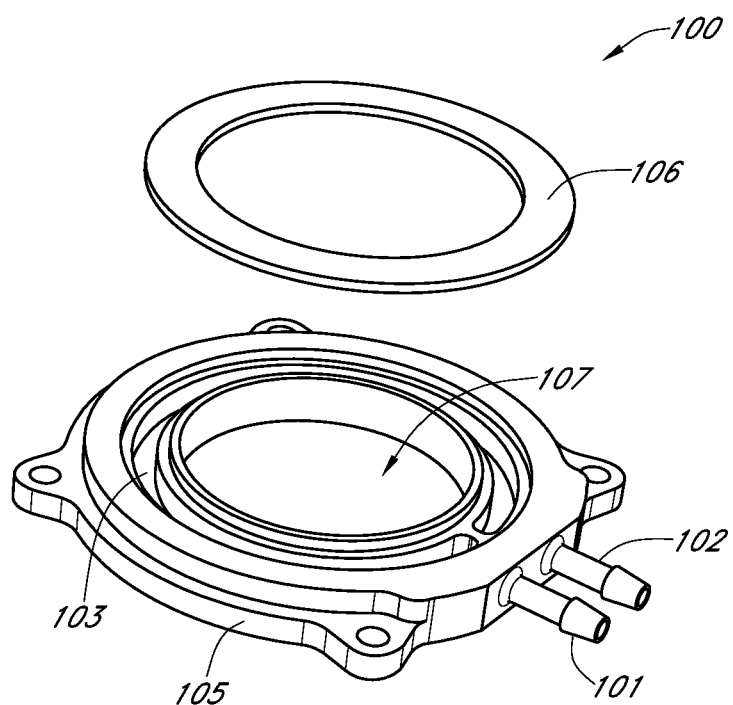

FIG. 11A schematically illustrates a cross-sectional view of an example heat sink 100 and FIG. 11B schematically illustrates another example heat sink 100 in accordance with certain embodiments described herein. The heat sink 100 comprises an inlet 101, an outlet 102, and a fluid conduit 103 in fluid communication with the inlet 101 and the outlet 102. The inlet 101 and the outlet 102 of certain embodiments comprise stainless steel barbs configured to be connected to tubes (e.g., using nylon or stainless steel hose barb locks, clamps, or crimps) which provide a coolant (e.g., water, air, glycerol) to flow through the fluid conduit 103 and to remove heat from the fluid conduit 103. In certain embodiments, the coolant is provided by a chiller or other heat transfer device which cools the coolant prior to its being supplied to the heat sink 100.

The example heat sink 100 of FIG. 11A is machined from an aluminum block and has a recess 104 in which the thermoelectric assembly 90 is placed to provide thermal communication between the heat sink 100 and the second surface 94 of the thermoelectric assembly 90. The example heat sink 100 of FIG. 11B comprises a first portion 105 and a second portion 106 which fit together to form the coolant conduit 103. In certain embodiments, a thermally conductive adhesive (e.g., EP1200 thermal adhesive available from Resinlab, LLC of Germantown, Wis., with a 0.005-inch stainless steel wire to set the bondline) is used to bond the thermoelectric assembly 90 and the heat sink 100 together in thermal communication with one another.

The output optical assembly 20 comprises a thermally conductive thermal conduit 25 having at least one surface 26 configured to be in thermal communication with the first surface of the thermoelectric assembly 90. As shown in FIGS. 2A and 2B, the thermal conduit 25 generally surrounds a second region 28. During operation of the apparatus 10, the light propagates through the first region 97, the second region 28, and the optical element 23. In certain embodiments, the heat sink 100 generally surrounds a third region 107, as schematically illustrated by FIG. 11B. During operation of the apparatus 10 in certain such embodiments, the light propagates through the third region 107, the first region 97, the second region 28, and the optical element 23.

Figure 12A:
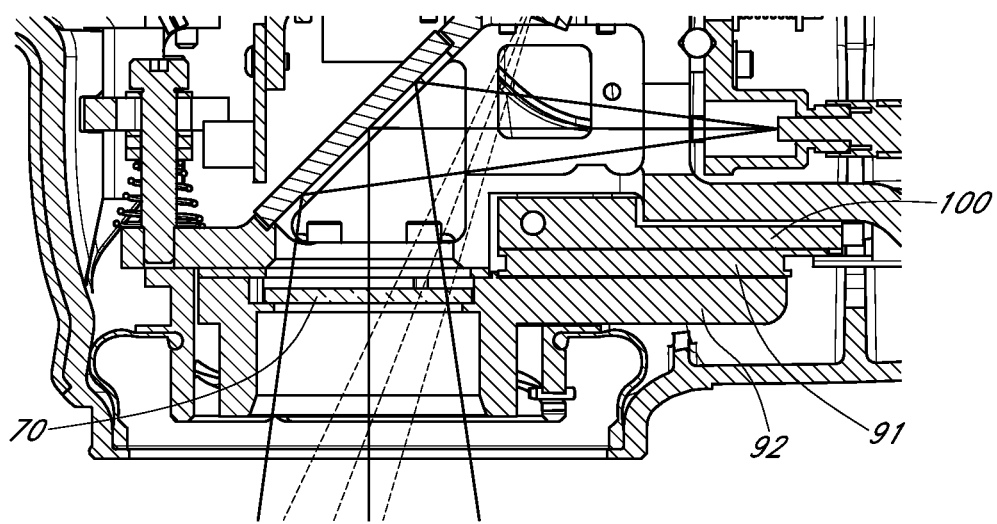
FIGS. 12A and 12B schematically illustrate two example configurations of the window with the thermoelectric assembly.
Figure 12B:
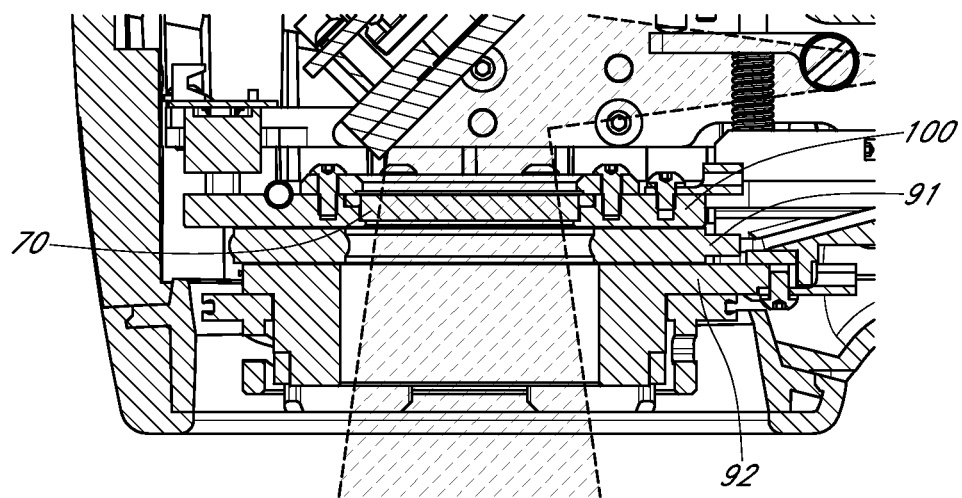

FIGS. 12A and 12B schematically illustrate two example configurations of the window 70 with the thermoelectric assembly 90. In certain embodiments, the window 70 is in thermal communication with at least a portion of the thermoelectric assembly 90 (e.g., bonded to a recess in the thermal conduit 92, as shown in FIG. 12A, using OP-29 adhesive available from Dymax Corp. of Torrington, Conn.). In certain embodiments, the window 70 is in thermal communication with at least a portion of the heat sink 100 (e.g., retained by an o-ring in the heat sink 100), as shown in FIG. 12B. In certain embodiments, the window 70 is not in thermal communication with either the thermoelectric assembly 90 or the heat sink 100.

Figure 13A:
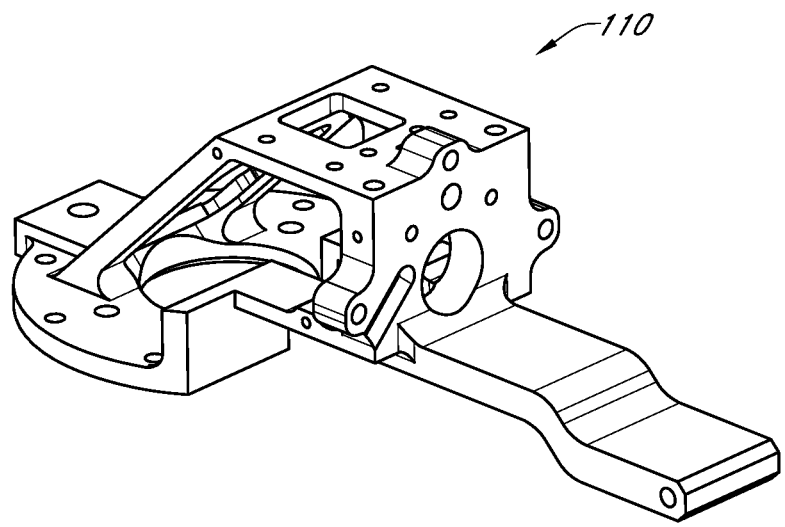
FIG. 13A schematically illustrates an example chassis for supporting the various components of the beam delivery apparatus within the housing in accordance with certain embodiments described herein.
Figure 13B:
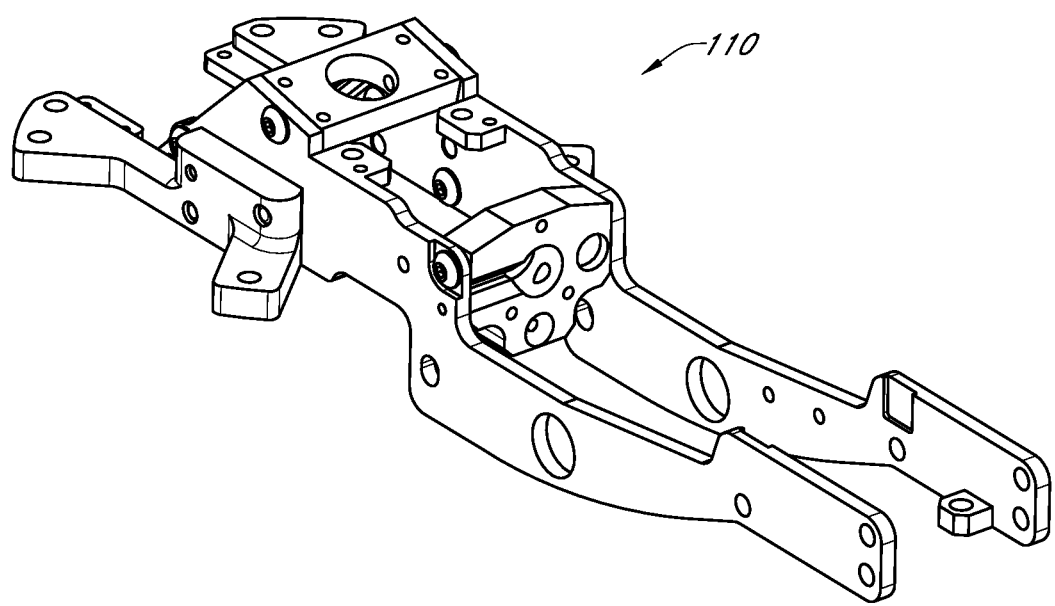
FIG. 13B schematically illustrates another example chassis in accordance with certain embodiments described herein.

FIG. 13A schematically illustrates an example chassis 110 for supporting the various components of the beam delivery apparatus 10 within the housing 12 in accordance with certain embodiments described herein. The chassis 110 of FIG. 13A comprises a single unitary or monolithic piece which is machined to provide various surfaces and holes used to mount the various components of the beam delivery apparatus 10. FIG. 13B schematically illustrates another example chassis 110 in accordance with certain embodiments described herein. The chassis 110 of FIG. 13B comprises a plurality of portions which are bolted or pinned together.

Figure 14A:
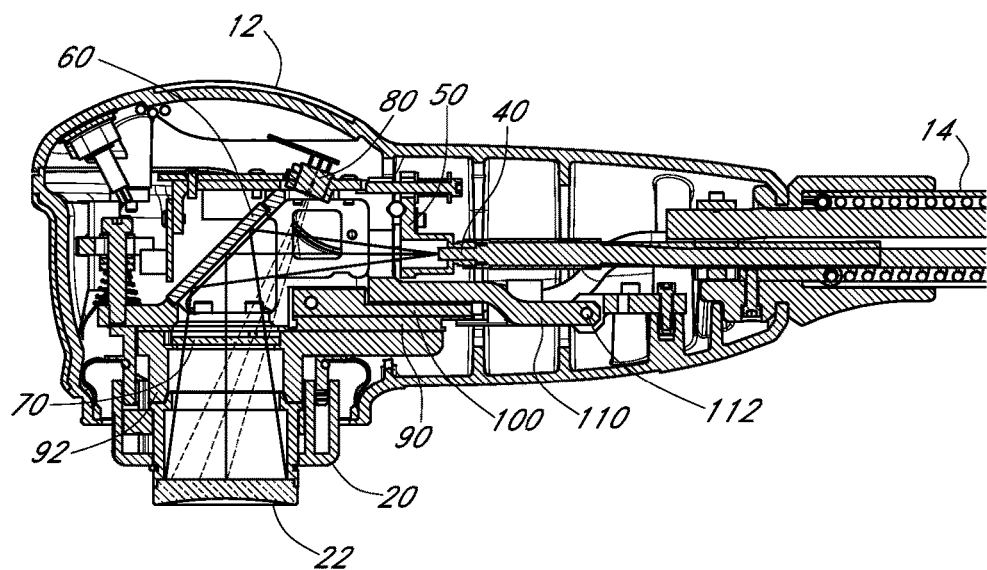
FIG. 14A schematically illustrates a cross-sectional view of an example configuration of the chassis and the housing in accordance with certain embodiments described herein.

FIG. 14A schematically illustrates a cross-sectional view of an example configuration of the chassis 110 and the housing 12 in accordance with certain embodiments described herein. The chassis 110 of certain embodiments is electrically connected to ground, while in certain other embodiments, the chassis 110 is electrically insulated from ground (e.g., floating). In certain embodiments, the chassis 110 is configured to move relative to the housing 12. For example, the chassis 110 and the housing 12 are mechanically coupled together by a pivot 112, as schematically illustrated by FIG. 14A. The optical fiber 40, fiber adjustment apparatus 50, mirror 60, window 70, sensor 80, and heat sink 100 are each mechanically coupled to the chassis 110. The output optical assembly 20 is also mechanically coupled to the chassis 110 via the thermoelectric assembly 90 and the heat sink 100.

For the configuration of FIG. 14A, the emission surface 22 of the output optical assembly 20 is placed in thermal communication (e.g., in contact) with the patient's scalp or skull by a user pressing the housing 12 towards the scalp or skull. The pivot 112 allows the chassis 110 to rotate about the pivot 112 relative to the housing 12 (e.g., by an angle between 1 and 2 degrees, or about 1.75 degrees) such that the emission surface 22 moves towards the housing 12 (e.g., by a distance of 0.05-0.3 inch, or about 0.1 inch). In certain such embodiments, this movement of the chassis 110, as well as of the fiber adjustment apparatus 50 and the optical fiber 40, results in a flexing of a portion of the optical fiber 40 (e.g., in proximity to the coupling between the housing 12 and the conduit 14).

Figure 14B:
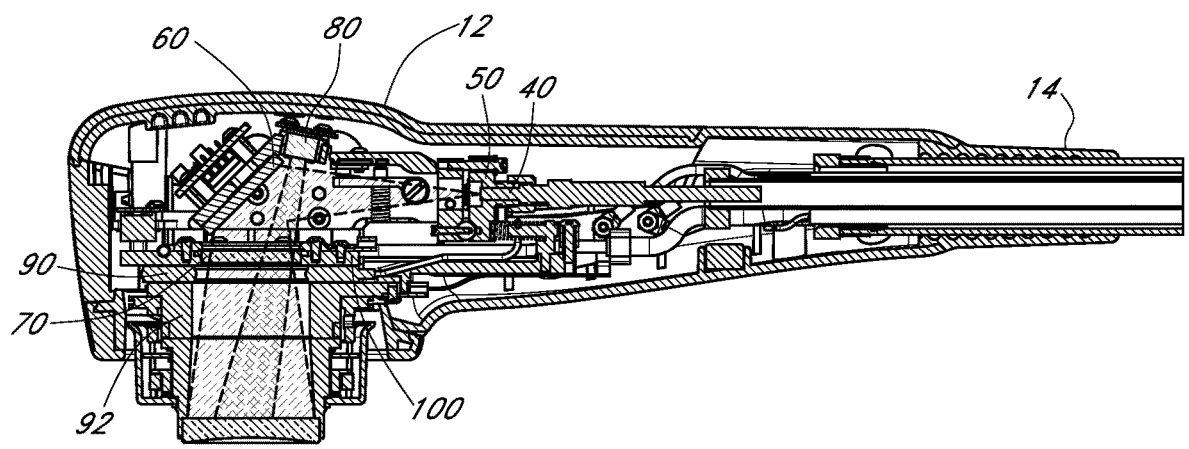
FIGS. 14B and 14C schematically illustrate another example configuration of the chassis and the housing in accordance with certain embodiments described herein.
Figure 14C:
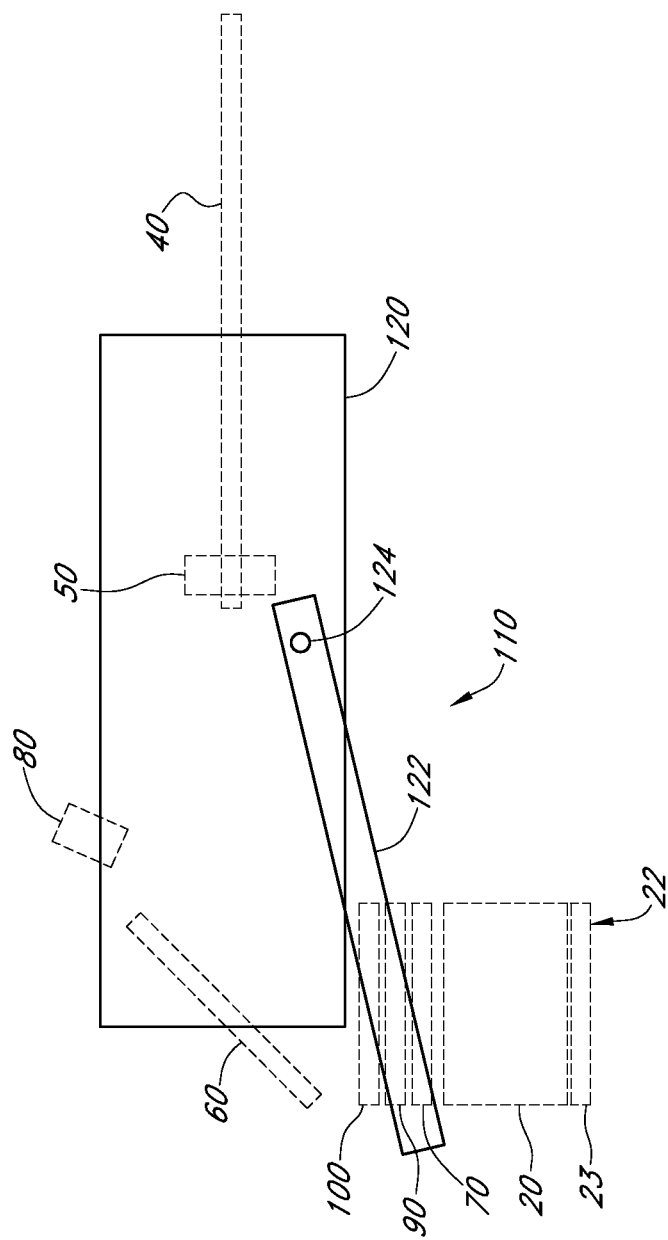

This flexing of the optical fiber 40 can be undesirable in certain circumstances, such as when the optical fiber 40 or its connection to the fiber adjustment apparatus 50 is fragile and prone to breakage or failure due to repeated flexing. FIGS. 14B and 14C schematically illustrate another example configuration of the chassis 110 and the housing 12 in accordance with certain embodiments described herein. The chassis 110 comprises a first chassis element 120 and a second chassis element 122 mechanically coupled to the first chassis element 120 such that the first chassis element 120 and the second chassis element 122 can move relative to one another. For example, in certain embodiments, the apparatus 10 further comprises a hinge 124 (e.g., a pivot or flexible portion) about which the first chassis element 120 and the second chassis element 122 are configured to deflect relative to one another.

In certain embodiments, the first chassis element 120 is mechanically coupled to the housing 12, and the optical fiber 40, fiber adjustment apparatus 50, mirror 60, and sensor 80 (each shown in dotted lines in FIG. 14C) are mechanically coupled to the first chassis element 120. The second chassis element 122 is mechanically coupled to the window 70, thermoelectric assembly 90, and the heat sink 100 (each shown in dotted lines in FIG. 14C). The output optical assembly 20 is also mechanically coupled to the second chassis element 122 via the thermoelectric assembly 90 and the heat sink 100. Thus, in certain such embodiments, a first portion of the apparatus 10 comprises the housing 12, first chassis element 120, optical fiber 40, fiber adjustment apparatus 50, mirror 60, and sensor 80, and a second portion of the apparatus 10 comprises the second chassis element 122, window 70, thermoelectric assembly 90, heat sink 100, and output optical assembly 20. The second portion is mechanically coupled to the first portion and is in optical communication with the first portion. The second portion is configured to be placed in thermal communication with the patient's skin such that the light from the first portion propagates through the second portion during operation of the apparatus 10. The first portion and the second portion are configured to move relative to one another in response to the second portion being placed in thermal communication with the patient's skin.

In certain embodiments, the second portion comprises the output optical assembly 20 and the first portion and the second portion are configured to deflect relative to one another by a non-zero angle. In certain embodiments, this deflection occurs upon the output optical assembly 20 applying a pressure to a portion of the patient's scalp sufficient to at least partially blanch the portion of the patient's scalp. In certain embodiments, this deflection occurs upon the output optical assembly 20 being placed in thermal communication with the patient's scalp or skull. In certain embodiments, the apparatus 10 further comprises a spring mechanically coupled to the first portion and the second portion. The spring provides a restoring force in response to movement of the first portion and the second portion relative to one another.

For the configuration of FIGS. 14B and 14C, the emission surface 22 of the output optical assembly 20 is placed in thermal communication (e.g., in contact) with the patient's scalp or skull by a user pressing the housing 12 towards the scalp or skull. The hinge 124 allows the second portion (e.g., including the second chassis element 122) to rotate about the hinge 124 relative to the first portion (e.g., including the first chassis element 120). This rotation can be by an angle between 1 and 3 degrees, or about 2.3 degrees) such that the emission surface 22 moves towards the housing 12 (e.g., by a distance of 0.05-0.3 inch, or about 0.08 inch). In certain such embodiments in which the first portion comprises the optical fiber 40, deflection of the first portion and the second portion relative to one another controls, inhibits, prevents, minimizes, or reduces flexing or movement of the optical fiber 40 (e.g., to control, inhibit, prevent, minimize, or reduce damage to the optical fiber 40). Thus, by virtue of the movement of the first and second portions relative to one another, the flexing, movement, or damage of the optical fiber 40 is lower than it would otherwise be if the first and second portions did not move relative to one another.

In certain embodiments, the relative movement of the output optical assembly 20 and the mirror 60 can result in the light beam 30 being at least partially occluded or "clipped" by the thermal conduit 25 of the output optical assembly 20. For example, for a light beam diameter of 30 millimeters, the light beam 30 is not clipped by the thermal conduit 25. For larger light beam diameters, the light beam 30 is partially occluded by the thermal conduit 25. For a light beam diameter of 31 millimeters, about 0.02% of the light beam area is occluded, and for 32 millimeters, about 1.56% of the light beam area is occluded, resulting in an estimated power loss of less than about 0.08%.

In certain embodiments, the apparatus 10 further comprises a sensor 130 configured to detect movement of the first portion and the second portion relative to one another (e.g., movement of the first chassis element 120 and the second chassis element 122 relative to one another). The sensor 130 is configured to transmit a signal to a controller configured to receive the signal and to control a light source in response to the signal, where the light source is configured to generate the light used by the apparatus 10 irradiate the patient's scalp or skull. In certain embodiments, the sensor 130 transmits the signal to the controller upon detecting that the movement between the first portion and the second portion is larger than a predetermined threshold value. In this way, the sensor 130 serves as a trigger switch which is used to trigger the apparatus 10 (e.g., providing the apparatus 10 with light upon the sensor 130 detecting the predetermined amount of movement between the first portion and the second portion indicative of the apparatus 10 being in a condition for use). The trigger switch of certain embodiments is actuated by pressing the output optical assembly 20 against a surface. The light source providing light to the apparatus 10 is responsive to the trigger switch by emitting light only when the trigger switch is actuated. Therefore, in certain such embodiments, to utilize the apparatus 10, the output optical assembly 20 is pressed against the patient's skin, such as described above.

Figure 15B:
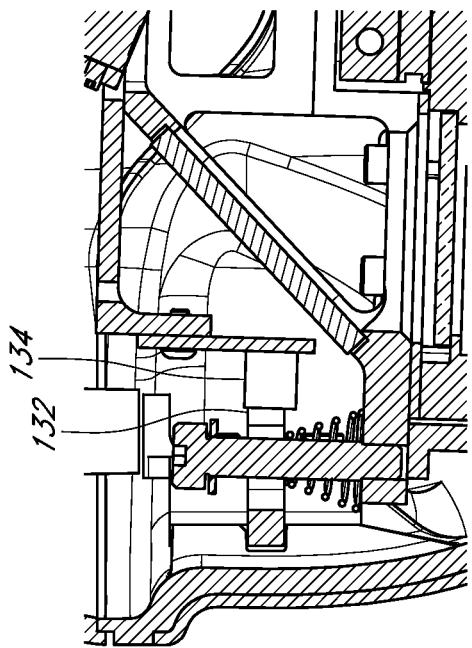
FIGS. 15A and 15B schematically illustrate two states of an example sensor in accordance with certain embodiments described herein.
Figure 15A:
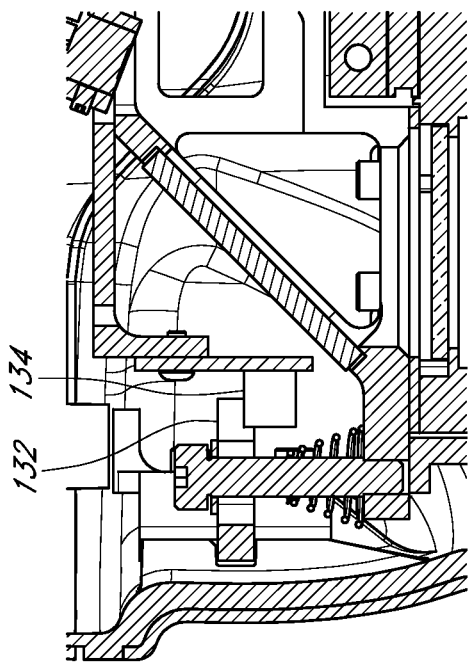

FIGS. 15A and 15B schematically illustrate two states of an example sensor 130 in accordance with certain embodiments described herein. The sensor 130 comprises at least one trigger flag 132 mechanically coupled to the first portion (e.g., the housing 12) and at least one optical switch 134 mechanically coupled to the second portion (e.g., the second chassis element 122). For example, the at least one optical switch 134 of certain embodiments comprises one, two, or more EE-SX-1035 optical switches available from Omron Electronics Components LLC of Schaumburg, Ill. In a first state, the trigger flag 132 is displaced away from a sensor light beam which is detected by the optical switch 134. Upon pressing the output optical assembly 20 in thermal communication with the patient's scalp or skull, the optical switch 134 moves relative to the trigger flag 132 (e.g., by a distance of about 0.07 inch) such that the trigger flag 132 intercepts the sensor light beam such that it is no longer detected by the optical switch 134. In response to this second state, the sensor 130 generates a corresponding signal. In certain other embodiments, the trigger flag 132 can be positioned to intercept the sensor light beam in the first state and to not intercept the sensor light beam in the second state.

FIGS. 15C and 15D schematically illustrate two states of another example sensor 130 in accordance with certain embodiments described herein. The sensor 130 comprises a reflective element 135 mechanically coupled to the first portion (e.g., the first chassis element 120) and at least one light source/detector pair 136 mechanically coupled to the second portion (e.g., the second chassis element 122). For example, the at least one light source/detector pair 136a, 136b of certain embodiments comprises one, two, or more QRE1113GR reflective sensors available from Fairchild Semiconductor Corp. of San Jose, Calif. In a first state, the reflective surface 135 is a first distance away from the light source/detector pair 136a, 136b such that a sensor light beam from the source 136a is reflected from the surface 135 but is not detected by the detector 136b. Upon pressing the output optical assembly 20 in thermal communication with the patient's scalp or skull, the reflective surface 135 moves (e.g., by a distance of about 0.04 inch) to be a second distance away from the light source/detector pair 136a, 136b such that the sensor light beam from the source 136a is reflected from the surface 135 and is detected by the detector 136b. In response to this second state, the sensor 130 generates a corresponding signal. In certain embodiments, the sensor 130 further comprises a shroud 137 configured to protect the detector 136b from stray light. In certain other embodiments, the reflective surface 135 can be positioned to reflect the sensor light beam to the detector 136b in the first state and to not reflect the sensor light beam to the detector 136b in the second state.

In certain embodiments, the apparatus 10 further comprises an adjustment mechanism configured to set the predetermined threshold value, to change the predetermined threshold value, or both. In certain such embodiments, the adjustment mechanism comprises a set screw which changes the relative positions of the two portions of the sensor 130 which move relative to one another. Certain embodiments further comprise a stop configured to limit a range of movement of the first portion and the second portion relative to one another.

Figure 16A:
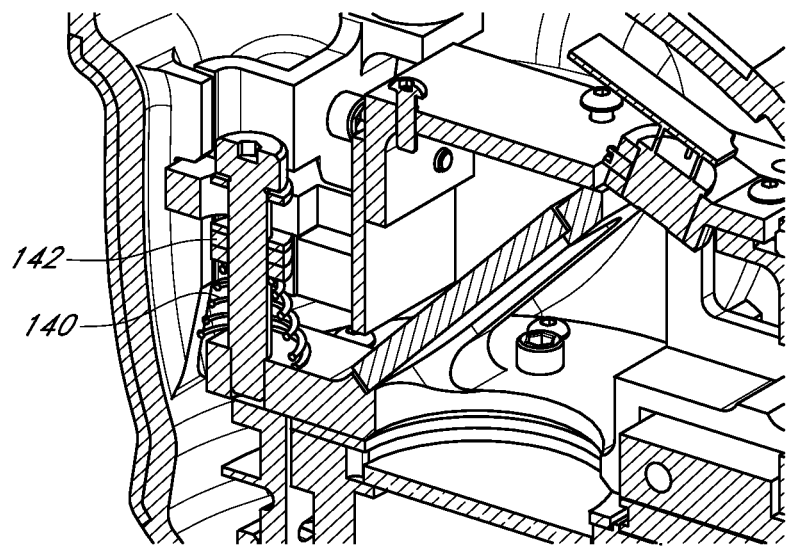
FIGS. 16A and 16B schematically illustrate two example configurations of the trigger force spring and trigger force adjustment mechanism in accordance with certain embodiments described herein.
Figure 16B:
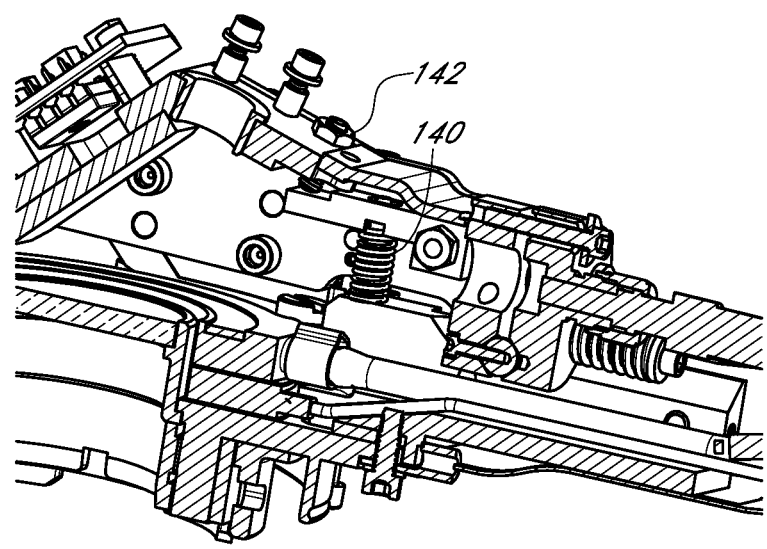

In certain embodiments, the apparatus 10 comprises a trigger force spring 140 and a trigger force adjustment mechanism 142. FIGS. 16A and 16B schematically illustrate two example configurations of the trigger force spring 140 and trigger force adjustment mechanism 142 in accordance with certain embodiments described herein. The trigger force spring 140 is mechanically coupled to the first portion (e.g., the first chassis element 120) and the second portion (e.g., the second chassis element 122) and provides a restoring force when the first portion and the second portion are moved relative to one another. The trigger force adjustment mechanism 142 of FIG. 16A comprises one or more shims (e.g., each shim providing about 100 grams of adjustment) placed between the spring 140 and at least one of the first portion and the second portion. The trigger force adjustment mechanism 142 of FIG. 16B comprises one, two, or more adjustment set screws. In either configuration, the trigger force adjustment mechanism 142 compresses the spring 140 to adjust the amount of force which will move the first and second portions relative to one another by a sufficient amount to trigger the apparatus 10. In certain embodiments, the trigger force adjustment mechanism 142 is set such that the apparatus 10 is triggered by a pressure applied to the emission surface 22 towards the housing 12 of at least 0.1 pound per square inch, at least one pound per square inch, or at least about two pounds per square inch.

Figure 17:
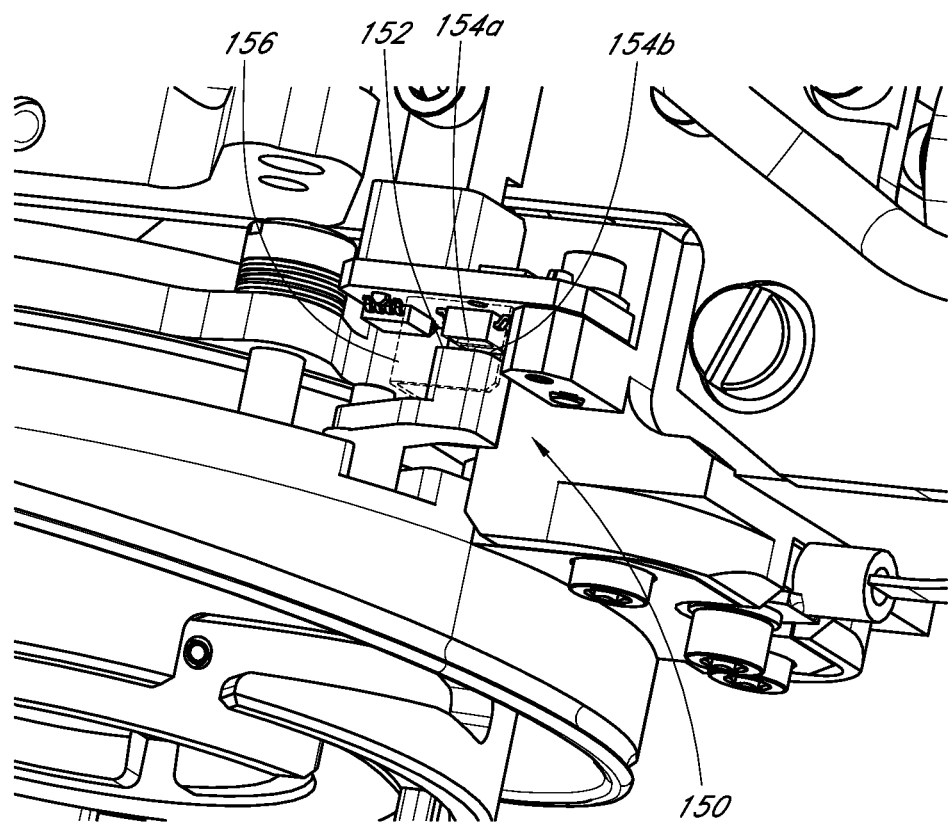
FIG. 17 schematically illustrates an example lens assembly sensor in accordance with certain embodiments described herein.

In certain embodiments, the apparatus 10 further comprises a lens assembly sensor 150 configured to detect the presence of the output optical assembly 20 mounted on the apparatus 10. FIG. 17 schematically illustrates an example lens assembly sensor 150 in accordance with certain embodiments described herein. For example, the lens assembly sensor 150 of certain embodiments comprises at least one reflective surface 152 and at least one light source/detector pair 154a, 154b (e.g., one, two, or more QRE1113GR reflective sensors available from Fairchild Semiconductor Corp. of San Jose, Calif.). The reflective surface 152 moves relative to the light source/detector pair 154a, 154b upon mounting the output optical assembly 20 to be in thermal communication with the thermal conduit 92. For example, when the output optical assembly 20 is mounted, the bayonet is pulled downward. In response to this movement, the sensor 150 generates a corresponding signal. In certain embodiments, the sensor 150 further comprises a shroud 156 configured to protect the detector 154b from stray light.

Control Circuit

Figure 18:
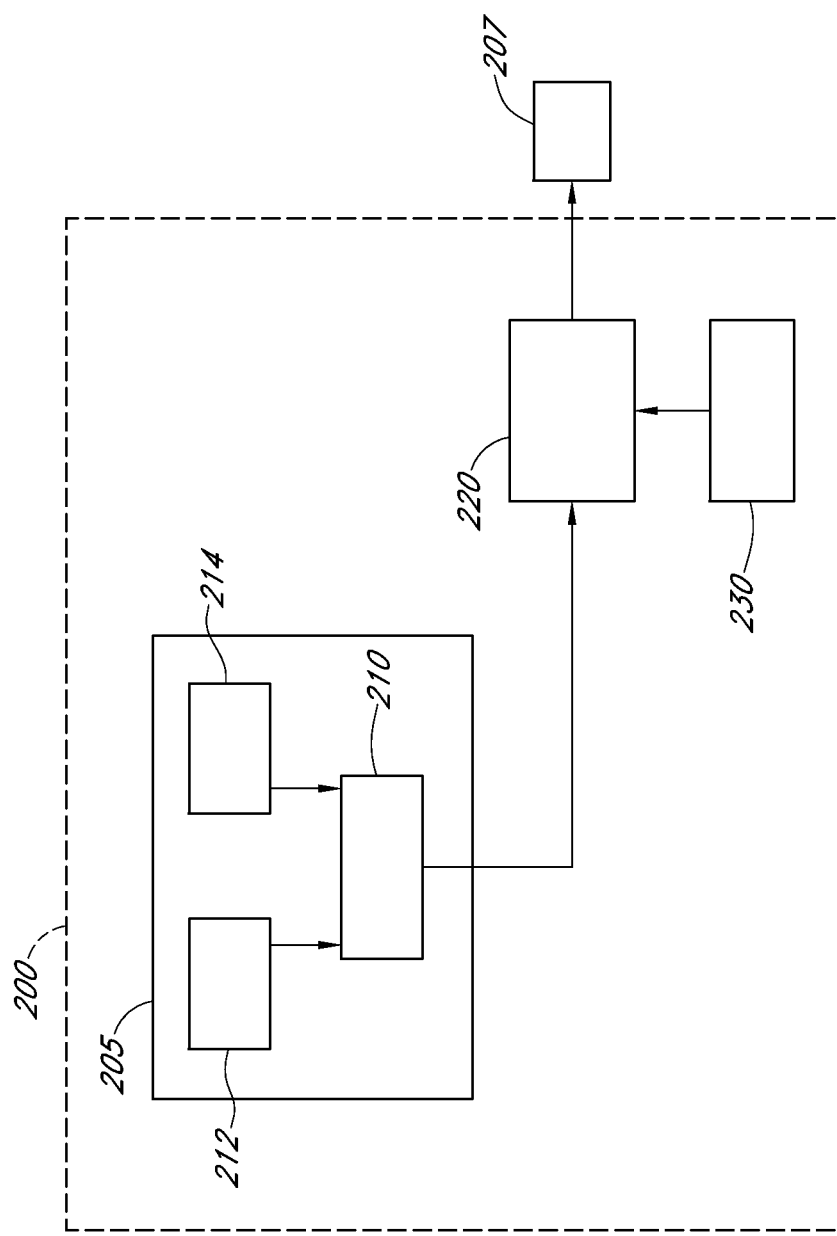
FIG. 18 is a block diagram of a control circuit comprising a programmable controller for controlling a light source according to embodiments described herein.

FIG. 18 is a block diagram of a control circuit 200 comprising a programmable controller 205 for controlling a light source 207 according to embodiments described herein. The control circuit 200 is configured to adjust the power of the light energy generated by the light source 207 such that the light emitted from the emission surface 22 generates a predetermined surface irradiance at the scalp or skull corresponding to a predetermined energy delivery profile, such as a predetermined subsurface irradiance, to the target area of the brain.

In certain embodiments, the programmable controller 205 comprises a logic circuit 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the applied light. Examples of timing intervals include, but are not limited to, total treatment times, pulsewidth times for pulses of applied light, and time intervals between pulses of applied light. In certain embodiments, the light source 207 can be selectively turned on and off to reduce the thermal load on the scalp or skull and to deliver a selected irradiance to particular areas of the brain.

The interface 214 of certain embodiments provides signals to the logic circuit 210 which the logic circuit 210 uses to control the applied light. The interface 214 can comprise a user interface or an interface to a sensor monitoring at least one parameter of the treatment. In certain such embodiments, the programmable controller 126 is responsive to signals from the sensor to preferably adjust the treatment parameters to optimize the measured response. The programmable controller 126 can thus provide closed-loop monitoring and adjustment of various treatment parameters to optimize the phototherapy. The signals provided by the interface 214 from a user are indicative of parameters that may include, but are not limited to, patient characteristics (e.g., skin type, fat percentage), selected applied irradiances, target time intervals, and irradiance/timing profiles for the applied light.

In certain embodiments, the logic circuit 210 is coupled to a light source driver 220. The light source driver 220 is coupled to a power supply 230, which in certain embodiments comprises a battery and in other embodiments comprises an alternating current source. The light source driver 220 is also coupled to the light source 207. The logic circuit 210 is responsive to the signal from the clock 212 and to user input from the user interface 214 to transmit a control signal to the light source driver 220. In response to the control signal from the logic circuit 210, the light source driver 220 adjust and controls the power applied to the light source. Other control circuits besides the control circuit 200 of FIG. 18 are compatible with embodiments described herein.

In certain embodiments, the logic circuit 110 is responsive to signals from a sensor monitoring at least one parameter of the treatment to control the applied light. For example, certain embodiments comprise a temperature sensor in thermal communication with the scalp or skull to provide information regarding the temperature of the scalp or skull to the logic circuit 210. In such embodiments, the logic circuit 210 is responsive to the information from the temperature sensor to transmit a control signal to the light source driver 220 so as to adjust the parameters of the applied light to maintain the scalp or skull temperature below a predetermined level. Other embodiments include example biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit 210. In certain such embodiments, the logic circuit 110 is responsive to signals from the sensors to preferably adjust the parameters of the applied light to optimize the measured response. The logic circuit 110 can thus provide closed-loop monitoring and adjustment of various parameters of the applied light to optimize the phototherapy.

Light Parameters

The various parameters of the light beam emitted from the emission surface 22 are advantageously selected to provide treatment while controlling, inhibiting, preventing, minimizing, or reducing injury or discomfort to the patient due to heating of the scalp or skull by the light. While discussed separately, these various parameters below can be combined with one another within the disclosed values in accordance with embodiments described herein.

Wavelength

In certain embodiments, light in the visible to near-infrared wavelength range is used to irradiate the patient's scalp or skull. In certain embodiments, the light is substantially monochromatic (i.e., light having one wavelength, or light having a narrow band of wavelengths). So that the amount of light transmitted to the brain is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In certain other embodiments, the light comprises one or more wavelengths between about 630 nanometers and about 1064 nanometers, between about 600 nanometers and about 980 nanometers, between about 780 nanometers and about 840 nanometers, between about 805 nanometers and about 820 nanometers, or includes wavelengths of about 785, 790, 795, 800, 805, 810, 815, 820, 825, or 830 nanometers. An intermediate wavelength in a range between approximately 730 nanometers and approximately 750 nanometers (e.g., about 739 nanometers) appears to be suitable for penetrating the skull, although other wavelengths are also suitable and may be used. In other embodiments, a plurality of wavelengths is used (e.g. applied concurrently or sequentially). In certain embodiments, the light has a wavelength distribution peaked at a peak wavelength and has a linewidth less than ±10 nanometers from the peak wavelength. In certain such embodiments, the light has a linewidth less than 4 nanometers, full width at 90% of energy. In certain embodiments, the center wavelength is (808±10) nanometers with a spectral linewidth less than 4 nanometers, full width at 90% of energy.

In certain embodiments, the light is generated by a light source comprising one or more laser diodes, which each provide coherent light. In embodiments in which the light from the light source is coherent, the emitted light may produce "speckling" due to coherent interference of the light. This speckling comprises intensity spikes which are created by wavefront interference effects and can occur in proximity to the target tissue being treated. For example, while the average irradiance or power density may be approximately 10 mW/cm$^2$, the power density of one such intensity spike in proximity to the brain tissue to be treated may be approximately 300 mW/cm$^2$. In certain embodiments, this increased power density due to speckling can improve the efficacy of treatments using coherent light over those using incoherent light for illumination of deeper tissues. In addition, the speckling can provide the increased power density without overheating the tissue being irradiated. The light within the speckle fields or islands containing these intensity spikes is polarized, and in certain embodiments, this polarized light provides enhanced efficacy beyond that for unpolarized light of the same intensity or irradiance.

In certain embodiments, the light source includes at least one continuously emitting GaAlAs laser diode having a wavelength of about 830 nanometers. In another embodiment, the light source comprises a laser source having a wavelength of about 808 nanometers. In still other embodiments, the light source includes at least one vertical cavity surface-emitting laser (VCSEL) diode. Other light sources compatible with embodiments described herein include, but are not limited to, light-emitting diodes (LEDs) and filtered lamps.

In certain embodiments, the one or more wavelengths are selected so as to work with one or more chromophores within the target tissue. Without being bound by theory or by a specific mechanism, it is believed that irradiation of chromophores increases the production of ATP in the target tissue and/or controls, inhibits, prevents, minimizes, or reduces apoptosis of the injured tissues, thereby producing beneficial effects, as described more fully below.

Some chromophores, such as water or hemoglobin, are ubiquitous and absorb light to such a degree that little or no penetration of light energy into a tissue occurs. For example, water absorbs light above approximately 1300 nanometers. Thus energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers.

Based on these broad assumptions, one can define an "IR window" into the body. Within the window, there are certain wavelengths that are more or less likely to penetrate. This discussion does not include wavelength dependent scattering effects of intervening tissues.

Figure 19A:
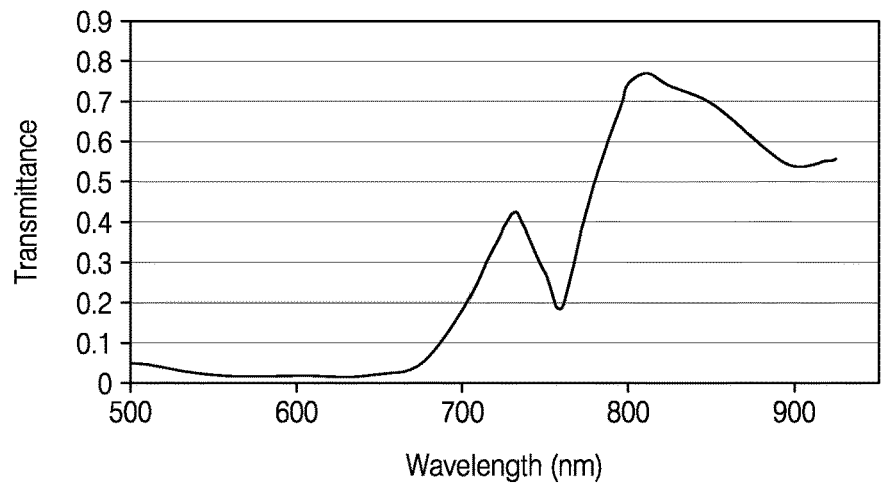
FIG. 19A is a graph of the transmittance of light through blood (in arbitrary units) as a function of wavelength.

The absorption/transmittance of various tissues have been directly measured to determine the utility of various wavelengths. FIG. 19A is a graph of the transmittance of light through blood (in arbitrary units) as a function of wavelength. Blood absorbs less in the region above 700 nanometers, and is particularly transparent at wavelengths above 780 nanometers. Wavelengths below 700 nanometers are heavily absorbed, and are not likely to be useful therapeutically (except for topical indications).

Figure 19B:
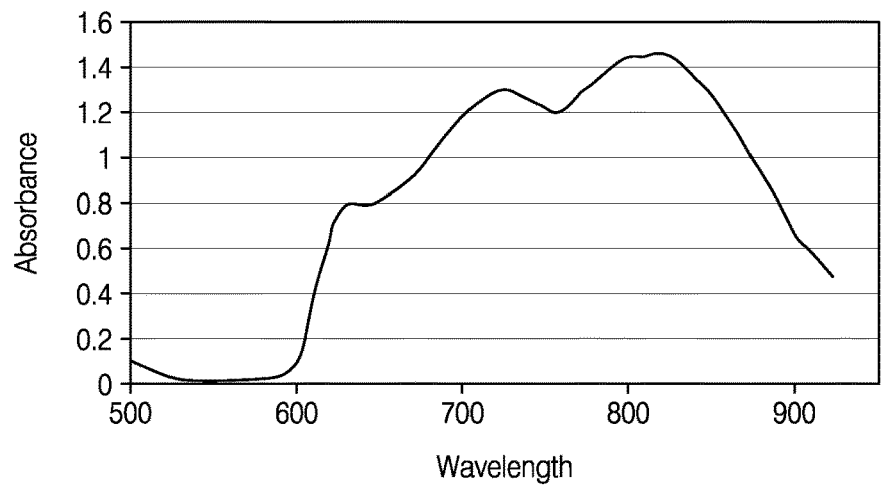
FIG. 19B is a graph of the absorption of light by brain tissue.

FIG. 19B is a graph of the absorption of light by brain tissue. Absorption in the brain is strong for wavelengths between 620 and 980 nanometers. This range is also where the copper centers in mitochondria absorb. The brain is particularly rich in mitochondria as it is a very active tissue metabolically (the brain accounts for 20% of blood flow and oxygen consumption). As such, the absorption of light in the 620 to 980 nanometer range is expected if a photostimulative effect is to take place.

Figure 19C:
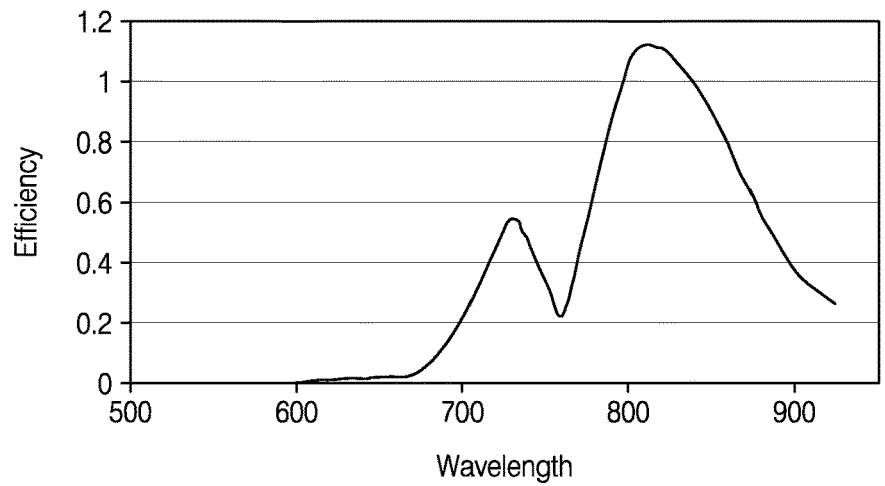
FIG. 19C shows the efficiency of energy delivery as a function of wavelength.

By combining FIGS. 19A and 19B, the efficiency of energy delivery as a function of wavelength can be calculated, as shown in FIG. 19C. Wavelengths between 780 and 880 nanometers are preferable (efficiency of 0.6 or greater) for targeting the brain. The peak efficiency is about 800 to 830 nanometers (efficiency of 1.0 or greater). These wavelengths are not absorbed by water or hemoglobin, and are likely to penetrate to the brain. Once these wavelengths reach the brain, they will be absorbed by the brain and converted to useful energy.

Figure 20:
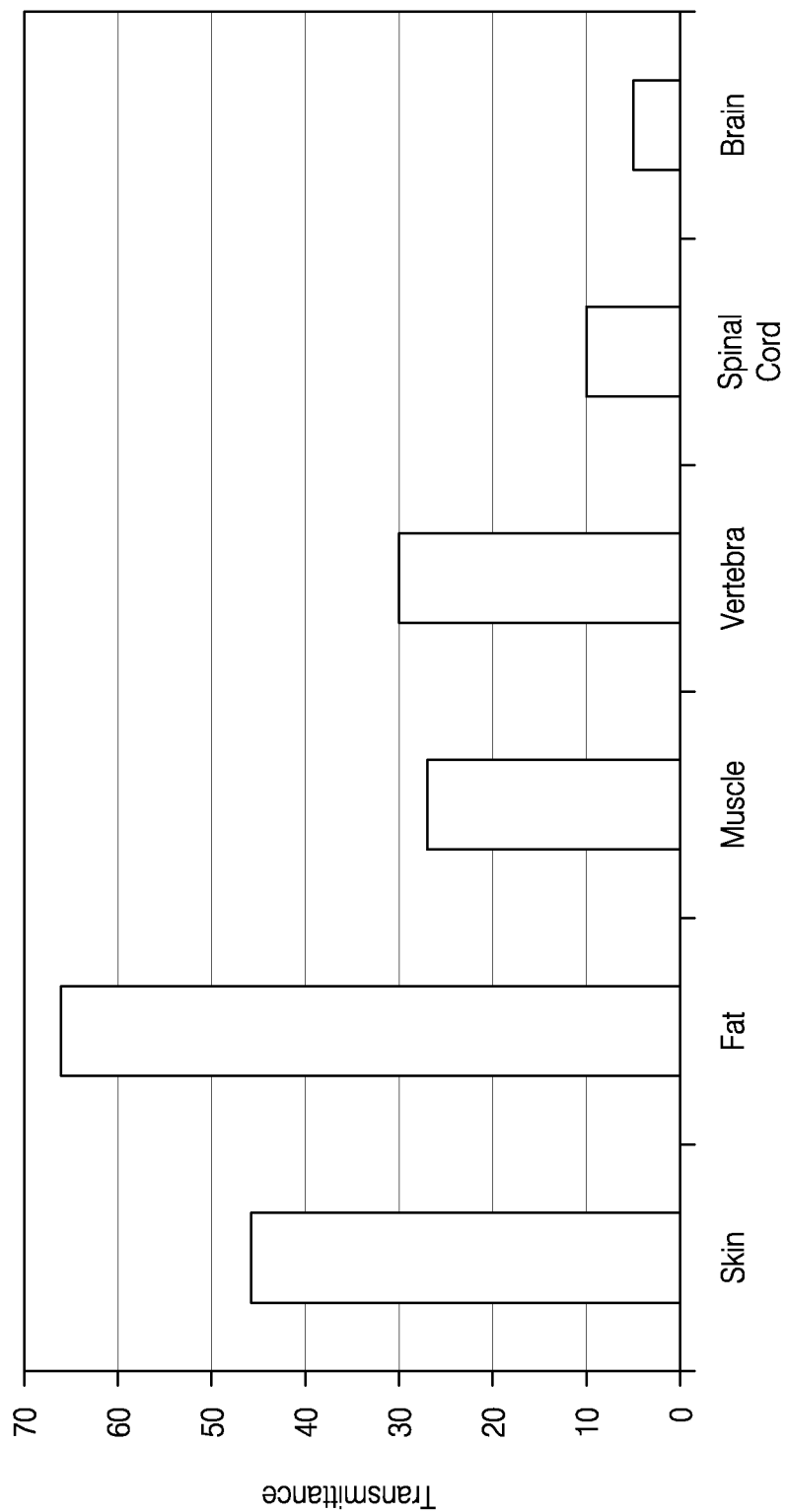
FIG. 20 shows measured absorption of 808 nanometer light through various rat tissues.

These effects have been directly demonstrated in rat tissues. The absorption of 808 nanometer light was measured through various rat tissues, as shown in FIG. 20. Soft tissues such as skin and fat absorb little light. Muscle, richer in mitochondria, absorbs more light. Even bone is fairly transparent. However, as noted above, brain tissue, as well as spinal cord tissue, absorb 808 nanometer light well.

Irradiance or Power Density

In certain embodiments, the light beam has a time-averaged irradiance or power density at the emission surface 22 of the output optical assembly 20 between about 10 mW/cm$^2$ to about 10 W/cm$^2$, between about 100 mW/cm$^2$ to about 1000 mW/cm$^2$, between about 500 mW/cm$^2$ to about 1 W/cm$^2$, or between about 650 mW/cm$^2$ to about 750 mW/cm$^2$ across the cross-sectional area of the light beam. For a pulsed light beam, the time-averaged irradiance is averaged over a time period long compared to the temporal pulse widths of the pulses (e.g., averaged over a fraction of a second longer than the temporal pulse width, over 1 second, or over multiple seconds). For a continuous-wave (CW) light beam with time-varying irradiance, the time-averaged irradiance can be an average of the instantaneous irradiance averaged over a time period longer than a characteristic time period of fluctuations of the light beam. In certain embodiments, a duty cycle in a range between 1% and 80%, between 10% and 30%, or about 20% can be used with a peak irradiance at the emission surface 22 of the output optical assembly 20 between about 12.5 mW/cm$^2$ to about 1000 W/cm$^2$, between about 50 mW/cm$^2$ to about 50 W/cm$^2$, between about 500 mW/cm$^2$ to about 5000 mW/cm$^2$, between about 2500 mW/cm$^2$ to about 5 W/cm$^2$, or between about 3.25 W/cm$^2$ to about 3.75 W/cm$^2$ across the cross-sectional area of the light beam. In certain embodiments, the pulsed light beam has an energy or fluence (e.g., peak irradiance multiplied by the temporal pulsewidth) at the emission surface 22 of the output optical assembly 20 between about 12.5 µJ/cm$^2$ to about 1 J/cm$^2$, between about 50 µJ/cm$^2$ to about 50 mJ/cm$^2$, between about 500 µJ/cm$^2$ to about 5 mJ/cm$^2$, between about 2.5 mJ/cm$^2$ to about 5 mJ/cm$^2$, or between about 3.25 mJ/cm$^2$ to about 3.75 mJ/cm$^2$.

The cross-sectional area of the light beam of certain embodiments (e.g., multimode beams) can be approximated using an approximation of the beam intensity distribution. For example, as described more fully below, measurements of the beam intensity distribution can be approximated by a Gaussian (1/e$^2$ measurements) or by a "top hat" distribution and a selected perimeter of the beam intensity distribution can be used to define a bound of the area of the light beam. In certain embodiments, the irradiance at the emission surface 22 is selected to provide the desired irradiances at the subdermal target tissue. The irradiance of the light beam is preferably controllably variable so that the emitted light energy can be adjusted to provide a selected irradiance at the subdermal tissue being treated. In certain embodiments, the light beam emitted from the emission surface 22 is continuous with a total radiant power in a range of about 4 Watts to about 6 Watts. In certain embodiments, the radiant power of the light beam is 5 Watts±20% (CW). In certain embodiments, the peak power for pulsed light is in a range of about 10 Watts to about 30 Watts (e.g., 20 Watts). In certain embodiments, the peak power for pulsed light multiplied by the duty cycle of the pulsed light yields an average radiant power in a range of about 4 Watts to about 6 Watts (e.g., 5 Watts).

In certain embodiments, the time-averaged irradiance at the subdermal target tissue (e.g., at a depth of approximately 2 centimeters below the dura) is at least about 0.01 mW/cm$^2$ and up to about 1 W/cm$^2$ at the level of the tissue. In various embodiments, the time-averaged subsurface irradiance at the target tissue is at least about 0.01, 0.05, 0.1, 0.5, 1, 5, 10, 15, 20, 30, 40, 50, 60, 70, 80, or 90 mW/cm$^2$, depending on the desired clinical performance. In certain embodiments, the time-averaged subsurface irradiance at the target tissue is about 0.01 mW/cm$^2$ to about 100 mW/cm$^2$, about 0.01 mW/cm$^2$ to about 50 mW/cm$^2$, about 2 mW/cm$^2$ to about 20 mW/cm$^2$, or about 5 mW/cm$^2$ to about 25 mW/cm$^2$. In certain embodiments, a duty cycle in a range between 1% and 80%, between 10% and 30%, or about 20% can be used with a peak irradiance at the target tissue of 0.05 mW/cm$^2$ to about 500 mW/cm$^2$, about 0.05 mW/cm$^2$ to about 250 mW/cm$^2$, about 10 mW/cm$^2$ to about 100 mW/cm$^2$, or about 25 mW/cm$^2$ to about 125 mW/cm$^2$.

In certain embodiments, the irradiance of the light beam is selected to provide a predetermined irradiance at the subdermal target tissue (e.g., at a depth of approximately 2 centimeters from the dura). The selection of the appropriate irradiance of the light beam emitted from the emission surface to use to achieve a desired subdermal irradiance preferably includes consideration of scattering by intervening tissue. Further information regarding the scattering of light by tissue is provided by U.S. Pat. No. 7,303,578, which is incorporated in its entirety by reference herein, and V. Tuchin in "Tissue Optics: Light Scattering Methods and Instruments for Medical Diagnosis," SPIE Press (2000), Bellingham, Wash., pp. 3-11, which is incorporated in its entirety by reference herein.

Phototherapy for the treatment of neurologic conditions (e.g., ischemic stroke, Alzheimer's Disease, Parkinson's Disease, depression, or TBI) is based in part on the discovery that irradiance or power density (i.e., power per unit area or number of photons per unit area per unit time) and energy density (i.e., energy per unit area or number of photons per unit area) of the light energy applied to tissue appear to be significant factors in determining the relative efficacy of low level phototherapy. This discovery is particularly applicable with respect to treating and saving surviving but endangered neurons in a zone of danger surrounding the primary injury. Certain embodiments described herein are based at least in part on the finding that, given a selected wavelength of light energy, it is the irradiance and/or the energy density of the light delivered to tissue (as opposed to the total power or total energy delivered to the tissue) that appears to be important factors in determining the relative efficacy of phototherapy.

Without being bound by theory or by a specific mechanism, it is believed that light energy delivered within a certain range of irradiances and energy densities provides the desired biostimulative effect on the intracellular environment, such that proper function is returned to previously nonfunctioning or poorly functioning mitochondria in at-risk neurons. The biostimulative effect may include interactions with chromophores within the target tissue, which facilitate production of ATP and/or controls, inhibits, prevents, minimizes, or reduces apoptosis of the injured cells which have experienced decreased blood flow (e.g., due to the stroke or TBI). Because strokes and TBI correspond to interruptions of blood flow to portions of the brain, it is thought that any effects of increasing blood flow by phototherapy are of less importance in the efficacy of phototherapy for stroke or TBI victims. Further information regarding the role of irradiance and exposure time is described by Hans H. F. I. van Breugel and P. R. Dop Bär in "Power Density and Exposure Time of He—Ne Laser Irradiation Are More Important Than Total Energy Dose in Photo-Biomodulation of Human Fibroblasts In Vitro," Lasers in Surgery and Medicine, Volume 12, pp. 528-537 (1992), which is incorporated in its entirety by reference herein. In addition, the significance of the irradiance used in phototherapy with regard to the devices and methods used in phototherapy of brain tissue, are described more fully in U.S. Pat. No. 7,303,578 and in U.S. Patent Appl. Publ. Nos. 2005/0107851 A1, 2007/0179570 A1, and 2007/0179571 A1, each of which is incorporated in its entirety by reference herein. While these previous discussions of irradiance were primarily in conjunction with phototherapy of stroke, they apply as well to phototherapy of TBI. For example, in certain embodiments, to obtain a desired average power density at the brain for treating TBI, higher total power at the scalp or skull can be used in conjunction with a larger spot size at the scalp or skull. Thus, by increasing the spot size at the scalp or skull, a desired average power density at the brain can be achieved with lower power densities at the scalp or skull which can reduce the possibility of overheating the scalp, skull, or brain.

In certain embodiments, delivering the neuroprotective amount of light energy includes selecting a surface irradiance of the light energy at the scalp or skull corresponding to the predetermined irradiance at the target area of the brain. As described above, light propagating through tissue is scattered and absorbed by the tissue. Calculations of the irradiance to be applied to the scalp or skull so as to deliver a predetermined irradiance to the selected target area of the brain preferably take into account the attenuation of the light energy as it propagates through the skin and other tissues, such as bone and brain tissue. Factors known to affect the attenuation of light propagating to the brain from the scalp or skull include, but are not limited to, skin pigmentation, the presence, type, and color of hair over the area to be treated, amount of fat tissue, the presence of bruised tissue, skull thickness, patient's age and gender, and the location of the target area of the brain, particularly the depth of the area relative to the surface of the scalp or skull. (For a general discussion of the absorption of light by melanins in the body, see, e.g., "Optical Absorption Spectra of Melanins—a Comparison of Theoretical and Experimental Results," accelrys.com/references/case-studies/melanins_partII.pdf) The higher the level of skin pigmentation, the higher the irradiance applied to the scalp to deliver a predetermined irradiance of light energy to a subsurface site of the brain. The target area of the patient's brain can be previously identified such as by using standard medical imaging techniques.

The irradiance selected to be applied to the target area of the patient's brain depends on a number of factors, including, but not limited to, the wavelength of the applied light, the type of CVA (ischemic or hemorrhagic), and the patient's clinical condition, including the extent of the affected brain area. The irradiance or power density of light energy to be delivered to the target area of the patient's brain may also be adjusted to be combined with any other therapeutic agent or agents, especially pharmaceutical neuroprotective agents, to achieve the desired biological effect. In such embodiments, the selected irradiance can also depend on the additional therapeutic agent or agents chosen.

Figure 21A:
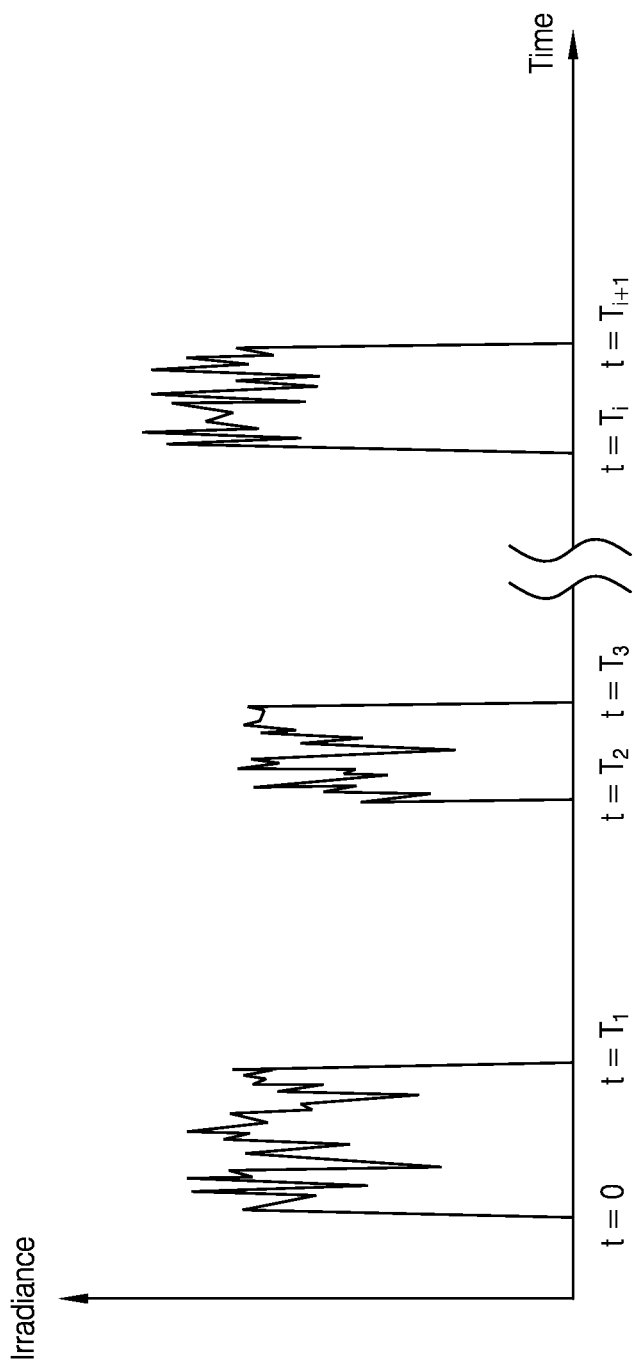
FIGS. 21A-21D schematically illustrate example pulses in accordance with certain embodiments described herein.

Temporal Pulsewidth, Temporal Pulseshape, Duty Cycle, Repetition Rate, and Irradiance per Pulse FIG. 21A schematically illustrates a generalized temporal profile of a pulsed light beam in accordance with certain embodiments described herein. The temporal profile comprises a plurality of pulses ($P_1, P_2, \ldots, P_i$), each pulse having a temporal pulsewidth during which the instantaneous intensity or irradiance I(t) of the pulse is substantially non-zero. For example, for the pulsed light beam of FIG. 21A, pulse $P_i$ has a temporal pulsewidth from time t=0 to time t=$T_i$, pulse $P_2$ has a temporal pulsewidth from time t=$T_2$ to time t=$T_3$, and pulse $P_i$ has a temporal pulsewidth from time t=$T_i$ to time t=$T_{i+}$. The temporal pulsewidth can also be referred to as the "pulse ON time." The pulses are temporally spaced from one another by periods of time during which the intensity or irradiance of the beam is substantially zero. For example, pulse $P_1$ is spaced in time from pulse $P_2$ by a time t=$T_2$-$T_1$. The time between pulses can also be referred to as the "pulse OFF time." In certain embodiments, the pulse ON times of the pulses are substantially equal to one another, while in certain other embodiments, the pulse ON times differ from one another. In certain embodiments, the pulse OFF times between the pulses are substantially equal to one another, while in certain other embodiments, the pulse OFF times between the pulses differ from one another. As used herein, the term "duty cycle" has its broadest reasonable interpretation, including but not limited to, the pulse ON time divided by the sum of the pulse ON time and the pulse OFF time. For a pulsed light beam, the duty cycle is less than one. The values of the duty cycle and the temporal pulsewidth fully define the repetition rate of the pulsed light beam.

Figure 21B:
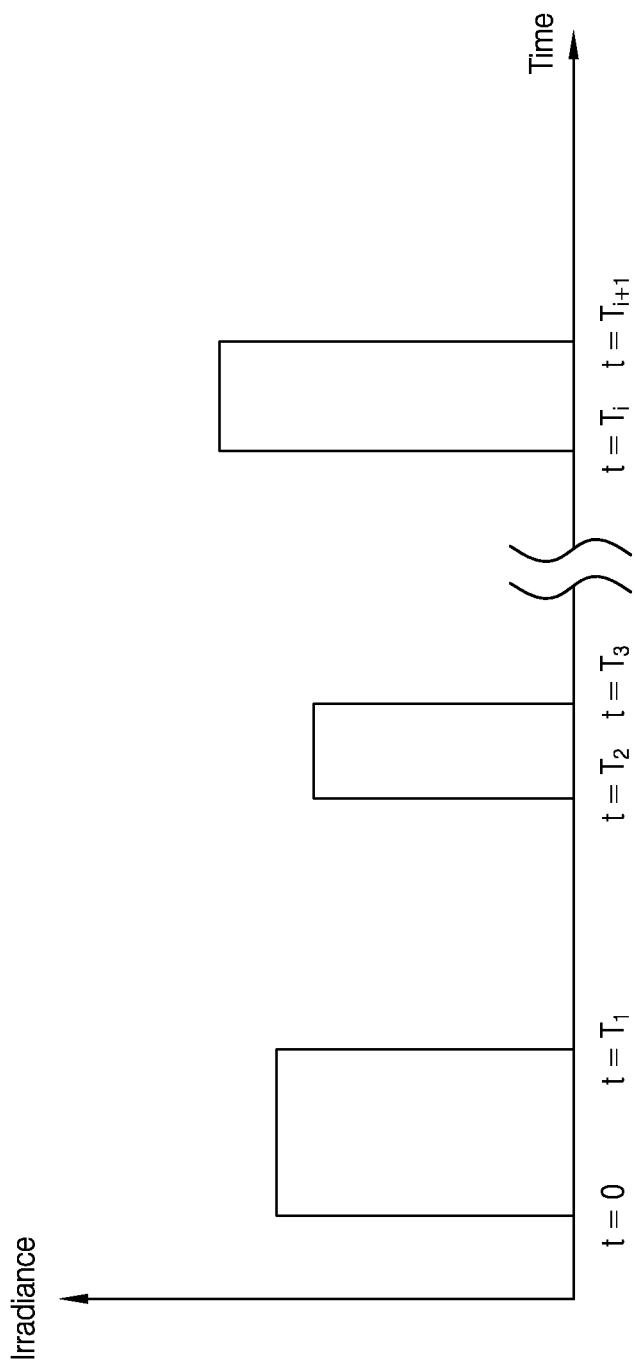
Figure 21C:
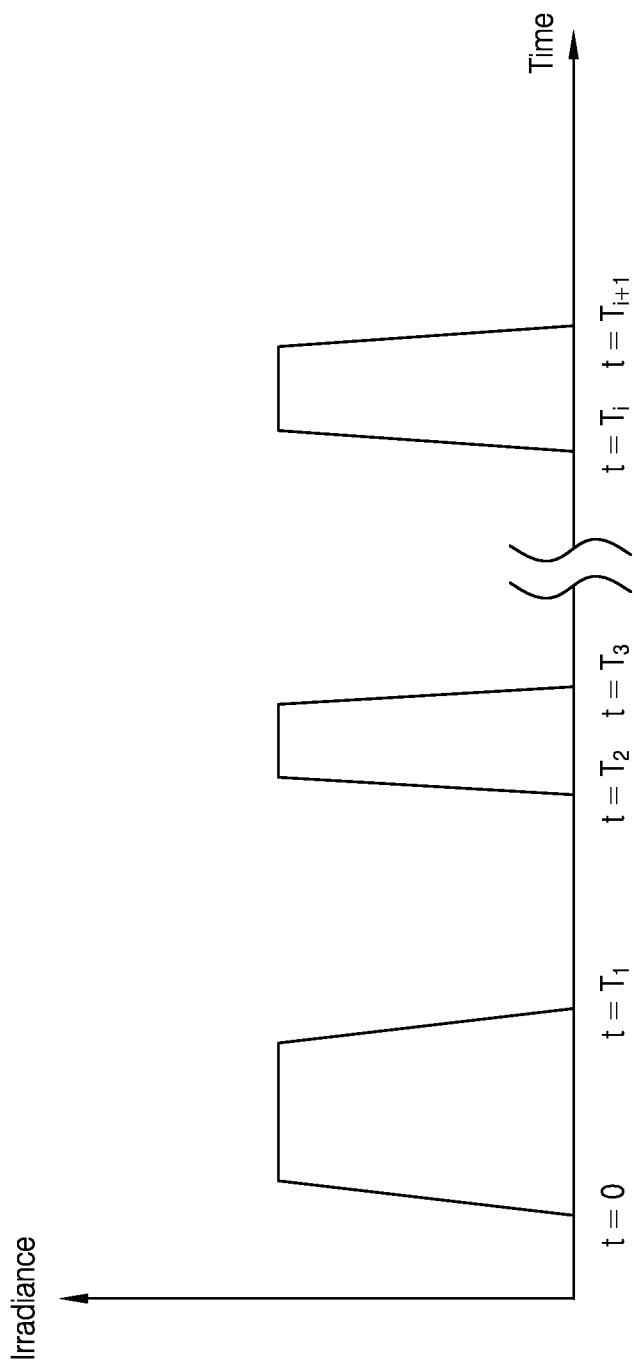

Each of the pulses can have a temporal pulseshape which describes the instantaneous intensity or irradiance of the pulse I(t) as a function of time. For example, as shown in FIG. 21A, the temporal pulseshapes of the pulsed light beam are irregular, and are not the same among the various pulses. In certain embodiments, the temporal pulseshapes of the pulsed light beam are substantially the same among the various pulses. For example, as schematically shown in FIG. 21B, the pulses can have a square temporal pulseshape, with each pulse having a substantially constant instantaneous irradiance over the pulse ON time. In certain embodiments, the peak irradiances of the pulses differ from one another (see, e.g., FIGS. 21A and 21B), while in certain other embodiments, the peak irradiances of the pulses are substantially equal to one another (see, e.g., FIGS. 21C and 21D). Various other temporal pulseshapes (e.g., triangular, trapezoidal) are also compatible with certain embodiments described herein. FIG. 21C schematically illustrates a plurality of trapezoidal pulses in which each pulse has a rise time (e.g., corresponding to the time between an instantaneous irradiance of zero and a peak irradiance of the pulse) and a fall time (e.g., corresponding to the time between the peak irradiance of the pulse and an instantaneous irradiance of zero). In certain embodiments, the rise time and the fall time can be expressed relative to a specified fraction of the peak irradiance of the pulse (e.g., time to rise/fall to 50% of the peak irradiance of the pulse).

As used herein, the term "peak irradiance" of a pulse $P_i$ has its broadest reasonable interpretation, including but not limited to, the maximum value of the instantaneous irradiance I(t) during the temporal pulsewidth of the pulse. In certain embodiments, the instantaneous irradiance is changing during the temporal pulsewidth of the pulse (see, e.g., FIGS. 21A and 21C), while in certain other embodiments, the instantaneous irradiance is substantially constant during the temporal pulsewidth of the pulse (see, e.g., FIGS. 21B and 21D).

As used herein, the term "pulse irradiance" $I_{P_i}$ of a pulse $P_i$ has its broadest reasonable interpretation, including but not limited to, the integral of the instantaneous irradiance I(t) of the pulse $P_i$ over the temporal pulsewidth of the pulse:

$$I_{P_i} = \int_{T_i}^{T_{i+1}} I(t) \cdot dt / (T_{i+1} - T_i).$$

As used herein, the term "total irradiance" $I_{TOTAL}$ has its broadest reasonable interpretation, including but not limited to, the sum of the pulse irradiances of the pulses:

$$I_{TOTAL} = \sum_{i=0}^{N} I_{P_i}.$$

As used herein, the term "time-averaged irradiance" $I_{AVE}$ has its broadest reasonable interpretation, including but not limited to, the integral of the instantaneous irradiance I(t) over a period of time T large compared to the temporal pulsewidths of the pulses:

$$I_{AVE} = \int_0^T I(t) \cdot dt / T.$$

The integral $$\int_0^T I(t) \cdot dt$$

provides the energy of the pulsed light beam.

For example, for a plurality of square pulses with different pulse irradiances $I_{P_j}$ and different temporal pulsewidths $\alpha T_i$, the time-averaged irradiance over a time T equals $$I_{AVE} = \frac{1}{T} \sum_i I_{P_i} \cdot \Delta T_i.$$

Figure 21D:
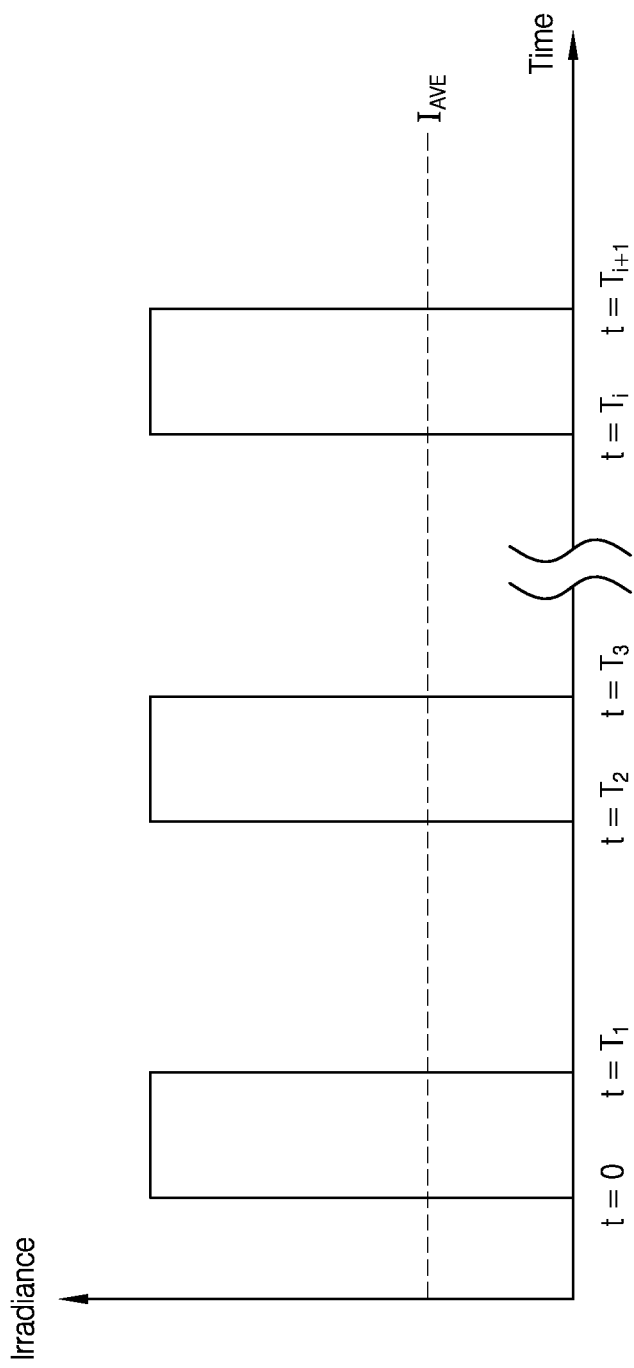

For another example, for a plurality of square pulses with equal pulse irradiances $I_P$, with equal temporal pulsewidths, and equal pulse OFF times (having a duty cycle D), the time-averaged irradiance equals $I_{AVE}=I_P \cdot D$. For example, as shown in FIG. 21D, the time-averaged irradiance (shown as a dashed line) is less than the pulse irradiance of the pulses.

The pulse irradiances and the duty cycle can be selected to provide a predetermined time-averaged irradiance. In certain embodiments in which the time-averaged irradiance is equal to the irradiance of a continuous-wave (CW) light beam, the pulsed light beam and the CW light beam have the same number of photons or flux as one another. For example, a pulsed light beam with a pulse irradiance of 5 mW/cm² and a duty cycle of 20% provides the same number of photons as a CW light beam having an irradiance of 1 mW/cm². However, in contrast to a CW light beam, the parameters of the pulsed light beam can be selected to deliver the photons in a manner which achieve results which are not obtainable using CW light beams.

For example, for hair removal, tattoo removal, or wrinkle smoothing, pulsed light beams have previously been used to achieve selective photothermolysis in which a selected portion of the skin is exposed to sufficiently high temperatures to damage the hair follicles (e.g., temperatures greater than 60 degrees Celsius), to ablate the tattoo ink (e.g., temperatures much greater than 60 degrees Celsius), or to shrink the collagen molecules (e.g., temperatures between 60-70 degrees Celsius), respectively, while keeping the other portions of skin at sufficiently low temperatures to avoid unwanted damage or discomfort. The parameters of these pulsed light beams are selected to achieve the desired elevated temperature at the selected portion of the skin by absorption of the light by the selected chromophore while allowing heat to dissipate (characterized by a thermal relaxation time) during the pulse OFF times to keep other areas of skin at lower temperatures. As described by J. Lepselter et al., "Biological and clinical aspects in laser hair removal," J. Dermatological Treatment, Vol. 15, pp. 72-83 (2004), the pulse ON time for hair removal is selected to be between the thermal relaxation time for the epidermis (about 3-10 milliseconds) and the thermal relaxation time for the hair follicle (about 40-100 milliseconds). In this way, the hair follicle can be heated to sufficiently high temperatures to damage the follicle without causing excessive damage to the surrounding skin.

In contrast to these treatments which are based on creating thermal damage to at least a portion of the skin, certain embodiments described herein utilize pulse parameters which do not create thermal damage to at least a portion of the skin. In certain embodiments, one or more of the temporal pulsewidth, temporal pulseshape, duty cycle, repetition rate, and pulse irradiance of the pulsed light beam are selected such that no portion of the skin is heated to a temperature greater than 60 degrees Celsius, greater than 55 degrees Celsius, greater than 50 degrees Celsius, or greater than 45 degrees Celsius. In certain embodiments, one or more of the temporal pulsewidth, temporal pulseshape, duty cycle, repetition rate, and pulse irradiance of the pulsed light beam are selected such that no portion of the skin is heated to a temperature greater than 30 degrees Celsius above its baseline temperature, greater than 20 degrees Celsius above its baseline temperature, or greater than 10 degrees Celsius above its baseline temperature. In certain embodiments, one or more of the temporal pulsewidth, temporal pulseshape, duty cycle, repetition rate, and pulse irradiance of the pulsed light beam are selected such that no portion of the brain is heated to a temperature greater than 5 degrees Celsius above its baseline temperature, greater than 3 degrees Celsius above its baseline temperature, or greater than 1 degree Celsius above its baseline temperature. As used herein, the term "baseline temperature" has its broadest reasonable interpretation, including but not limited to, the temperature at which the tissue would have if it were not irradiated by the light. In contrast to previous low-light level therapies, the pulsed light beam has an average radiant power in the range of about 1 Watt to about 6 Watts or in a range of about 4 Watt to about 6 Watts.

In certain embodiments, the pulse parameters are selected to achieve other effects beyond those which are achievable using CW light beams. For example, while CW irradiation of brain cells in vivo provides an efficacious treatment of stroke, the use of CW irradiation for the treatment of TBI is more difficult, owing in part to the excess blood within the region of the scalp, skull, or cranium to be irradiated (e.g., due to intercranial bleeding). This excess blood may be between the light source and the target brain tissue to be irradiated, resulting in higher absorption of the light applied to the scalp or skull before it can propagate to the target tissue. This absorption can reduce the amount of light reaching the target tissue and can unduly heat the intervening tissue to an undesirable level.

In certain embodiments described herein, pulsed irradiation may provide a more efficacious treatment. The pulsed irradiation can provide higher peak irradiances for shorter times, thereby providing more power to propagate to the target tissue while allowing thermal relaxation of the intervening tissue and blood between pulses to avoid unduly heating the intervening tissue. The time scale for the thermal relaxation is typically in the range of a few milliseconds. For example, the thermal relaxation time constant (e.g., the time for tissue to cool from an elevated temperature to one-half the elevated temperature) of human skin is about 3-10 milliseconds, while the thermal relaxation time constant of human hair follicles is about 40-100 milliseconds. Thus, previous applications of pulsed light to the body for hair removal have optimized temporal pulsewidths of greater than 40 milliseconds with time between pulses of hundreds of milliseconds.

However, while pulsed light of this time scale advantageously reduces the heating of intervening tissue and blood, it does not provide an optimum amount of efficaciousness as compared to other time scales. In certain embodiments described herein, the patient's scalp or skull is irradiated with pulsed light having parameters which are not optimized to reduce thermal effects, but instead are optimized to stimulate, to excite, to induce, or to otherwise support one or more intercellular or intracellular biological processes which are involved in the survival, regeneration, or restoration of performance or viability of brain cells. Thus, in certain such embodiments, the selected temporal profile can result in temperatures of the irradiated tissue which are higher than those resulting from other temporal profiles, but which are more efficacious than these other temporal profiles. In certain embodiments, the pulsing parameters are selected to utilize the kinetics of the biological processes rather than optimizing the thermal relaxation of the tissue. In certain embodiments, the pulsed light beam has a temporal profile (e.g., peak irradiance per pulse, a temporal pulse width, and a pulse duty cycle) selected to modulate membrane potentials in order to enhance, restore, or promote cell survival, cell function, or both of the irradiated brain cells following the traumatic brain injury. For example, in certain embodiments, the pulsed light has a temporal profile which supports one or more intercellular or intracellular biological processes involved in the survival or regeneration of brain cells, but does not optimize the thermal relaxation of the irradiated tissue. In certain embodiments, the brain cells survive longer after the irradiation as compared to their survival if the irradiation did not occur. For example, the light of certain embodiments can have a protective effect on the brain cells, or can cause a regeneration process in the brain cells.

In certain embodiments, the temporal profile (e.g., peak irradiance, temporal pulse width, and duty cycle) are selected to utilize the kinetics of the biological processes while maintaining the irradiated portion of the scalp or skull at or below a predetermined temperature. This predetermined temperature is higher than the optimized temperature which could be achieved for other temporal profiles (e.g., other values of the peak irradiance, temporal pulse width, and duty cycle) which are optimized to minimize the temperature increase of surrounding tissue due to the irradiation. For example, a temporal profile having a peak irradiance of 10 W/cm$^2$ and a duty cycle of 20% has a time-averaged irradiance of 2 W/cm$^2$. Such a pulsed light beam provides the same number of photons to the irradiated surface as does a continuous-wave (CW) light beam with an irradiance of 2 W/cm$^2$. However, because of the "dark time" between pulses, the pulsed light beam can result in a lower temperature increase than does the CW light beam. To minimize the temperature increase of the irradiated portion of the scalp or skull, the temporal pulse width and the duty cycle can be selected to allow a significant portion of the heat generated per pulse to dissipate before the next pulse reaches the irradiated portion. In certain embodiments described herein, rather than optimizing the beam temporal parameters to minimize the temperature increase, the temporal parameters are selected to effectively correspond to or to be sufficiently close to the timing of the biomolecular processes involved in the absorption of the photons to provide an increased efficacy. Rather than having a temporal pulse width on the order of hundreds of microseconds, certain embodiments described herein utilize a temporal pulse width which does not optimize the thermal relaxation of the irradiated tissue (e.g., milliseconds, tens of milliseconds, hundreds of milliseconds). Since these pulse widths are significantly longer than the thermal relaxation time scale, the resulting temperature increases are larger than those of smaller pulse widths, but still less than that of CW light beams due to the heat dissipation the time between the pulses.

A number of studies have investigated the effects of in vitro irradiation of cells using pulsed light on various aspects of the cells. A study of the action mechanisms of incoherent pulsed radiation at a wavelength of 820 nanometers (pulse repetition frequency of 10 Hz, pulse width of 20 milliseconds, dark period between pulses of 80 milliseconds, and duty factor (pulse duration to pulse period ratio) of 20%) on in vitro cellular adhesion has found that pulsed infrared radiation at 820 nanometers increases the cell-matrix attachment. (T. I. Karu et al., "*Cell Attachment to Extracellular Matrices is Modulated by Pulsed Radiation at* 820 *nm and Chemicals that Modify the Activity of Enzymes in the Plasma Membrane*," Lasers in Surgery and Medicine, Vol. 29, pp. 274-281 (2001) which is incorporated in its entirety by reference herein.) It was hypothesized in this study that the modulation of the monovalent ion fluxes through the plasma membrane, and not the release of arachidonic acid, is involved in the cellular signaling pathways activated by irradiation at 820 nanometers. A study of light-induced changes to the membrane conductance of ventral photoreceptor cells found behavior which was dependent on the pulse parameters, indicative of two light-induced membrane processes. (J. E. Lisman et al., "*Two Light-Induced Processes in the Photoreceptor Cells of Limulus Ventral Eye*," J. Gen. Physiology, Vol. 58, pp. 544-561 (1971), which is incorporated in its entirety by reference herein.) Studies of laser-activated electron injection into oxidized cytochrome c oxidase observed kinetics which establish the reaction sequence of the proton pump mechanism and some of its thermodynamic properties have time constants on the order of a few milliseconds. (I. Belevich et al., "*Exploring the proton pump mechanism of cytochrome c oxidase in real time*," Proc. Nat'l Acad. Sci., Vol. 104, pp. 2685-2690 (2007); I. Belevich et al., "*Proton-coupled electron transfer drives the proton pump of cytochrome c oxidase*," Nature, Vol. 440, pp. 829-832 (2006), both of which are incorporated in its entirety by reference herein.) An in vivo study of neural activation based on pulsed infrared light proposed a photothermal effect from transient tissue temperature changes resulting in direct or indirect activation of transmembrane ion channels causing propagation of the action potential. (J. Wells et al., "*Biophysical mechanisms responsible for pulsed low-level laser excitation of neural tissue*," Proc. SPIE, Vol. 6084, pp. 60840X (2006), which is incorporated in its entirety by reference herein.)

In certain embodiments, the temporal profile of the pulsed light beam comprises a peak irradiance, a temporal pulse width, a temporal pulse shape, a duty cycle, and a pulse repetition rate or frequency. In certain embodiments in which the pulsed light beam is transmitted through a region of the scalp or skull containing an excess amount of hemorrhagic blood due to the at least one physical trauma (e.g., due to intercranial bleeding), at least one of the peak irradiance, temporal pulse width, temporal pulse shape, duty cycle, and pulse repetition rate or frequency is selected to provide a time-averaged irradiance (averaged over a time period including a plurality of pulses) at the emission surface 22 of the output optical assembly 20 between about 10 mW/cm$^2$ to about 10 W/cm$^2$, between about 100 mW/cm$^2$ to about 1000 mW/cm$^2$, between about 500 mW/cm$^2$ to about 1 W/cm$^2$, or between about 650 mW/cm$^2$ to about 750 mW/cm$^2$ across the cross-sectional area of the light beam. In certain such embodiments, the time-averaged irradiance at the brain cells being treated (e.g., at a depth of approximately 2 centimeters below the dura) is greater than 0.01 mW/cm$^2$.

In certain embodiments, the peak irradiance per pulse across the cross-sectional area of the light beam at the emission surface 22 of the output optical assembly 20 is in a range between about 10 mW/cm$^2$ to about 10 W/cm$^2$, between about 100 mW/cm$^2$ to about 1000 mW/cm$^2$, between about 500 mW/cm$^2$ to about 1 W/cm$^2$, between about 650 mW/cm$^2$ to about 750 mW/cm$^2$, between about 20 mW/cm$^2$ to about 20 W/cm$^2$, between about 200 mW/cm$^2$ to about 2000 mW/cm$^2$, between about 1 W/cm$^2$ to about 2 W/cm$^2$, between about 1300 mW/cm$^2$ to about 1500 mW/cm$^2$, between about 1 W/cm$^2$ to about 1000 W/cm$^2$, between about 10 W/cm$^2$ to about 100 W/cm$^2$, between about 50 W/cm$^2$ to about 100 W/cm$^2$, or between about 65 W/cm$^2$ to about 75 W/cm$^2$. In certain embodiments, the temporal pulse shape is generally rectangular, generally triangular, or any other shape. In certain embodiments, the pulses have a rise time (e.g., from 10% of the peak irradiance to 90% of the peak irradiance) less than 1% of the pulse ON time, or a fall time (e.g., from 90% of the peak irradiance to 10% of the peak irradiance) less than 1% of the pulse ON time.

In certain embodiments, the pulses have a temporal pulsewidth (e.g., pulse ON time) in a range between about 0.001 millisecond and about 150 seconds, between about 0.01 millisecond and about 10 seconds, between about 0.1 millisecond and about 1 second, between about 0.5 millisecond and about 100 milliseconds, between about 2 milliseconds and about 20 milliseconds, or between about 1 millisecond and about 10 milliseconds. In certain embodiments, the pulse width is about 0.5, 1, 2, 4, 6, 8, 10, 15, 20, 30, 40, 50, 60, 70, 80, 90, 100, 120, 140, 160, 180, 200, 220, 240, 260, 280, or 300 milliseconds. In certain embodiments, the temporal pulsewidth is in a range between about 0.1 millisecond and 150 seconds.

In certain embodiments, the time between pulses (e.g., pulse OFF time) is in a range between about 0.01 millisecond and about 150 seconds, between about 0.1 millisecond and about 100 millisecond, between about 4 milliseconds and about 1 second, between about 8 milliseconds and about 500 milliseconds, between about 8 milliseconds and about 80 milliseconds, or between about 10 milliseconds and about 200 milliseconds. In certain embodiments, the time between pulses is about 4, 8, 10, 20, 50, 100, 200, 500, 700, or 1000 milliseconds.

In certain embodiments, the pulse duty cycle is in a range between about 1% and about 80% or in a range between about 10% and about 30%. In certain embodiments, the pulse duty cycle is about 10%, 20%, 30%, 40%, 50%, 60%, 70%, 80%, or 90%.

Beam Size and Beam Profile

In certain embodiments, the light beam emitted from the output optical assembly 20 has a nominal diameter in a range of about 10 millimeters to about 40 millimeters, in a range of about 20 millimeters to about 35 millimeters, or equal to about 30 millimeters. In certain embodiments, the cross-sectional area is generally circular with a radius in a range of about 1 centimeter to about 2 centimeters. In certain embodiments, the light beam emitted from the emission surface 22 has a cross-sectional area greater than about 2 cm$^2$ or in a range of about 2 cm$^2$ to about 20 cm$^2$ at the emission surface 22 of the optical element 23. In certain embodiments, the output optical element 23 has an aperture diameter of less than 33 millimeters.

As used herein, the beam diameter is defined to be the largest chord of the perimeter of the area of the scalp or skull irradiated by the light beam at an intensity of at least 1/e$^2$ of the maximum intensity of the light beam. The perimeter of the light beam used to determine the diameter of the beam is defined in certain embodiments to be those points at which the intensity of the light beam is 1/e$^2$ of the maximum intensity of the light beam. The maximum-useful diameter of certain embodiments is limited by the size of the patient's head and by the heating of the patient's head by the irradiation. The minimum-useful diameter of certain embodiments is limited by heating and by the total number of treatment sites that could be practically implemented. For example, to cover the patient's skull with a beam having a small beam diameter would correspondingly use a large number of treatment sites. In certain embodiments, the time of irradiation per treatment site can be adjusted accordingly to achieve a desired exposure dose.

Specifying the total flux inside a circular aperture with a specified radius centered on the exit aperture ("encircled energy") is a method of specifying the power (irradiance) distribution over the light beam emitted from the emission surface 22. The "encircled energy" can be used to ensure that the light beam is not too concentrated, too large, or too small. In certain embodiments, the light beam emitted from the emission surface has a total radiant power, and the light beam has a total flux inside a 20-millimeter diameter cross-sectional circle centered on the light beam at the emission surface 22 which is no more than 75% of the total radiant power. In certain such embodiments, the light beam has a total flux inside a 26-millimeter diameter cross-sectional circle centered on the light beam at the emission surface 22 which is no less than 50% of the total radiant power.

In certain embodiments, the beam intensity profile has a semi-Gaussian profile, while in certain other embodiments, the beam intensity profile has a "top hat" profile. In certain embodiments, the light beam is substantially without high flux regions or "hot spots" in the beam intensity profile in which the local flux, averaged over a 3 millimeter by 3 millimeter area, is more than 10% larger than the average flux. Certain embodiments of the apparatus 10 advantageously generate a light beam substantially without hot spots, thereby avoiding large temperature gradients at the patient's skin which would otherwise cause discomfort to the patient.

Divergence

In certain embodiments, the beam divergence emitted from the emission surface 22 is significantly less than the scattering angle of light inside the body tissue being irradiated, which is typically several degrees. In certain embodiments, the light beam has a divergence angle greater than zero and less than 35 degrees.

As the distance between a light source and an observer increases, the diameter of the source becomes less relevant to considerations of the beam divergence. For example, an end of the optical fiber 40 providing the light has a diameter of about 1 millimeter. At a close distance, observing from a specific location, light rays from the edges of the optical fiber end can arrive at the observation point with significantly different angles. However, as the observation point moves away from the light source, this angular discrepancy is reduced and the source appears more like a point source.

In certain embodiments, with the output optical assembly 20 mounted onto the apparatus 10, the optical distance between the emission surface 22 and the end of the optical fiber 40 is about 82.7 millimeters. The beam divergence dictated by the numerical aperture of the optical fiber 40 and the exit aperture of the optical element 23 is about 23 degrees. In certain embodiments, with the output optical assembly 20 not mounted onto the apparatus 10, the optical distance between the window 70 and the end of the optical fiber is about 57.5 millimeters, and the beam divergence dictated by the numerical aperture of the optical fiber 40 and the exit aperture of the window 70 is about 16 degrees. With a source diameter of about 1 millimeter, the angular ambiguity in the beam divergence is about ±0.35 degree. Thus, the angular ambiguity is much less than the beam divergence angle regardless of whether the output optical assembly 20 is mounted or not onto the apparatus 10, so the optical fiber 40 can be treated as a point source. In certain such embodiments, the beam divergence or radiant intensity (e.g., measured in Watts/steradian) can be calculated directly from the beam profile or from the irradiance.

Treatment Time

In certain embodiments, the treatment per treatment site proceeds continuously for a period of about 10 seconds to about 2 hours, for a period of about 1 to about 10 minutes, or for a period of about 1 to 5 minutes. For example, the treatment time per treatment site in certain embodiments is about two minutes. In other embodiments, the light energy is delivered for at least one treatment period of at least about five minutes, or for at least one treatment period of at least ten minutes. The minimum treatment time of certain embodiments is limited by the biological response time (which is on the order of microseconds). The maximum treatment time of certain embodiments is limited by heating and by practical treatment times (e.g., completing treatment within about 24 hours of stroke onset). The light energy can be pulsed during the treatment period or the light energy can be continuously applied during the treatment period. If the light is pulsed, the pulses can be 2 milliseconds long and occur at a frequency of 100 Hz, although longer pulselengths and lower frequencies can be used, or at least about 10 nanosecond long and occur at a frequency of up to about 100 kHz.

In certain embodiments, the treatment may be terminated after one treatment period, while in other embodiments, the treatment may be repeated for at least two treatment periods. The time between subsequent treatment periods can be at least about five minutes, at least two in a 24-hour period, at least about 1 to 2 days, or at least about one week. The length of treatment time and frequency of treatment periods can depend on several factors, including the functional recovery of the patient and the results of imaging analysis of the injury (e.g., infarct). In certain embodiments, one or more treatment parameters can be adjusted in response to a feedback signal from a device (e.g., magnetic resonance imaging) monitoring the patient.

Cooling Parameters

In certain embodiments, the apparatus 10 comprises an output optical element 23 in optical communication with a source of light. The output optical element 23 comprises an emission surface 22 configured to emit a light beam in accordance with the light parameters disclosed above. In certain embodiments the apparatus 10 further comprises a thermally conductive portion configured to be placed in thermal communication with the irradiated portion of the patient's scalp or skull and to remove heat from the irradiated portion of the patient's scalp or skull. In certain embodiments, the thermally conductive portion comprises the output optical element 23. The thermally conductive portion of certain embodiments is releasably coupled to the output optical element 23.

In certain embodiments, the thermally conductive portion removes heat from the irradiated portion of the patient's scalp or skull. This cooling of the scalp or skull can to improve the comfort of the patient, by controlling, inhibiting, preventing, minimizing, or reducing temperature increases at the scalp or skull due to the irradiation. Thus, by virtue of the cooling of the portion of the patient's scalp or skull being irradiated, the temperature of the irradiated portion of the patient's scalp or skull is lower than it would otherwise be if the irradiated portion of the scalp or skull were not cooled. For example, by cooling the irradiated portion of the patient's scalp or skull, the temperature of the irradiated portion of the patient's scalp or skull can be higher than the temperature of the portion of the patient's scalp or skull if it were not irradiated, but lower than the temperature of the portion of the patient's scalp or skull if it were irradiated but not cooled. In addition, this cooling of the scalp or skull can be to perform double-blind studies of the efficacy of the phototherapy treatment by masking any heating of the scalp or skull due to the irradiation. (See, e.g., B. Catanzaro et al., "Managing Tissue Heating in Laser Therapy to Enable Double-Blind Clinical Study," Mechanisms for Low-Light Therapy, Proc. of the SPIE, Vol. 6140, pp. 199-208 (2006).)

In certain embodiments, heat is removed from the irradiated portion of the patient's scalp or skull by the thermally conductive portion at a rate in a range of about 0.1 Watt to about 5 Watts or in a range of about 1 Watt to about 3 Watts. In certain embodiments, the thermally conductive portion is configured to maintain the temperature of the irradiated portion of the patient's scalp or skull to be less than 42 degrees Celsius. The thermally conductive portion of certain embodiments is in thermal communication with the emission surface 22 and is configured to maintain the temperature of the emission surface to be in a range of 18 degrees Celsius to 25 degrees Celsius under a heat load of 2 Watts. For a general description of cooling of the scalp, see, e.g., F. E. M. Janssen et al., "Modeling of temperature and perfusion during scalp cooling," Phys. Med. Biol., Vol. 50, pp. 4065-4073 (2005). In certain embodiments in which pulsed light is used, the rate of heat removal can be less, or cooling may not be utilized for certain ranges of pulsed dosimetries and timing.

Pressure Parameters

In certain embodiments, the apparatus 10 is configured to have the thermally conductive portion move relative to a second portion of the apparatus 10 upon a pressure being applied to the thermally conductive portion above a predetermined threshold pressure in a direction of movement of the thermally conductive portion relative to the second portion of the apparatus 10. The predetermined threshold pressure is sufficient to have the thermally conductive portion in thermal communication with the portion of the patient's scalp or skull. In certain such embodiments, the apparatus 10 comprises a sensor configured to be responsive to the movement of the thermally conductive portion relative to the second portion by generating a signal (e.g., binary, analog, or digital) indicative of the movement.

In certain such embodiments, the sensor 130 in conjunction with the trigger force spring 140 and the trigger force adjustment mechanism 142 provides a mechanism for detecting whether the apparatus 10 is being applied to the patient's scalp or skull with a pressure above the predetermined threshold pressure. In certain such embodiments, the sensor 130 detects movement between the first portion of the apparatus 10 and the second portion of the apparatus 10 upon placing the emission surface 22 in thermal communication with the patient's scalp or skull with sufficient pressure to overcome the restoring force of the trigger force spring 140. Upon applying the threshold pressure to the emission surface 22 move the first and second portions relative to one another, the sensor 130 detects the movement and generates a corresponding signal. In certain embodiments, the apparatus 10 further comprises a controller operatively coupled to the light source and to the sensor 130. The controller is configured to receive the signal from the sensor 130 and to turn on the light source in response to the signal being indicative of the pressure being above the predetermined threshold pressure.

In certain embodiments, the threshold pressure is set to be a pressure which results in blanching of the portion of the patient's scalp to be irradiated. In certain embodiments, the threshold pressure is 0.1 pound per square inch, while in certain other embodiments, the threshold pressure is one pound per square inch or about two pounds per square inch.

In certain embodiments in which pulsed light is used, the amount of blanching can be less, or blanching may not be utilized for certain ranges of pulsed dosimetries and timing. For example, in certain embodiments, the patient may have a heightened sensitivity to pressure applied to the scalp or skull (e.g., a TBI patient). Thus, in certain embodiments, the apparatus 10 does not apply sufficient pressure to the scalp of the patient (e.g., applies no pressure to the patient's scalp) to blanch the irradiated portion of the scalp during the irradiation. In certain other embodiments in which some amount of blanching of the irradiated portion of the scalp is desired, the maximum pressure used to blanch the irradiated portion of the scalp is limited by patient comfort levels and tissue damage levels. For example, the cranium or skull of a TBI patient may have cracks or breaks such that the brain would be adversely affected if pressure were applied to the scalp. The amount of pressure used, if any, is determined at least in part, on the amount of pressure that the patient can withstand without additional damage being done by the application of pressure.

Irradiating Multiple Portions of the Scalp or Skull

Figure 22A:
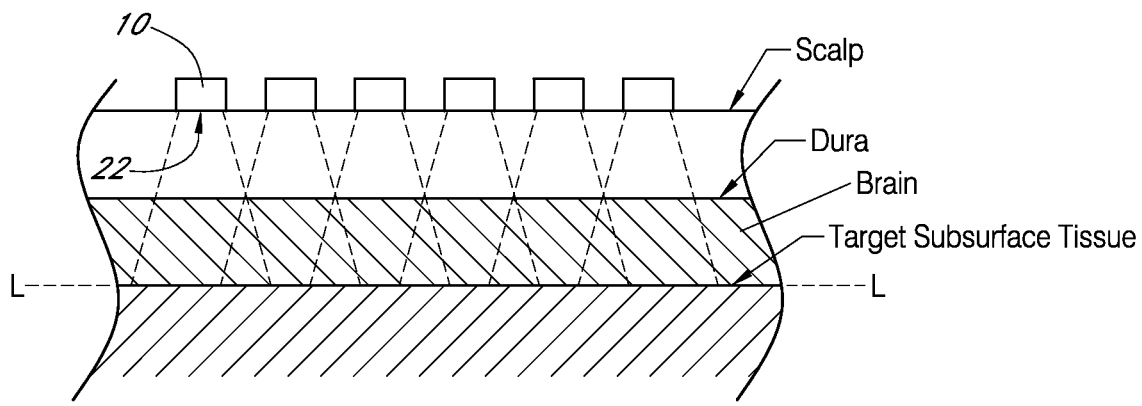
FIGS. 22A-22C schematically illustrate an embodiment in which the apparatus is placed in thermal communication sequentially with a plurality of treatment sites corresponding to portions of the patient's scalp.
Figure 22B:
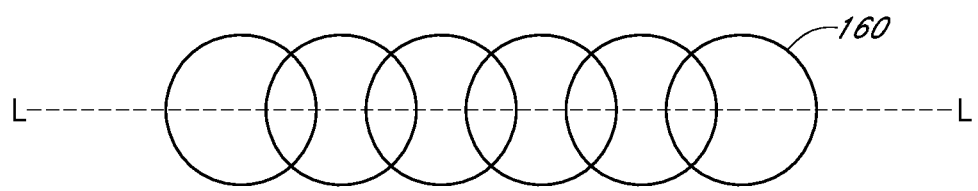
Figure 22C:
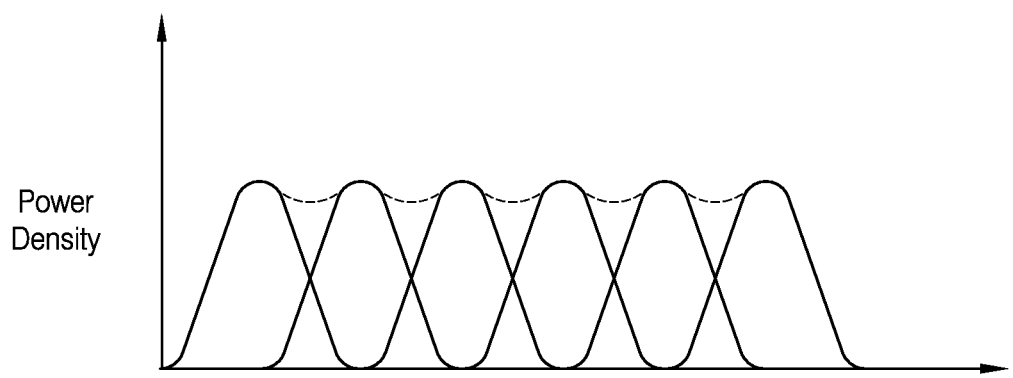

FIGS. 22A-22C schematically illustrate an embodiment in which the apparatus 10 is placed in thermal communication sequentially with a plurality of treatment sites corresponding to portions of the patient's scalp. In certain such embodiments, the light emitted from the emission surface 22 propagates through the scalp to the brain and disperses in a direction generally parallel to the scalp, as shown in FIG. 22A. In certain embodiments in which the patient is suffering from a TBI, one or more of the treatment sites has a portion of the skull exposed and at least a portion of the light is applied to the exposed portion of the skull without propagating through scalp tissue. In certain embodiments, the treatment sites of the patient's scalp do not overlap one another. The treatment sites (e.g., twenty treatment sites) are preferably spaced sufficiently far apart from one another such that the light emitted from the emission surface 22 to irradiate a treatment site of the patient's scalp is transmitted through intervening tissue to irradiate an area of the patient's brain which overlaps one or more areas of the target tissue of the patient's brain irradiated by the light emitted from the emission surface 22 when a neighboring treatment site of the patient's scalp is irradiated. FIG. 22B schematically illustrates this overlap as the overlap of circular spots 160 across the target tissue at a reference depth at or below the surface of the brain. FIG. 22C schematically illustrates this overlap as a graph of the irradiance at the reference depth of the brain along the line L-L of FIGS. 22A and 22B. Summing the irradiances from the neighboring treatment sites (shown as a dashed line in FIG. 22C) serves to provide a more uniform light distribution at the target tissue to be treated. In such embodiments, the summed irradiance is preferably less than a damage threshold of the brain and above an efficacy threshold. In certain embodiments, portions of the brain irradiated by irradiating the treatment sites at the scalp do not overlap one another. In certain such embodiments, the treatment sites at the scalp are positioned so as to irradiate as much of the cortex as possible.

Example Wearable Apparatus

Figure 23A:
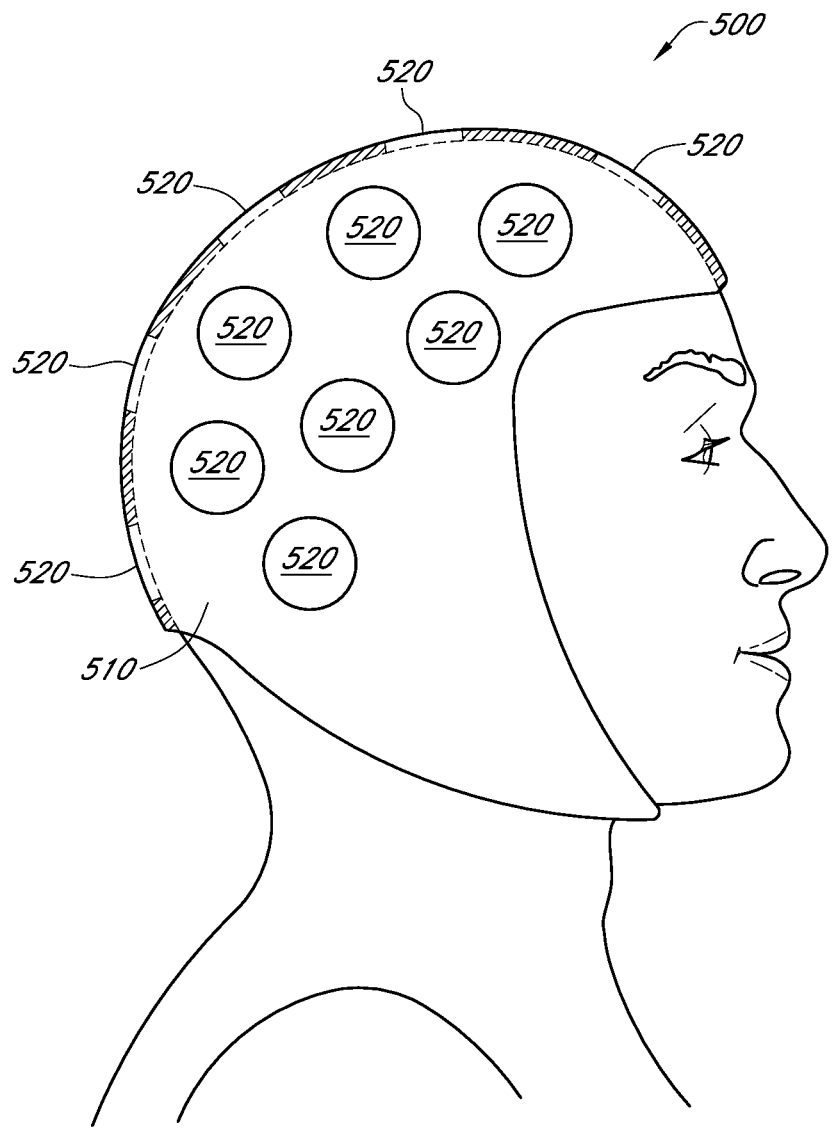
FIG. 23A schematically illustrates an example apparatus which is wearable by a patient for treating the patient's brain.

FIG. 23A schematically illustrates an example apparatus 500 which is wearable by a patient for treating the patient's brain. The apparatus 500 comprises a body 510 and a plurality of indicators 520. The body 510 is adapted to be worn over at least a portion of the patient's scalp when the apparatus 500 is worn by the patient. The plurality of indicators 520 correspond to a plurality of treatment site locations at the patient's scalp where light is to be applied to irradiate at least a portion of the patient's brain. At least one indicator 520 comprises an optically transmissive portion which is substantially transmissive (e.g., substantially transparent or substantially translucent) to light emitted from the emission surface 22 to irradiate at least a portion of the patient's brain.

In certain embodiments, at least one of the indicators 520 denotes a position within an area of the patient's scalp corresponding to a treatment site location. In certain such embodiments, the position is the center of the area of the patient's scalp. The adjacent treatment sites of certain embodiments have areas which do not overlap one another or have perimeters which are spaced from one another. In certain such embodiments, the perimeters are spaced from one another by at least 10 millimeters or at least 25 millimeters.

In certain embodiments, the optically transmissive portion of the at least one indicator 520 comprises an opening or aperture through the body 510 at which the beam delivery apparatus 10 can be placed to irradiate the portion of the patient's scalp exposed by the hole or aperture. In other embodiments, the optically transmissive portion comprises a hollow compartment or cavity that does not extend completely through the indicator 520 to the surface of the scalp or skull. For example, the indicator 520 can include a mylar film to prevent contact between a light source and the patient, thereby avoiding potential contamination of a contact portion of the light source by contacting the patient. The use of the mylar or other suitable protective film advantageously enables the light source (or at least the contact portion of the light source) to be reused for multiple patients. In other embodiments, the light source or a contact portion of the light source can be disposed after a single use.

In certain embodiments, the optically transmissive portion has a substantially circular perimeter and a diameter in a range between 20 millimeters and 50 millimeters or in a range between 25 millimeters and 35 millimeters. In certain embodiments, the optically transmissive portion has a substantially elliptical perimeter with a minor axis greater than 20 millimeters and a major axis less than 50 millimeters. Other shapes of the optically transmissive portion are also compatible with certain embodiments described herein.

In certain embodiments, the plurality of indicators 520 comprises at least about 10 indicators 520 distributed across the patient's scalp, while in certain other embodiments, the plurality of indicators 520 comprises 20 indicators 520. In certain other embodiments, the plurality of indicators 520 comprises between 15 and 25 indicators 520. In certain embodiments, the optically transmissive portion of each indicator 520 has an area of at least 1 cm², in a range between 1 cm² and 20 cm², or in a range between 5 cm² and 10 cm².

In certain embodiments, the body 510 comprises a hood, while in other embodiments, the body 510 comprises a cap or has another configuration which is wearable on the patient's head and serves as a support for orienting the indicators 520 on the patient's head. In certain embodiments, the body 510 comprises a stretchable or pliant material which generally conforms to the patient's scalp. In certain embodiments, the body 510 comprises nylon-backed polychloroprene or Tyvek®. In certain embodiments, the body 510 is available in different sizes (e.g., small, medium, large) to accommodate different sizes of heads. In certain embodiments, the body 510 is disposable after a single use to advantageously avoid spreading infection or disease between subsequent patients.

The indicators 520 of certain embodiments are configured to guide an operator to irradiate the patient's scalp at the corresponding treatment site locations sequentially one at a time in a predetermined order.

Figure 23B:
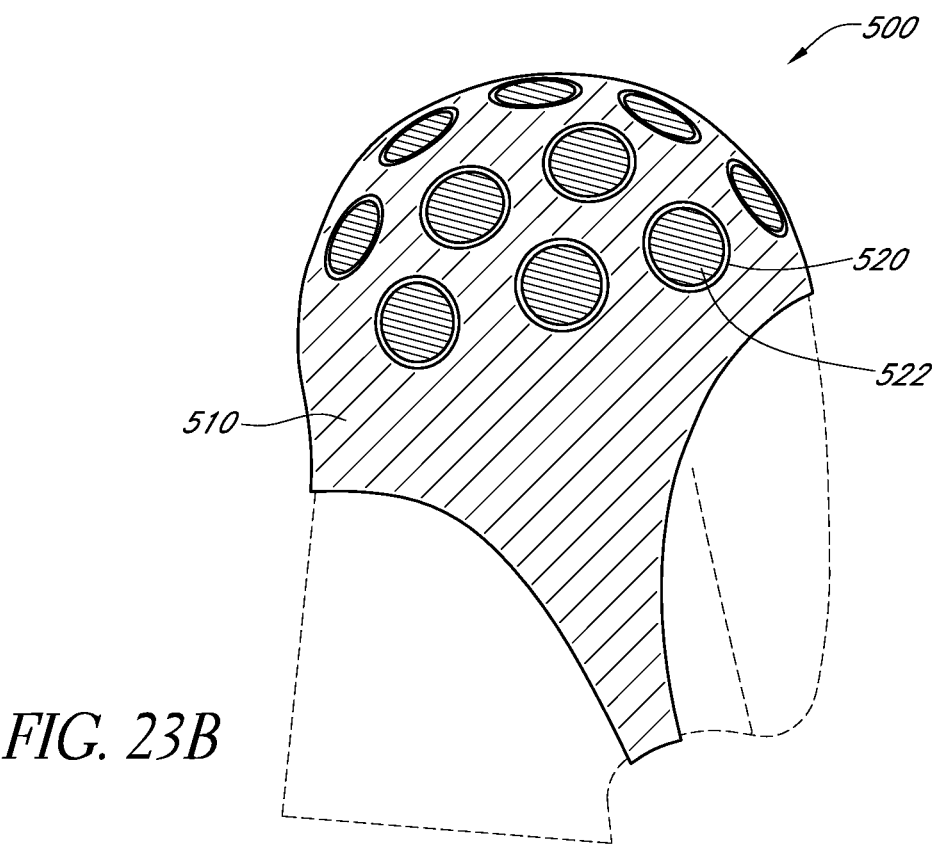
FIGS. 23B and 23C schematically illustrate the left-side and right-side of an example apparatus, respectively, with labels substantially covering the indicators corresponding to the treatment sites.
Figure 23C:
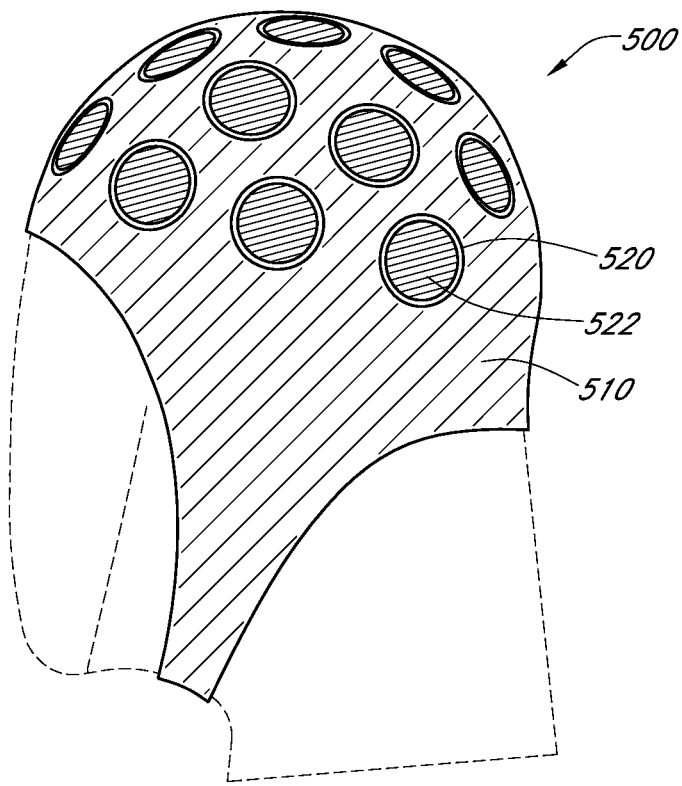

FIGS. 23B and 23C schematically illustrate the left-side and right-side of the example apparatus 500, respectively, with labels 522 substantially covering the indicators 520 corresponding to the treatment sites. In certain embodiments, the labels 522 are advantageously used to keep track of which treatment sites have been irradiated and which treatment sites are yet to be irradiated. In certain such embodiments, at least a portion of each label 522 comprises a portion of the body (e.g., a pull-off tab or flap) which is configured to be removed from the apparatus 500 when the treatment site corresponding to the indicator 520 has been irradiated. In certain embodiments, the labels 522 comprise removable portions of the body 510 which cover the corresponding indicator 520. In certain such embodiments, prior to irradiating the treatment site location corresponding to the indicator 520, the corresponding label 522 can be removed to allow access to the underlying portion of the patient's scalp.

In certain embodiments, the label 522 has a code sequence which the operator enters into the controller prior to irradiation so as to inform the controller of which treatment site is next to be irradiated. In certain other embodiments, each label 522 comprises a bar code or a radio-frequency identification device (RFID) which is readable by a sensor electrically coupled to the controller. The controller of such embodiments keeps track of which treatment sites have been irradiated, and in certain such embodiments, the controller only actuates the light source when the beam delivery apparatus 10 is in optical and thermal communication with the proper treatment site of the patient's scalp.

Figure 23D:
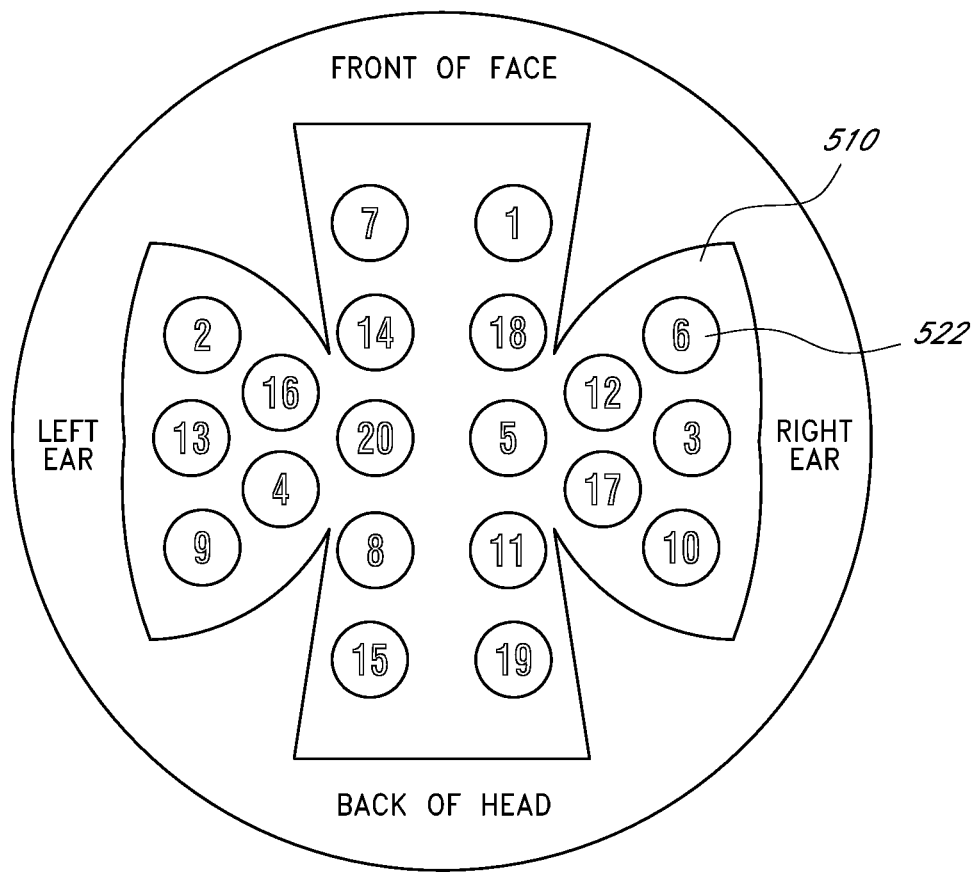
FIG. 23D schematically illustrates an example labeling configuration from above a flattened view of the apparatus of FIGS. 23B and 23C.

FIG. 23D schematically illustrates an example labeling configuration from above a flattened view of the apparatus 500 of FIGS. 23B and 23C. The labeling convention of FIG. 23D is compatible with irradiation of both halves or hemispheres of the patient's brain. Other labeling conventions are also compatible with embodiments described herein.

In certain embodiments, the labels 522 are advantageously used to guide an operator to irradiate the patient's brain at the various treatment sites sequentially at each of the treatment sites one at a time through the indicators 520 in a predetermined order by optically and thermally coupling the beam delivery apparatus 10 to sequential treatment sites corresponding to the indicators 520. For example, for the labeling configuration of FIG. 23D, the operator can first irradiate treatment site "1," followed by treatment sites "2," "3," "4," etc. to sequentially irradiate each of the twenty treatment sites one at a time. In certain such embodiments, the predetermined order of the treatment sites is selected to advantageously reduce temperature increases which would result from sequentially irradiating treatment sites in proximity to one another.

In certain embodiments, the predetermined order comprises irradiation of a first treatment site location on a first side of the patient's scalp (e.g., site "2" of FIG. 23D), then irradiation of a second treatment site location on a second side of the patient's scalp (e.g., site "3" of FIG. 23D), then irradiation of a third treatment site location on the first side of the patient's scalp (e.g., site "4" of FIG. 23D). In certain such embodiments, the predetermined order further comprises irradiation of a fourth treatment site location on the second side of the patient's scalp after irradiation of the third treatment site location. In certain embodiments, two sequentially irradiated treatment site locations are separated from one another by at least 25 millimeters.

For example, in certain embodiments, the predetermined order comprises at least a portion of the following sequence of treatment sites:

1. Right anterior frontal
2. Left lateral frontal
3. Right anteroinferior parietal
4. Left posterior mid-parietal
5. Right superior parietal
6. Right lateral frontal
7. Left anterior frontal
8. Left posterior superior parietal
9. Left posteroinferior parietal
10. Right posteroinferior parietal
11. Right posterior superior parietal
12. Right anterior mid-parietal
13. Left anteroinferior parietal
14. Left anterosuperior frontal
15. Left superior occipital
16. Left anterior mid-parietal
17. Right posterior mid-parietal
18. Right anterosuperior frontal
19. Right superior occipital
20. Left superior parietal For example, the predetermined order of certain embodiments comprises two, three, four, or more of these treatment sites in the relative order listed above. The sequence of treatment sites of certain embodiments comprises two, three, four, or more of these treatment sites in a relative order which is the reverse of the sequence listed above. While certain embodiments utilize at least a portion of the relative order listed above without irradiation at an additional treatment site between two sequentially listed treatment sites, certain other embodiments utilize at least a portion of the relative order listed above with one or more additional treatment sites between two of the sequentially listed treatment sites. In certain embodiments, the exact anatomic locations of each treatment site may be adjusted from those listed above to account for variations among the sizes of the heads of the patients (e.g., very large or very small). Thus, in certain embodiments, there is some variability regarding the locations of the treatment sites for any given individual.

In certain embodiments, the apparatus 500 serves as a template for marking the patient's scalp to indicate the treatment site locations. The apertures of the apparatus 500 can be used to guide a user to place marks on the patient's scalp, and the apparatus 500 can then be removed from the patient's scalp before the beam delivery apparatus 10 is applied to the scalp for irradiating the patient's brain. The marks remain on the patient's scalp to guide the operator while the patient's brain is irradiated.

Figure 23E:
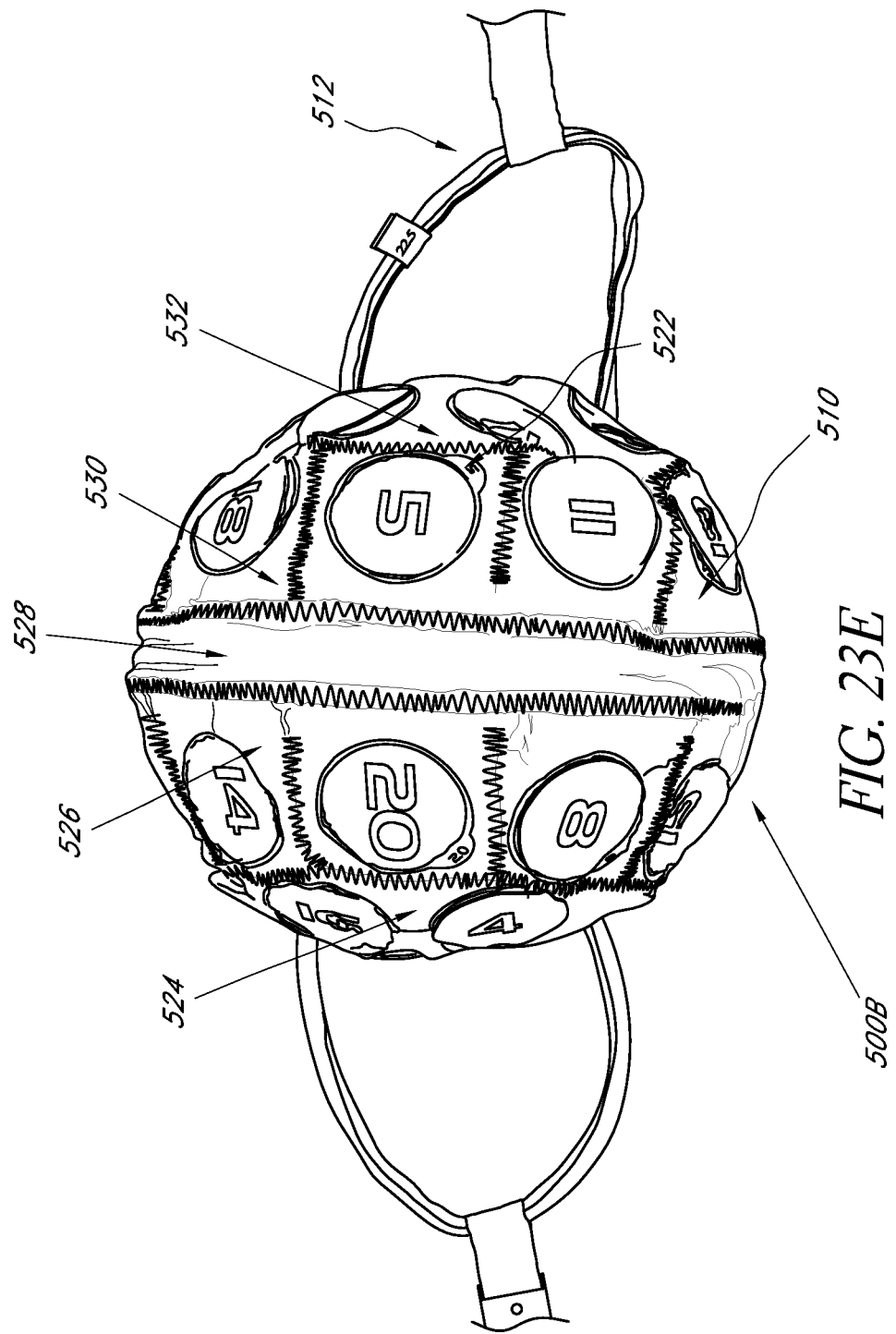
FIGS. 23E-23H illustrate an example embodiment of a wearable apparatus for use in treating the patient's brain with phototherapy.

FIG. 23E schematically illustrates a top perspective view of another example embodiment of the wearable apparatus 500. The wearable apparatus 500 includes a body 510 comprising five panels (a lower left panel 524, an upper left panel 526, a midline panel 528, an upper right panel 530, and a lower right panel 532) and retention assembly 512. The panels of the wearable apparatus 500 include one or more position indicators 520 that correspond to respective treatment site locations at the patient's scalp where light is to be applied to irradiate at least a portion of the patient's brain. The midline panel 528 advantageously does not include any position indicators 520. The position indicators 520 can each include a label 522 with a number or other indicia to indicate a sequence of treatment. At least a portion of the label 522 can be removed to form an opening or aperture at which the beam delivery apparatus 10 can be placed to irradiate the portion of the patient's scalp exposed by the hole or aperture.

The retention assembly 512 can include a retaining member that extends from one side of the apparatus 500 to the other side (e.g., a chin strap). The retaining member can be formed of a unitary strap element or two strap elements that couple together via a coupling mechanism (not shown). The coupling mechanism can comprise any suitable means of coupling two strap elements together (e.g., Velcro strips, buckles, snaps, hooks, latches, clips, buttons, ties, or the like). Other embodiments do not include the retention assembly 512.

Figure 23F:
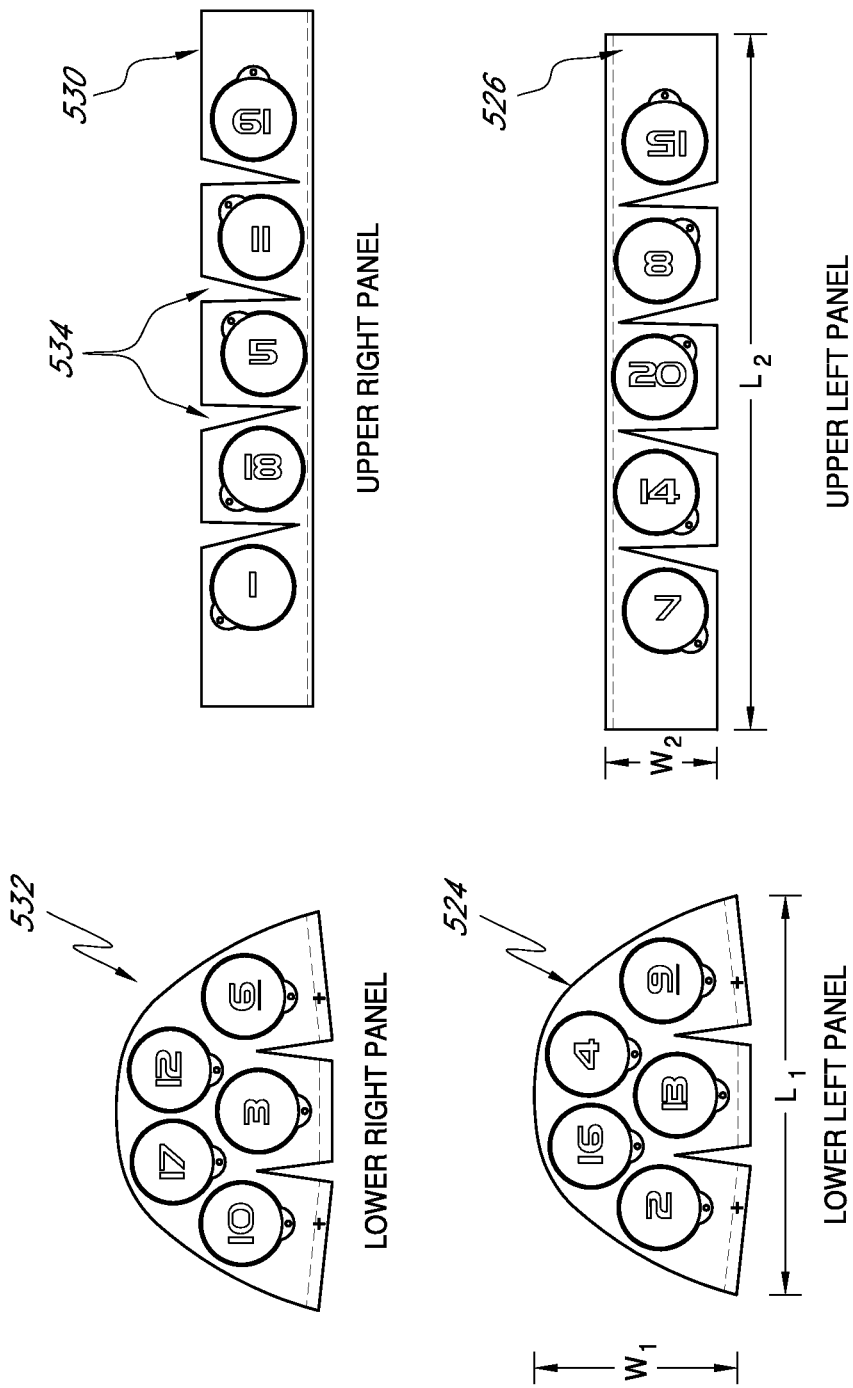

FIG. 23F illustrates the lower left panel 524, the upper left panel 526, the upper right panel 530 and the lower right panel 532. The width of the lower left panel 524 and the lower right panel 532 (denoted in FIG. 23F by "$W_1$") can be approximately 10 cm. The length of the lower left panel 524 and the lower right panel 532 (denoted in FIG. 23F by "$L_1$") can be approximately 20 cm. The length of the upper left panel 526 and the upper right panel 530 (denoted in FIG. 23F by "$L_2$") can be between 30 and 35 cm. The width of the upper left panel 526 and the upper right panel 530 (denoted in FIG. 23F by "$W_2$") can be between about 4 and 6 cm. As shown in FIG. 23F, one or more of the panels (e.g., the upper left panel 526) includes a label indicating the front of the body 510 and a label indicating a size of the body 510. The panels include slits 534 that can be sewn together during assembly, thereby providing a contour which is configured to at least partially conform to the shape of the patient's scalp. More or fewer panels can be included in alternative embodiments.

Figure 23G:
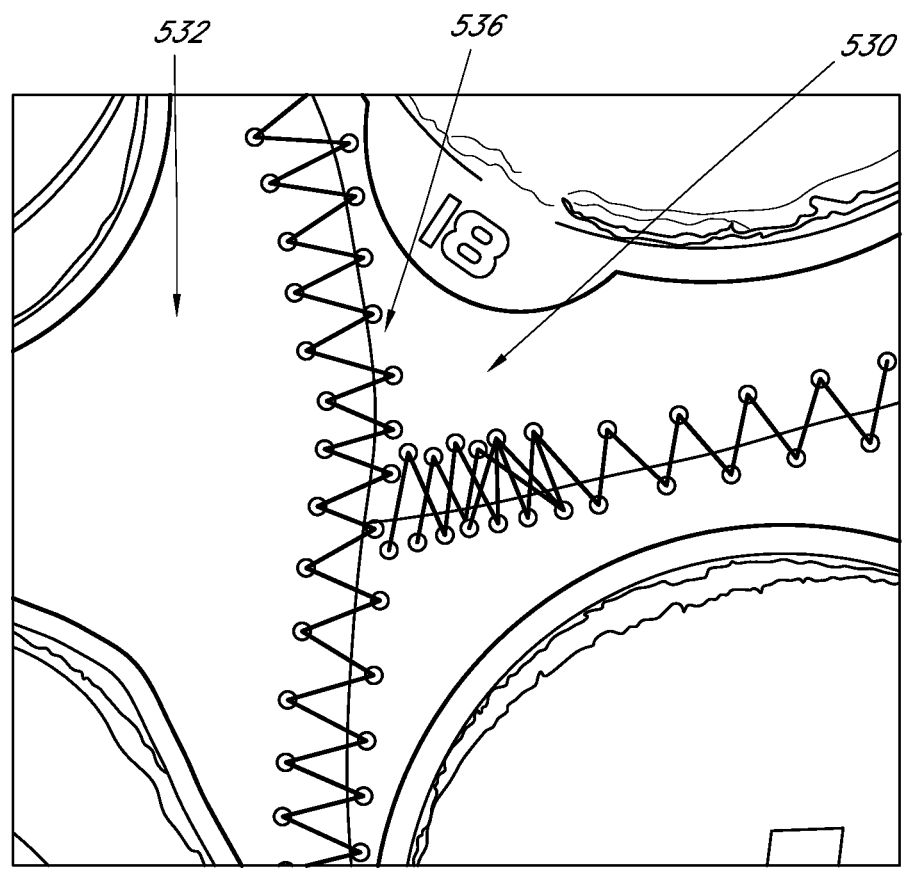

FIG. 23G illustrates a magnified view of a seam 536 between the upper right panel 530 and the lower right panel 532. The panels of the body 510 can comprise Tyvek® material. The Tyvek® panels can be sewn together using a #306 Union Special needle, a #14 Singer needle, or the like. As shown, a panel can comprise one or more separate portions (e.g., portions separated by the slits 534) that are sewn together to form a curved shape from a flat panel. The needle used can be a flat tipped needle or a round-point needle. The stitches can be spaced so as to include three to five stitches per inch. Any suitable thread type can be used (for example, glace thread of short staple cotton). In certain embodiments, the maximum overlap between panels or portions of a panel is about two millimeters and the maximum gap between panels or portions of a panel is about two millimeters. In other embodiments, the panels of the body comprise suitable materials other than Tyvek® material, such as fiber-based (natural and/or synthetic) materials and/or polymeric materials.

Figure 23H:
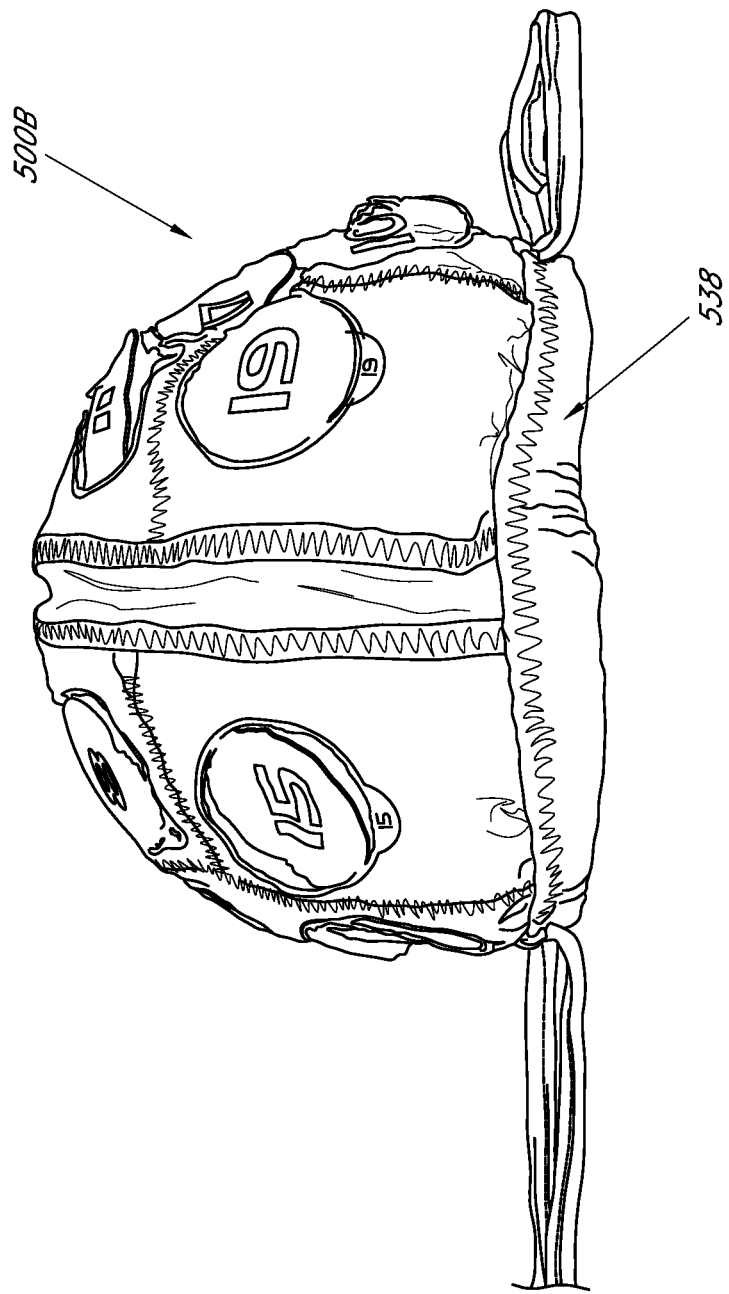

FIG. 23H illustrates a rear view of the wearable apparatus 500B. As shown in FIG. 23H, the wearable apparatus 500B further includes a folded perimeter portion 538 that extends around the bottom of the wearable apparatus 500B. The peripheral portions of the panels can be inserted within the folded perimeter portion 538 and the edges of the folded perimeter portion 538 can be sewn together to retain the panels. The retention assembly 512 can also be attached at the perimeter portion 538. The width of the perimeter portion 538 can be about fifteen millimeters. The perimeter portion 538 can comprise elastic-type material (e.g., an elastic band). The elastic material can be configured to aid in securing the body 510 to the head of the patient and can allow for an adjustable fit for different sized heads.

Figure 23I:
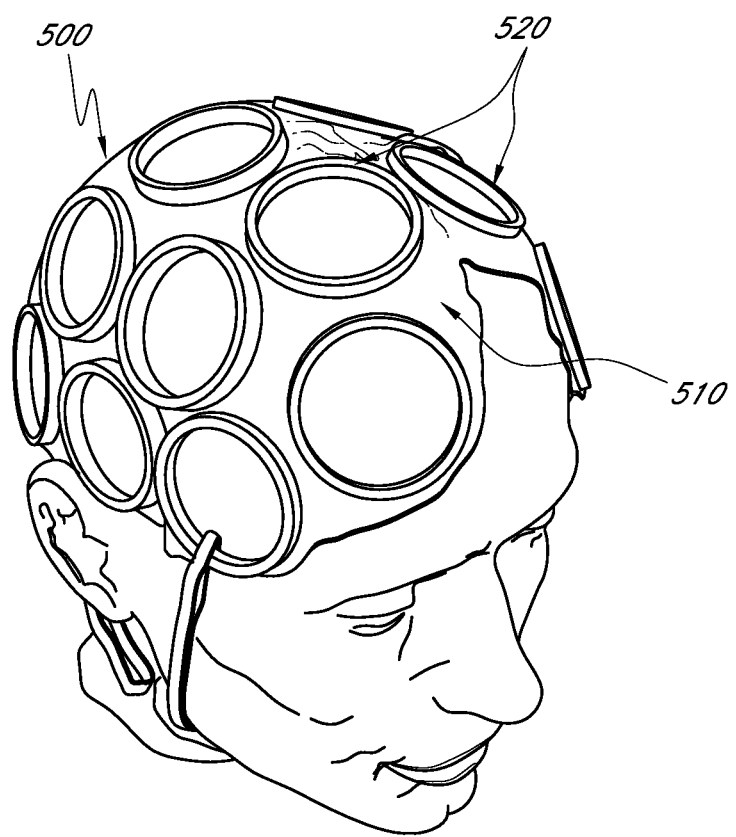
FIGS. 23I-23M illustrate alternative example embodiments of a wearable apparatus for use in treating the patient's brain with phototherapy.

FIG. 23I schematically illustrates another example embodiment of the wearable apparatus 500. The wearable apparatus 500 includes a body 510 and a plurality of position indicators 520. The body 510 can comprise a single, unitary element that is not separated into individual panels. The body 510 can comprise a stretchable or pliant material which generally conforms to the patient's scalp, such as neoprene, chloroprene, rubber, silicone, thermoplastic resins, other elastomeric materials, and/or the like. In other embodiments, the body 510 can be formed of a rigid or substantially rigid material in order to prevent movement during irradiation, such as polyethylene, polystyrene, polyvinyl chloride, polytetrafluoroethylene, other plastic or polymeric materials, and/or the like. In some embodiments, the body 510 comprises one or more biocompatible materials.

The body 510 can advantageously comprise a material that has relatively high thermal conductivity in order to reduce temperature increases to the patient's scalp or skin at locations surrounding the position indicators 520, such as diamond, sapphire, calcium fluoride, and/or the like. The body 510 can have a thickness between one and ten millimeters; however, other thicknesses can be used as desired and/or required.

The position indicators 520 can be coupled to the body 510 using any suitable adhesive or coupling method or device, such as epoxy, sutures, welding, molding, adhesive, interference fits, and/or the like. In certain embodiments, the position indicators 520 can provide indicia of orientation of the wearable apparatus 500 relative to the patient's scalp. For example, the position indicators 520 that cover the right hemisphere of the brain can be a different color than the position indicators 520 that cover the left hemisphere of the brain.

The position indicators 520 can comprise any suitable polymer or combination of polymers, such as thermoplastics, thermosets, and elastomers. The polymers used can be selected based on strength, flexibility, and/or other properties. In certain embodiments, the position indicators 520 can be formed of two or more distinct materials (not shown). For example, an inner member of the position indicators 520 can be formed of one material and an outer member can be formed of another material. The outer member can comprise a material having a lower durometer value than the inner member, or vice-versa.

Figure 23J:
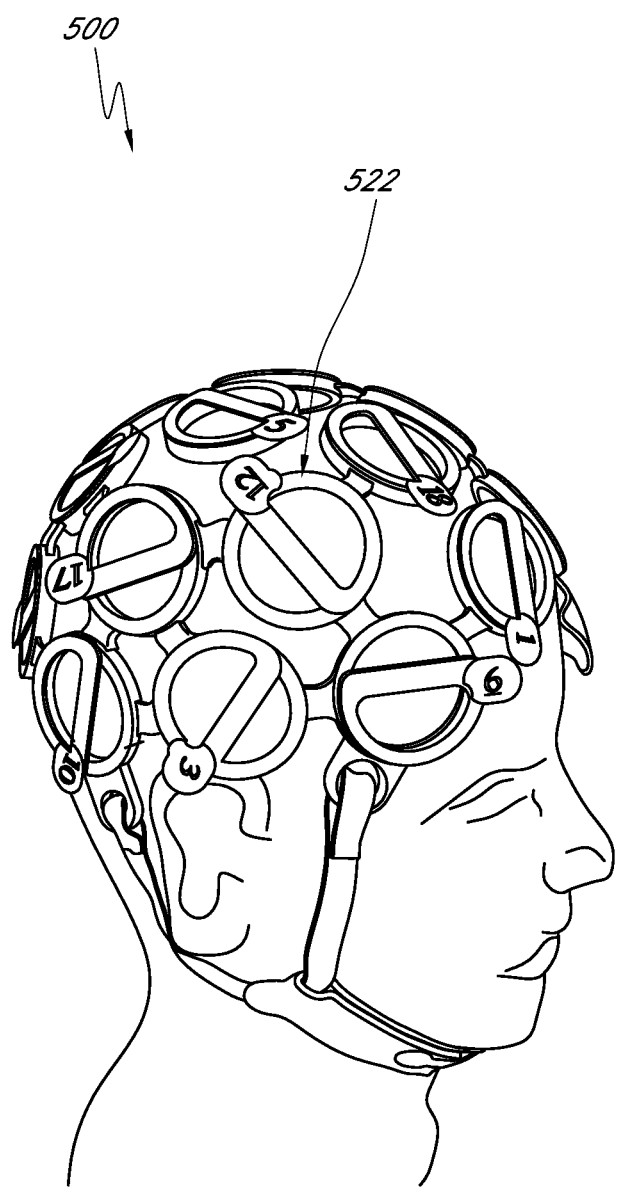

FIG. 23J illustrates another example embodiment of the wearable apparatus 500. In certain embodiments, the wearable apparatus 500 comprises a plurality of labels 522 with each label 522 in proximity to a corresponding position indicator 520. The labels 522 advantageously provide one or more numbers, letters, or symbols (e.g., bar codes) to each of the position indicators 520 to distinguish the various position indicators 520 from one another. Other indicia are possible for the labels 522, such as varying colors, patterns, and the like. In certain such embodiments, the labels 522 are mechanically coupled to the corresponding indicators so as to be visible to users of the light source or light delivery apparatus.

Figure 23K:
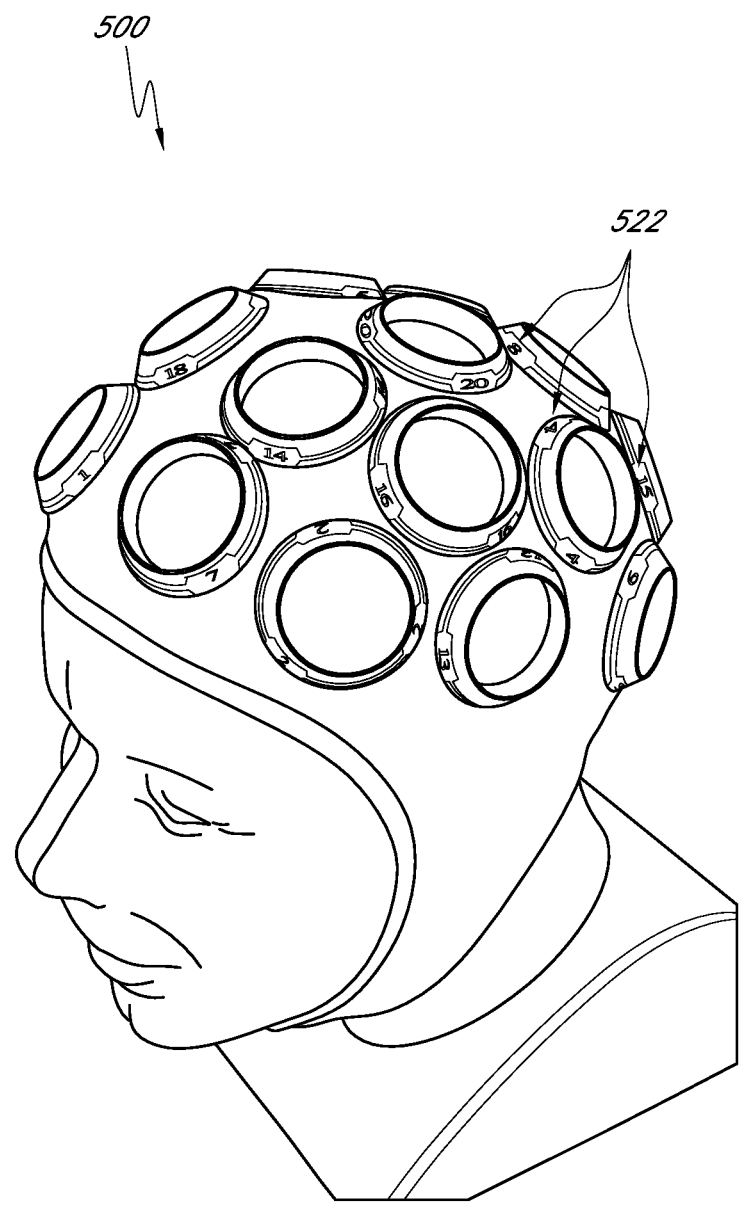

The labels 522 can advantageously be used to keep track of which treatment sites have been irradiated and which treatment sites have yet to be irradiated. The labels 522 can also indicate a sequence of treatment, as described further above in connection with FIGS. 23B-23D. In certain embodiments, the labels 522 can be removable or detachable. For example, a label 522 can be removed from its respective indicator 520 immediately before the treatment site corresponding to the indicator 520 is irradiated. In other embodiments, the labels 522 are integral with the wearable apparatus 500 and are not configured to be removed during treatment, as illustrated by the labels 522 of the wearable apparatus 500 shown in FIG. 23K. The wearable apparatus 500 of FIG. 23K is described in detail in U.S. Pat. Appl. Pub. No. 2007/0179570, which is incorporated by reference herein in its entirety.

In other embodiments, a photochromic layer can be positioned to cover one or more of the treatment sites corresponding to the plurality of position indicators 520. The photochromic layer can be substantially optically transmissive to light used for the phototherapy treatment described herein. In certain embodiments, the photochromic layer can change colors upon being irradiated by light. The photochromic layer can advantageously be used to indicate to a user which treatment sites have been irradiated and which treatment sites have not. In certain embodiments, the photochromic layer comprises one or more photochromic dyes (such as spirooxazines, diarylethenes, axobenzenes, quinones, and the like) and/or silver or zinc halides. Some photochromic dyes can be more biocompatible than others. As such, the biocompatibility of the photochromic dyes can be taken into account in selecting photochromic dyes for use. However, photochromic dyes with low biocompatibility properties can be selected for other reasons that may outweigh biocompatibility. In other embodiments, one or more flexible polymers having low glass transition properties (such as siloxanes or polybutyl acrylate) can be attached to the photochromic dyes. In certain embodiments, the flexible polymers are biocompatible.

Figure 23L:
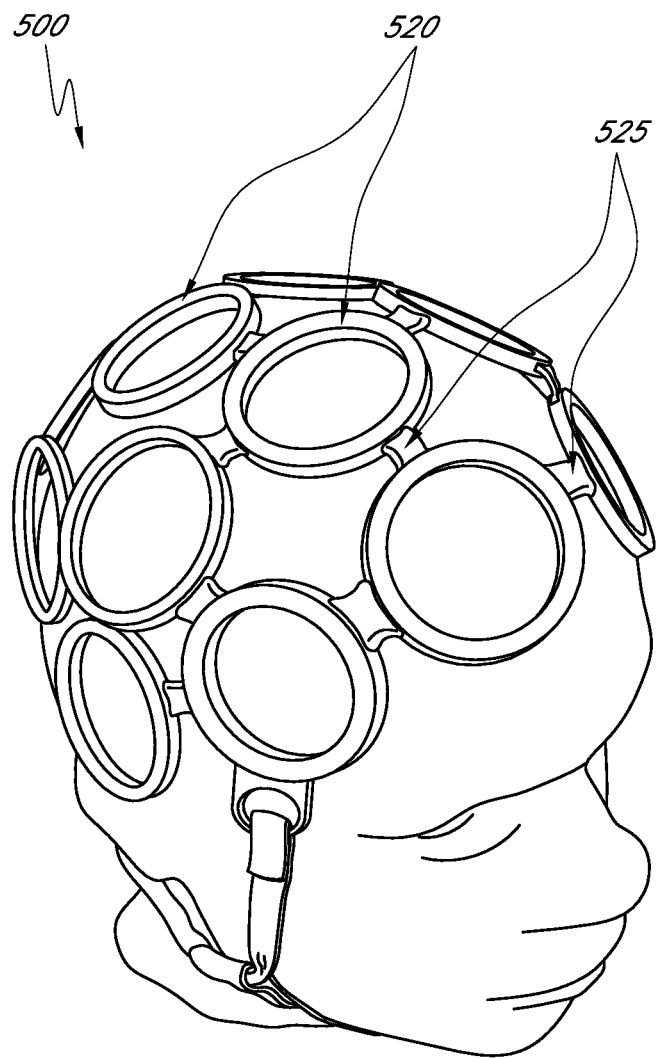

In certain embodiments, the position indicators 520 are connected to each other via coupling joints. FIG. 23L illustrates another example embodiment of the wearable apparatus 500 in which coupling joints 525 mechanically couple the position indicators 520 to one another. The position indicators 520 and the coupling joints 525 can be formed as one integral piece during the molding process. In other embodiments, the position indicators 520 can be coupled together using the coupling joints 525 after the initial molding process. In embodiments where the position indicators 520 are coupled together after the initial molding process, the coupling joints 525 can comprise complementary mating portions that snap together with the position indicators 520 or with each other. In embodiments where the position indicators 520 are formed individually and the wearable apparatus 500 is not formed as an integral unit during the molding process, the position indicators 520 can be connected by string, tether, elastic, adhesive, and/or the like with or without the coupling joints 525. The coupling joints 525 can be formed of the same materials as are the position indicators 520 or of different materials. The use of coupling joints 525 in certain embodiments increases the amount of open space of the wearable apparatus 500, thereby reducing the potential for heat retention within the wearable apparatus 500. The absence of the body 510 in certain embodiments advantageously minimizes the heat loads transferred to the patients' scalp, brain, or skull.

Figure 23M:
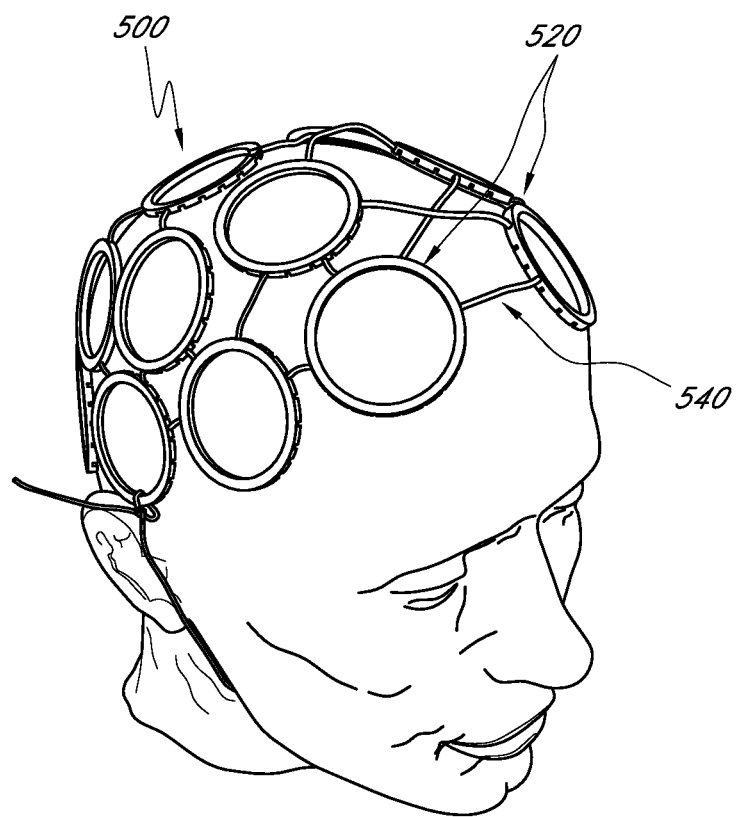

FIG. 23L illustrates an example embodiment of the wearable headpiece wherein the position indicators 520 and the coupling joints 525 are formed as an integral headpiece unit during the molding process. FIG. 23M illustrates an example embodiment of the wearable apparatus 500 in which the position indicators 520 are formed of individual units that are connected together by a tether or connection element 540 (e.g., string) to form the wearable apparatus 500. The embodiment of FIG. 23M can advantageously reduce the cost of manufacture of the wearable apparatus 500.

In certain embodiments, a wearable headpiece can be configured to provide a force to position a light source (e.g., beam delivery apparatus 10) relative to the patient's scalp. In certain embodiments, the wearable headpiece is configured to provide an amount of force which is sufficient to maintain a sufficiently effective interface between the light source and the patient's scalp for one or more of the following: sufficient uniformity across the irradiated area to permit a substantially equal distribution of light to a target region of a patient's brain; sufficient optical communication to permit the light from the light source to propagate to the patient's scalp without an undue amount of absorption or reflection; sufficient thermal communication to permit a substantial amount of heat transport from the patient's scalp to the light source; sufficient pressure applied to the patient's scalp to substantially blanch the irradiated portion of the patient's scalp. For example, the wearable headpiece can provide one or more mating interfaces to "lock" the light source at one or more desired treatment sites, thereby preventing movement of the light source relative to the patient's brain while irradiating the patient's brain with the light source.

In certain embodiments, the force of the "lock" provided by the headpiece is sufficient to hold the light source in place without any additional structures or personnel holding the light source. In certain other embodiments, the force of the "lock" provided by the headpiece is only sufficient to hold the light source in place when used in conjunction with other structures or personnel holding the light source (e.g., supporting the bulk of the weight of the light source). In certain such embodiments, if the other structure or personnel ceased holding the light source, the light source would fall away from the patient's scalp since the force of the "lock" provided by the headpiece alone is insufficient to hold the light source in place. The headpiece can be configured to conform to at least a portion of the patient's head (e.g., scalp and/or forehead). Any of the embodiments illustrated in FIGS. 23A-23M can be adapted to form a wearable headpiece configured to receive a mating portion of a light source or light delivery apparatus.

Figure 24:
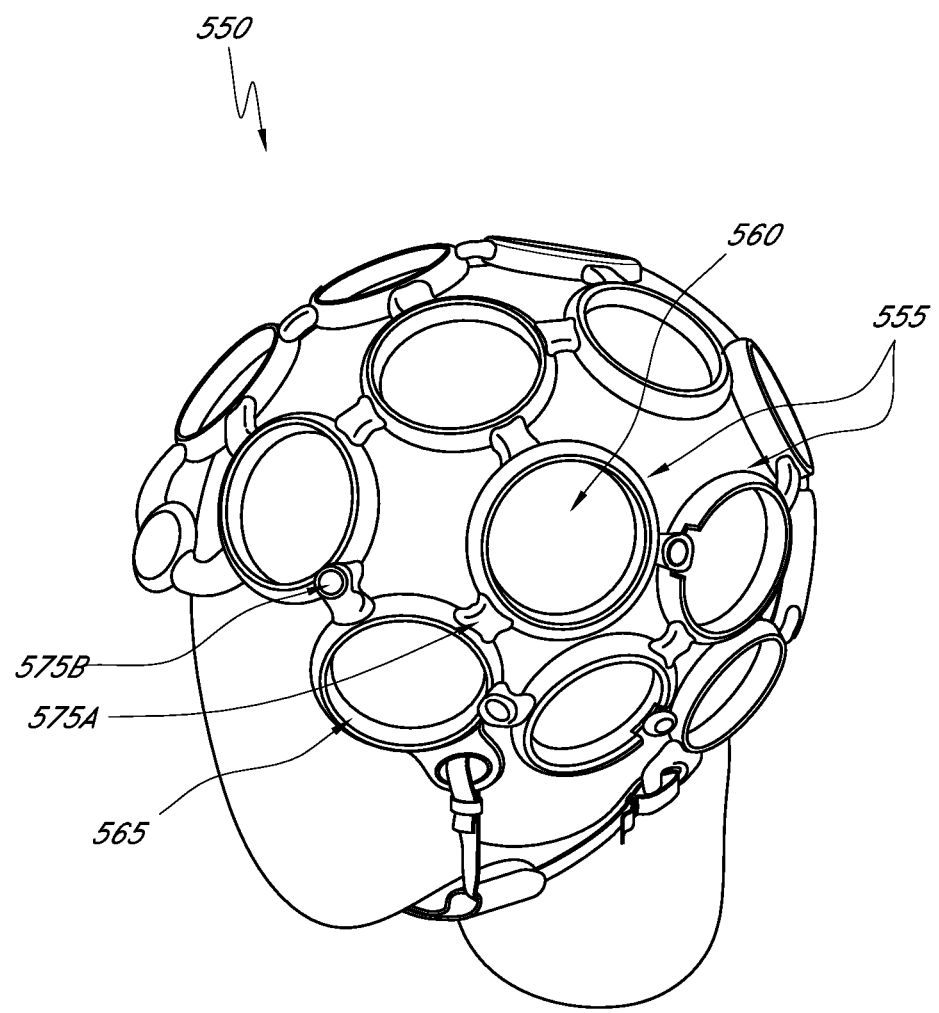
FIG. 24 schematically illustrates an example embodiment of a wearable headpiece that may be configured to position a light delivery apparatus.

FIG. 24 schematically illustrates an example headpiece 550 in accordance with certain embodiments described herein. In certain embodiments, the headpiece 550 is configured to conform to at least a portion of the patient's scalp and comprises a plurality of position indicators 555 configured to indicate corresponding treatment site locations at which light is to be applied to non-invasively irradiate at least a portion of the patient's brain. The plurality of position indicators 555 can be arranged about a patient's head and can be configured to provide a force to position a light source to irradiate a treatment site location. At least one of the position indicators 555 includes an optically transmissive region 560 and a mating portion 565 configured to releasably mate with a complementary mating portion of a light source or a light delivery apparatus.

In certain embodiments, the plurality of position indicators 555 comprises at least three position indicators 555 distributed across the patient's scalp, forehead, and/or neck. In other embodiments, the wearable headpiece 550 comprises between four and thirty position indicators 555. The position indicators 555 can be spaced such that adjacent position indicators 555 have perimeters that do not overlap one another. In certain embodiments, the perimeters are spaced from one another by at least five millimeters, at least ten millimeters or at least twenty-five millimeters. The position indicators 555 can be integrally or mechanically coupled. FIG. 24 illustrates an integral connection 575A and a mechanical connection 575B. In some embodiments, all of the position indicators 555 are integrally coupled. In other embodiments, all of the position indicators 555 are mechanically coupled. The integral connection 575A can be formed, for example, during a molding process during manufacture. The mechanical connection can comprise any suitable mechanical connection device or method, such as snap-fit members, adhesive members, glue, epoxy, welding, interference fits, and/or the like.

In certain embodiments, the optically transmissive region 560 has a substantially circular perimeter and a diameter in a range between twenty millimeters and fifty millimeters or in a range between twenty-five millimeters and thirty-five millimeters. In other embodiments, the optically transmissive region 560 has a substantially elliptical perimeter with a minor axis greater than twenty millimeters and a major axis less than fifty millimeters. Other shapes of the optically transmissive region 560 are also possible. The optically transmissive region 560 can be shaped to conform with the shape of a mating portion of a light delivery apparatus (such as the beam delivery apparatus 10 described herein). In certain embodiments, the optically transmissive region 560 has an area of at least 1 $cm^2$, in a range between 1 $cm^2$ and 20 $cm^2$, or in a range between 5 $cm^2$ and 10 $cm^2$.

The mating portion 565 can comprise any mechanism or structure for releasably mating, or mechanically coupling, with a light delivery apparatus (e.g., any of the light delivery apparatuses described herein). The mating portion 565 can be configured to retain the light delivery apparatus in a substantially fixed position so as to produce a substantially equal distribution of light from an emission surface of the light source to a target region of irradiation. The mating portion 565 can prevent excessive tilting of the light delivery apparatus relative to the patient's scalp during irradiation. In certain embodiments, by maintaining a substantially even contact or spacing between the light delivery apparatus and the patient's skull, the mating portion 565 and can prevent uneven variations in temperature under the emission surface of the light delivery apparatus.

In certain embodiments, the mating portion 565 comprises a rim bordering the outer perimeter of the aperture or opening. The rim can have a height between about one millimeter and about fifteen millimeters. In certain embodiments, the rim can have a height between three and eight millimeters. The rim can act as a positioning sleeve for an optical element of a light delivery apparatus to fit into (e.g., via friction fit).

The mating portion 565 can be formed of rigid, semi-rigid, or flexible material. In certain embodiments, the mating portion 565 is formed of molded plastic. The molded plastic can be composed of any suitable polymer or combination of polymers, such as thermoplastics, thermosets, and elastomers. The polymers used can be selected based on strength, flexibility, and/or other properties. In other embodiments, the mating portion 565 is formed of rubber or other elastomer materials. In certain embodiments, the mating portion 565 can be formed of two or more distinct materials. For example, an inner member of the mating portion 565 can be formed of one material and an outer member can be formed of another material. The outer member can comprise a material having a lower durometer value than the inner member or vice versa.

In certain embodiments, the rim of the mating portion 565 is sized and shaped to reversibly mechanically couple a mating portion of a light delivery apparatus to the mating portion 565 via friction fit. For example, the rim can be sized and shaped to receive, via friction fit, the output optical assembly 20 of the beam delivery apparatus 10 of FIG. 1. In some embodiments, the inner surface of the rim can be textured to enhance engagement between the mating portions of the rim and the light delivery apparatus. In other embodiments, the inner surface of the rim can be formed of a material, such as a rubber or other elastomer, to increase friction with the mating portion of the light delivery apparatus.

In certain embodiments, the rim of the mating portion 565 can be slotted, grooved, notched, indented, recessed or the like to releasably mate with a complementary mating portion (e.g., docking element) of the light delivery apparatus, which may have protrusions, tabs, rivets, or the like. In some embodiments, the rim includes one or more recesses or slots sized and shaped to mate with one or more protrusions formed on the complementary mating portion of the light delivery apparatus. In other embodiments, the rim includes one or more protrusions and the light delivery apparatus includes one or more complementary recesses or slots. In certain embodiments, the complementary mating portion of the light delivery apparatus mates with the mating portion 565 of the position indicator 555 via snap-fit members.

In still other embodiments, the rim of the mating portion 565 can be threaded so as to receive a complementary threaded portion of the light delivery apparatus. Any other suitable means of releasably coupling the light delivery apparatus to the position indicator 555 can be used in accordance with various embodiments described herein.

In alternative embodiments, the position indicators 555 can include a substantially transmissive (e.g., substantially transparent or substantially translucent) bag comprising a flexible material (which can be biocompatible), such as the bags described in connection with FIGS. 22A-22C of U.S. Pat. Appl. Pub. No. 2007/0179570, which is incorporated in its entirety by reference herein. The bags can provide a mating interface between the light delivery apparatus and the surface of the patient's scalp, skin, or skull.

In certain embodiments, the bags can be configured to be raised above the surface of the scalp, skin or skull while the headpiece 550 is worn by the patient so as to prevent heating of the bag by the body prior to treatment. The bag can configured to move to be in thermal communication with the scalp upon the light delivery apparatus being mated to the position indicator 555. For example, the emission surface of the light delivery apparatus can be brought into contact with the bag and the bag can be depressed by the light delivery apparatus to conform to the surface of the patient's scalp, skin, or skull. The bag can be used to ensure even pressure and to reduce air gaps and back reflections. The bag can also prevent uneven temperature fluctuations at the treatment site. In some embodiments, the bag can include pressure sensors to provide an indication of adequate blanching of the treatment site. In other embodiments, pressure sensors can be positioned about the periphery of the position indicators. Any suitable pressure sensor or pressure sensor can be used, including but not limited to, miniature flush diaphragm sensors, flat plate sensors, and/or the like.

In other embodiments, the substantially transmissive bag can be provided with the light delivery apparatus. For example, the substantially transmissive bag can be coupled to a contact/emission surface of the light delivery apparatus and brought into contact with the patient's scalp or skull when inserted within a position indicator 555.

In certain embodiments, the position indicators 555 can be used to provide feedback to an operator of the light delivery apparatus. For example, the light delivery apparatus can include one or more mating sensors that do not allow the light delivery apparatus to be activated until the light delivery apparatus is in sufficient contact with a mating portion 565 of a position indicator 555 of the headpiece 550, which may be indicative of a satisfactory mating condition.

In certain embodiments, the mating sensors comprise pressure sensors (not shown). In other embodiments, the mating sensors comprise proximity sensors. In certain embodiments, the light delivery apparatus comprises four quadrant-spaced sensors, thereby ensuring even pressure of the emission surface against the surface of the patient's scalp or forehead before activation of the output optical element of the light delivery apparatus.

The light delivery apparatus can include one or more LEDs configured to provide an indication to an operator that sufficient contact with the mating portion 565 of a position indicator 555 has occurred. The mating indication can also comprise an audible indication (such as a click or a beep).

In certain embodiments, the light delivery apparatus can be mated (e.g., "locked") to a first position indicator and can then be activated to irradiate a first treatment site corresponding to the first position indicator for a first period of time. The light delivery apparatus can then be removed while the headpiece 550 is still being worn and mated to a second position indicator, with the light delivery apparatus being activated to irradiate a second treatment site corresponding to the second position indicator for a second period of time upon sufficient contact. The process can be repeated for each of the position indicators, as described in more detail herein.

In certain embodiments, the light delivery apparatus is held in the mated position by an external support. The external support can be used to prevent a force from being exerted on the patient's head and/or neck due to the weight of the light delivery apparatus. The external support can be provided whether the body 510 and/or the mating portion 565 is rigid or flexible. In certain embodiments, the external support is provided by the hand of a person administering the treatment. In other embodiments, the external support is provided by an external support structure that provides a force to maintain the light delivery apparatus in a mated position (e.g., a wall, a tension and/or anchor system, etc.). In still other embodiments, the light delivery apparatus is provided by a mechanism that introduces little or no load to the patient's head and/or neck, such as a mechanical arm that extends from a structure that is fixed to a wall, ceiling, or floor. In yet other embodiments, the light delivery apparatus is substantially lightweight such that no external support is required.

In certain embodiments, the mating portion 565 is configured such that the light delivery apparatus is automatically released from the mating portion 565 when the external support is removed. For example, if a person administering the treatment accidentally lets go of the light delivery apparatus during the treatment procedure, the mated light delivery apparatus can be automatically released or disconnected from the mating portion 565 to avoid the exertion of unwanted force on the patient's head and/or neck or on the wearable headpiece 550 itself.

In certain embodiments, the light delivery apparatus can automatically shut off, or terminate, delivery of light when a loss of support (or an excessive load) is detected. The loss of external support can be detected by one or more pressure, touch, force, and/or light sensors, detectors, and/or transducers, for example. In other embodiments, the mating/locking mechanism is released or disconnected if an angle of incidence deviates beyond a predetermined threshold angle. The automatic release and/or termination of light delivery can be implemented whether support is provided externally or by the wearable headpiece 550 itself. Such sensors can comprise a dead-man's switch, a kill switch, or other safety device or mechanism.

Methods of Light Delivery

FIGS. 25-28 are flow diagrams of example methods for irradiating a surface with light. As described more fully below, the methods are described by referring to the beam delivery apparatus 10 and components thereof, as described herein. Other configurations of a beam delivery apparatus are also compatible with the methods in accordance with embodiments described herein.

Figure 25:
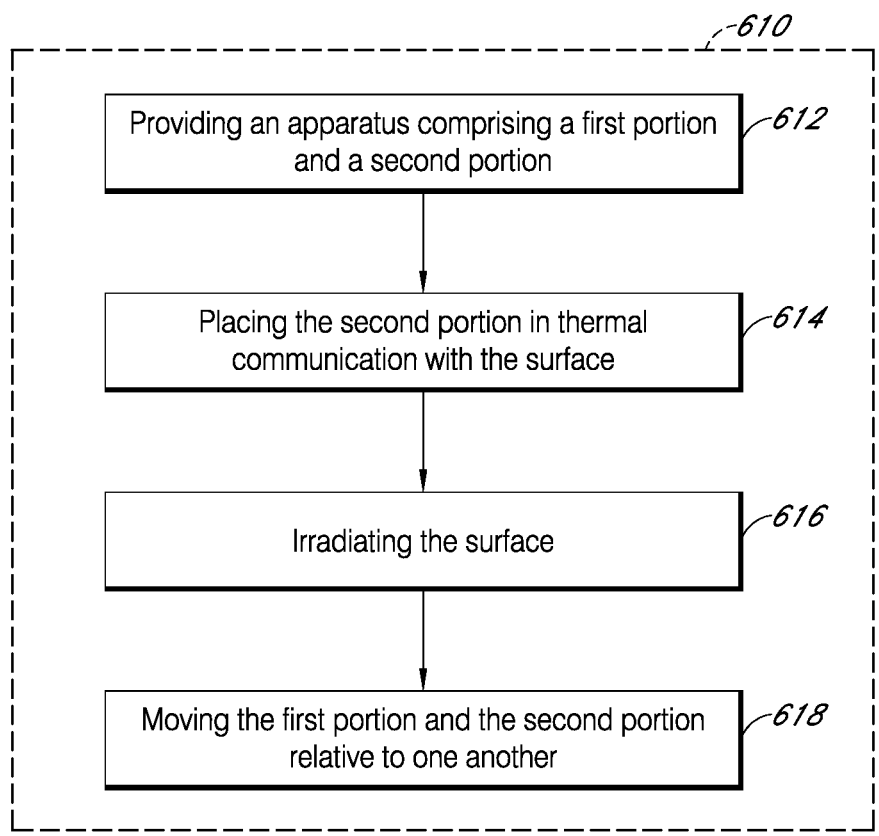
FIGS. 25-28 are flow diagrams of example methods for irradiating a surface with light.

The method 610 of FIG. 25 comprises providing a beam delivery apparatus 10 in an operational block 612. The beam delivery apparatus 10 comprises a first portion and a second portion mechanically coupled to the first portion and in optical communication with the first portion, wherein the first portion and the second portion are configured to move relative to one another, as described more fully above. The method 610 further comprises placing the second portion in thermal communication with the surface in an operational block 614 (e.g., releasably operatively coupling the second portion to the surface). The method 610 further comprises irradiating the surface such that the light from the first portion propagates through the second portion in an operational block 616. The method 610 further comprises moving the first portion and the second portion relative to one another in response to the second portion being placed in thermal communication with the surface in an operational block 618.

Figure 26:
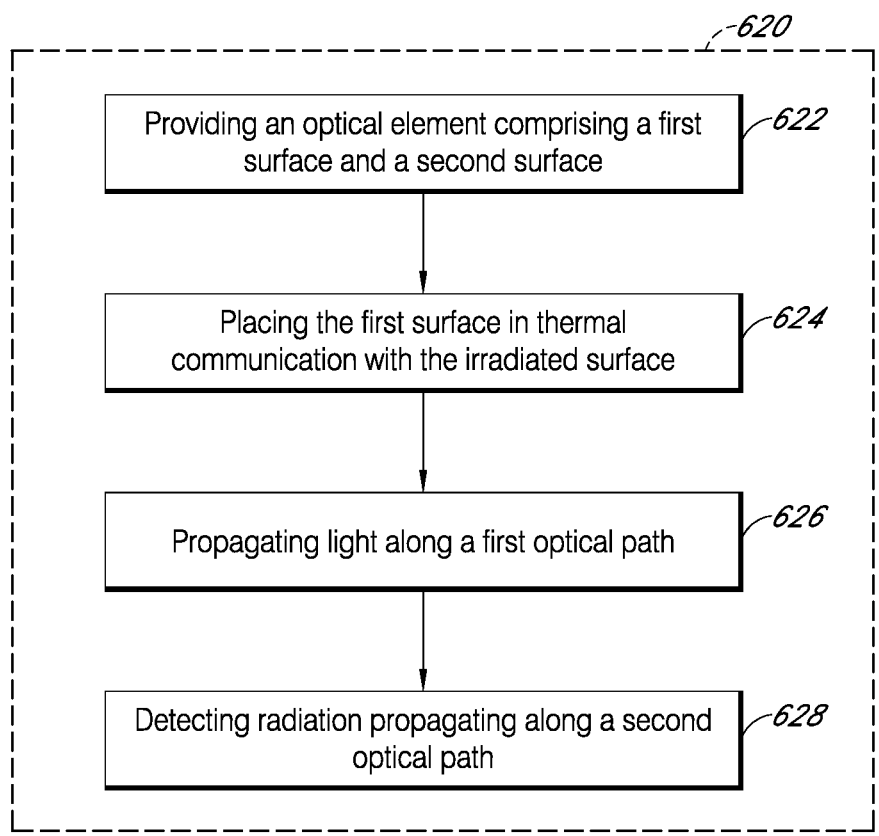

The method 620 of FIG. 26 comprises providing an optical element 23 in an operational block 622. The optical element 23 comprises a substantially optically transmissive and substantially thermally conductive material, and the optical element 23 has a first surface 22 and a second surface 24, as described more fully above. The method 620 further comprises placing the first surface 22 in thermal communication with the irradiated surface in an operational block 624 (e.g., releasably operatively coupling the first surface 22 to the irradiated surface). The method 620 further comprises propagating the light along a first optical path 32 through the second surface 24 and through the first surface 22 to the irradiated surface in an operational block 626. The method 620 further comprises detecting radiation propagating along a second optical path 82 from at least a portion of the second surface 24, wherein the first optical path 32 and the second optical path 82 have a non-zero angle therebetween in an operational block 628. In certain embodiments, the first surface 22 and the second surface 24 face in generally opposite directions, and the first surface 22 is not along the second optical path 82.

Figure 27:
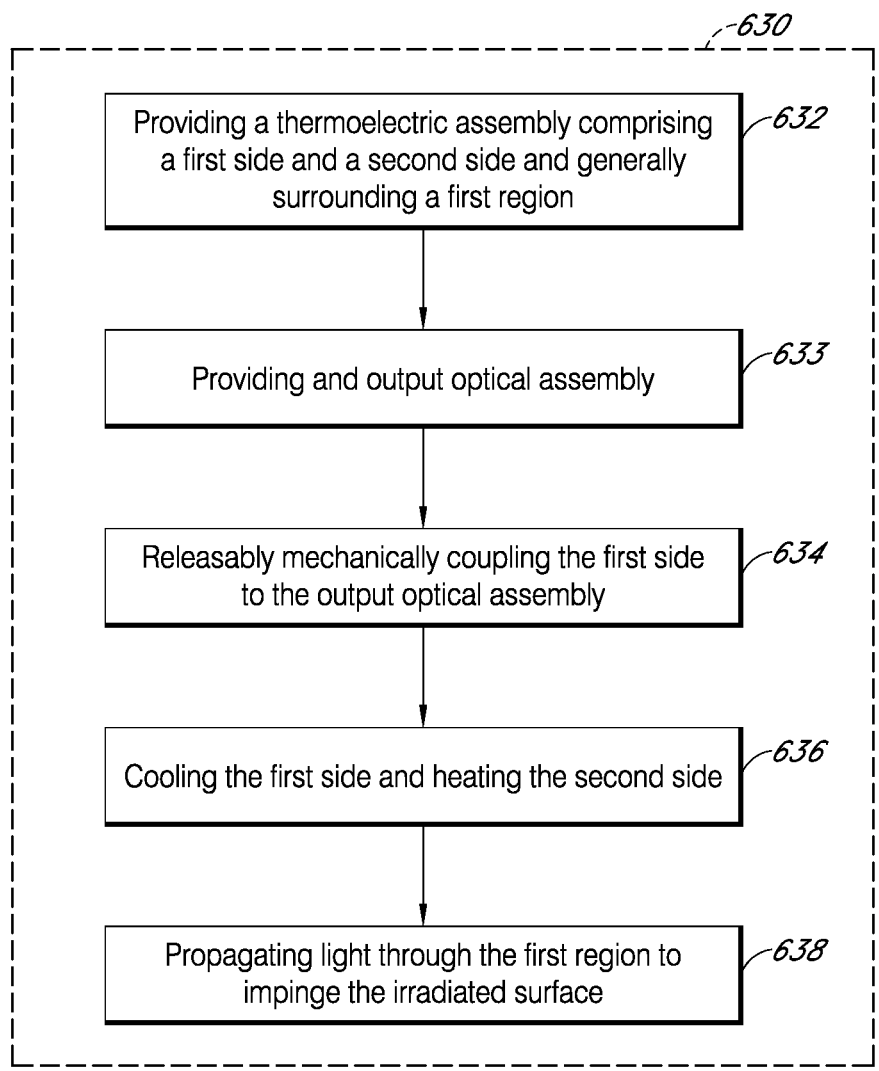

The method 630 of FIG. 27 comprises providing a thermoelectric assembly 90 in an operational block 632. The thermoelectric assembly 90 comprises a first surface 93 and a second surface 94, and the thermoelectric assembly 90 generally surrounds a first region 97, as described more fully above. The method 630 further comprises providing an output optical assembly 20 in an operational block 633. The method 630 further comprises releasably mechanically coupling the first surface 93 of the thermoelectric assembly 90 to the output optical assembly 20 so that the first surface 93 is in thermal communication with the output optical assembly 20 in an operational block 634. The method 630 further comprises cooling the first surface 93 and heating the second surface 94 in an operational block 636. The method 630 further comprises propagating light through the first region 97 to impinge the irradiated surface in an operational block 638. In certain embodiments, the first surface 22 and the second surface 24 face in generally opposite directions, and the first surface 22 is not along the second optical path 82.

In certain embodiments, the output optical assembly 20 comprises an optical element 23 and a thermally conductive portion 25 generally surrounding a second region 28. The thermally conductive portion 25 is in thermal communication with the optical element 23. In certain such embodiments, releasably mechanically coupling the first surface 93 to the output optical assembly 20 comprises releasably mechanically coupling the first surface 93 to the thermally conductive portion 25. In certain such embodiments, the method 630 further comprises placing the optical element 23 in thermal communication with the irradiated surface and propagating the light comprises transmitting the light through the first region 97, the second region 28, and the optical element 23 to impinge the irradiated surface. In certain embodiments, the method 630 further comprises providing a heat sink 100 in thermal communication with the second surface 94 of the thermoelectric assembly 90. The heat sink 100 generally surrounds a third region 107, and propagating the light comprises transmitting the light through the third region 107, the first region 97, the second region 28, and the optical element 23.

Figure 28:
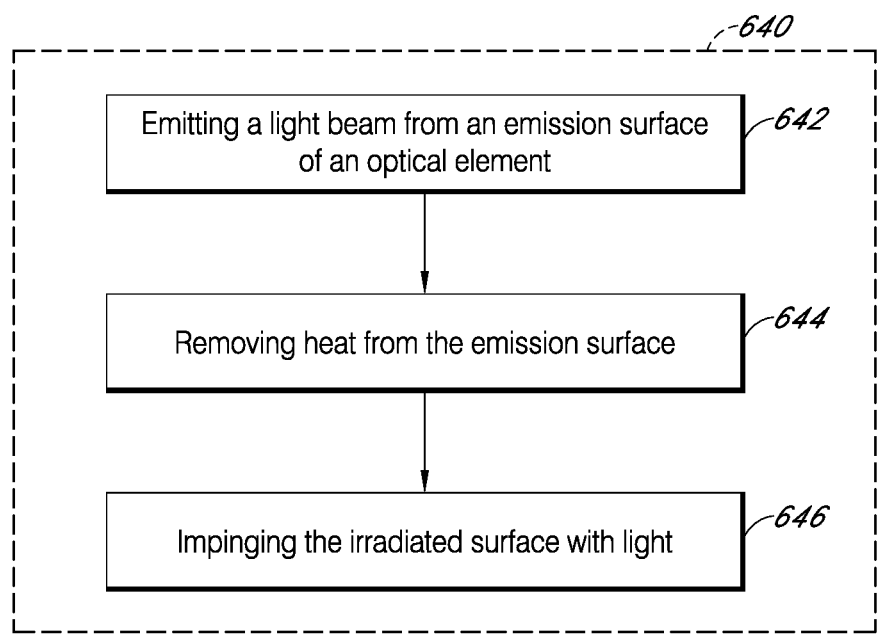

The method 640 of FIG. 28 comprises emitting a light beam from an emission surface 22 of an optical element 23 in an operational block 642. The light beam at the emission surface 22 has one or more wavelengths in a range of about 630 nanometers to about 1064 nanometers, a cross-sectional area greater than about 2 cm$^2$, and a time-averaged irradiance in a range of about 10 mW/cm$^2$ to about 10 W/cm$^2$ across the cross-sectional area, as described more fully above. The method 640 further comprises removing heat from the emission surface 22 at a rate in a range of about 0.1 Watt to about 5 Watts in an operational block 644. The method 640 further comprises impinging the irradiated surface with the light beam in an operational block 646.

The method 640 of certain embodiments further comprises placing the emission surface 22 in thermal communication with the irradiated surface (e.g., using the emission surface 22 to apply pressure to the irradiated surface by applying a force to the emission surface 22 in a direction generally towards the irradiated surface, the pressure greater than about 0.1 pound per square inch or about equal to 2 pounds per square inch).

In certain embodiments, impinging the irradiated surface with the light beam is performed for a time period of 10 seconds to two hours, for a time period of 60 seconds to 600 seconds, or for a time period of about 120 seconds. In certain embodiments, the steps of the operational blocks 642, 644, and 646 are performed concurrently. The method 640 of certain embodiments further comprises moving the emission surface 22 from a first position at which a first portion of the irradiated surface is impinged by the light beam to a second position, and repeating the steps of the operational blocks 642, 644, and 646 so as to impinge a second portion of the irradiated surface by light emitted from the emission surface 22. The first portion and the second portion do not overlap one another in certain embodiments. This method can be repeated so as to impinge twenty portions of the irradiated surface by light emitted from the emission surface 22. In certain such embodiments, the twenty portions of the irradiated surface do not overlap one another. However, the portions of the patient's brain irradiated by impinging these twenty portions of the patient's scalp do overlap one another in certain embodiments.

The irradiated surface of certain embodiments of the methods described above in reference to FIGS. 25-28 comprises a portion of the patient's scalp or skull. In certain other embodiments, the surface irradiated by the light comprises a portion of a light-detection system configured to measure one or more parameters of light irradiating the surface (e.g., irradiance, total power, beam size, beam profile, beam uniformity). In certain such embodiments, the method further comprises measuring the one or more parameters of the light from the apparatus 10 impinging the surface. For example, the light-detection system can comprise a portion of the apparatus 10 configured to test the light beam emitted from the emission surface 22 immediately prior to treatment of the patient. In this way, the light-detection system can be used to ensure that the light beam applied to the patient's scalp or skull has the desired treatment parameters.

In certain embodiments, a patient is treated by identifying a plurality of treatment sites (e.g., at least about 10) on the patient's scalp or skull, directing a light beam to each of the treatment sites, and irradiating each treatment site with the light beam. As described more fully below, in certain embodiments, the treatment sites are identified using an apparatus comprising a plurality of indicators, each of which corresponds to a treatment site location. In certain such embodiments, the treatment sites are sequentially irradiated by a light beam from the emission surface. In certain other embodiments, the treatment sites are instead identified by other indicia. For example, each of the treatment sites can be identified by markings made on the scalp, or by structures placed in proximity to the scalp or skull. Each of the treatment sites can then be irradiated. In certain embodiments, each of the treatment sites is irradiated by a light beam from the emission surface while the emission surface is in contact with the scalp or skull or in contact with an intervening optically transmissive element which contacts the scalp or skull. In certain other embodiments, the scalp or skull is not contacted by either the emission surface or an intervening element. In certain embodiments, each of the treatment sites is irradiated using a single beam delivery apparatus which is sequentially moved from one treatment site to another. In certain other embodiments, a plurality of beam delivery apparatuses are used to irradiate multiple treatment sites concurrently. In certain such embodiments, the number of beam delivery apparatuses is fewer than the number of treatments sites, and the plurality of beam delivery apparatuses are sequentially moved to sequentially irradiate the treatment sites.

Figure 29A:
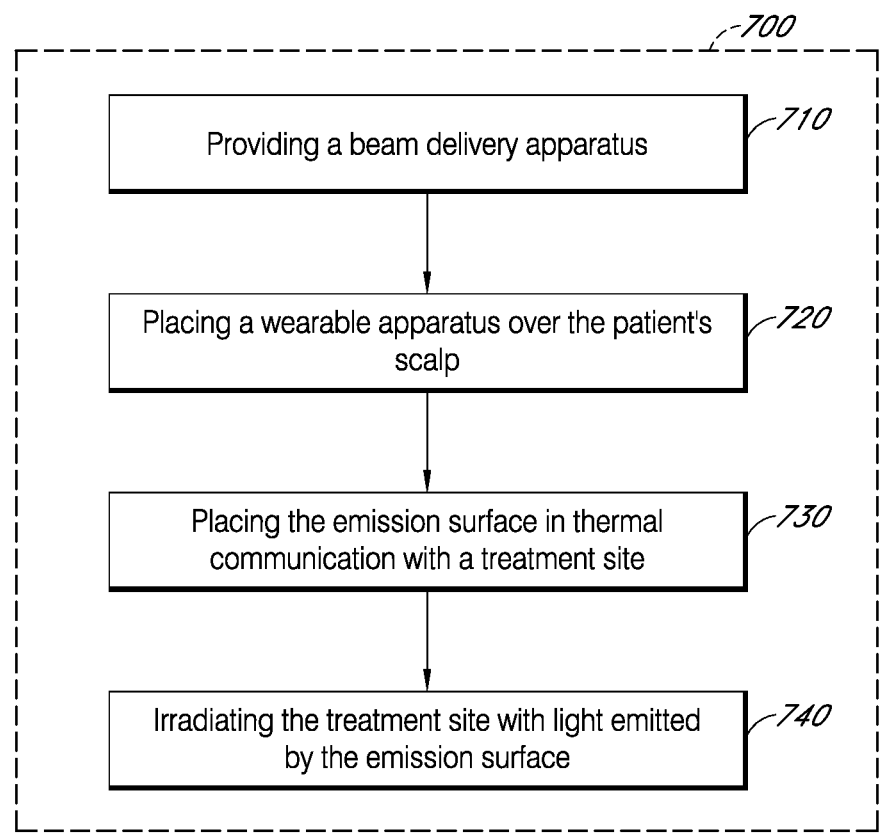
FIG. 29A is a flow diagram of an example method for controllably exposing at least one predetermined area of a patient's scalp to laser light to irradiate the patient's brain.

FIG. 29A is a flow diagram of an example method 700 for controllably exposing at least one predetermined area of a patient's scalp or skull to laser light to irradiate the patient's brain. As described more fully below, the method 700 is described by referring to the wearable apparatus 500 and the beam delivery apparatus 10 described herein. Other configurations of a wearable apparatus 500 and a beam delivery apparatus 10 are also compatible with the method 700 in accordance with embodiments described herein.

The method 700 comprises providing a beam delivery apparatus 10 in an operational block 710. In certain embodiments, the beam delivery apparatus 10 comprises an emission surface 22 configured to emit a light beam. Other configurations of the beam delivery apparatus 10 besides those described above are also compatible with certain embodiments described herein.

The method 700 further comprises placing a wearable apparatus 500 over the patient's scalp in an operational block 720. The apparatus 500 comprises a body 510 and a plurality of indicators 520. In certain embodiments, each indicator 520 is substantially transmissive to the light beam emitted from the emission surface 22. Other configurations of the wearable apparatus 500 besides those described above are also compatible with certain embodiments described herein.

The method 700 further comprises placing the emission surface 22 in thermal communication with a treatment site of the patient's scalp or skull to be irradiated in an operational block 730. The method 700 further comprises irradiating the treatment site with light emitted by the emission surface 22 in an operational block 740. In certain embodiments, the light beam is transmitted through the indicator 520.

In certain embodiments, providing the light emitting apparatus 600 in the operational block 710 comprises preparing the beam delivery apparatus 10 for use to treat the patient. In certain embodiments, preparing the beam delivery apparatus 10 comprises cleaning the portion of the beam delivery apparatus 10 through which laser light is outputted. In certain embodiments, preparing the beam delivery apparatus 10 comprises verifying a power calibration of laser light outputted from the beam delivery apparatus 10. Such verification can comprise measuring the light intensity output from the beam delivery apparatus 10 and comparing the measured intensity to an expected intensity level.

In certain embodiments, placing the wearable apparatus 500 over the patient's scalp in the operational block 720 comprises preparing the patient's scalp for treatment. For example, in certain embodiments, preparing the patient's scalp for treatment comprises removing hair from the predetermined areas of the patient's scalp to be irradiated. Removing the hair (e.g., by shaving) advantageously reduces heating of the patient's scalp by hair which absorbs laser light from the beam delivery apparatus 10. In certain embodiments, placing the wearable apparatus 500 over the patient's scalp in the operational block 720 comprises positioning the wearable apparatus 500 so that each indicator 520 is in position to indicate a corresponding portion of the patient's scalp or skull to be irradiated.

In certain embodiments, placing the emission surface 22 in thermal communication with the treatment site in the operational block 730 comprises pressing the emission surface 22 to the treatment site. In certain embodiments, by pressing the emission surface 22 against the treatment site in this way, pressure is applied to the portion of the patient's scalp of the treatment site so as to advantageously blanch the portion of the patient's scalp to be irradiated.

In certain embodiments, irradiating the treatment site of the patient's scalp or skull in the operational block 740 comprises triggering the emission of light from the emission surface 22 by pressing the emission surface 22 against the treatment site with a predetermined level of pressure. In certain embodiments, the emission of light from the emission surface 22 continues only if a predetermined level of pressure is maintained by pressing the emission surface 22 against the treatment site. In certain embodiments, light is emitted from the emission surface 22 to the treatment site for a predetermined period of time.

In certain embodiments, the method further comprises irradiating additional treatment sites of the patient's scalp or skull during a treatment process. For example, after irradiating a first treatment site corresponding to a first indicator, as described above, the emission surface 22 can be placed in contact with a second indicator corresponding to a second treatment site and irradiating the second treatment site with light emitted by the emission surface 22. The various treatment sites of the patient's scalp or skull can be irradiated sequentially to one another in a predetermined sequence. In certain embodiments, the predetermined sequence is represented by the indicators of the wearable apparatus 500. In certain such embodiments, the beam delivery apparatus 10 comprises an interlock system which interfaces with the indicators of the wearable apparatus 500 to prevent the various treatment sites from being irradiated out of the predetermined sequence.

Figure 29B:
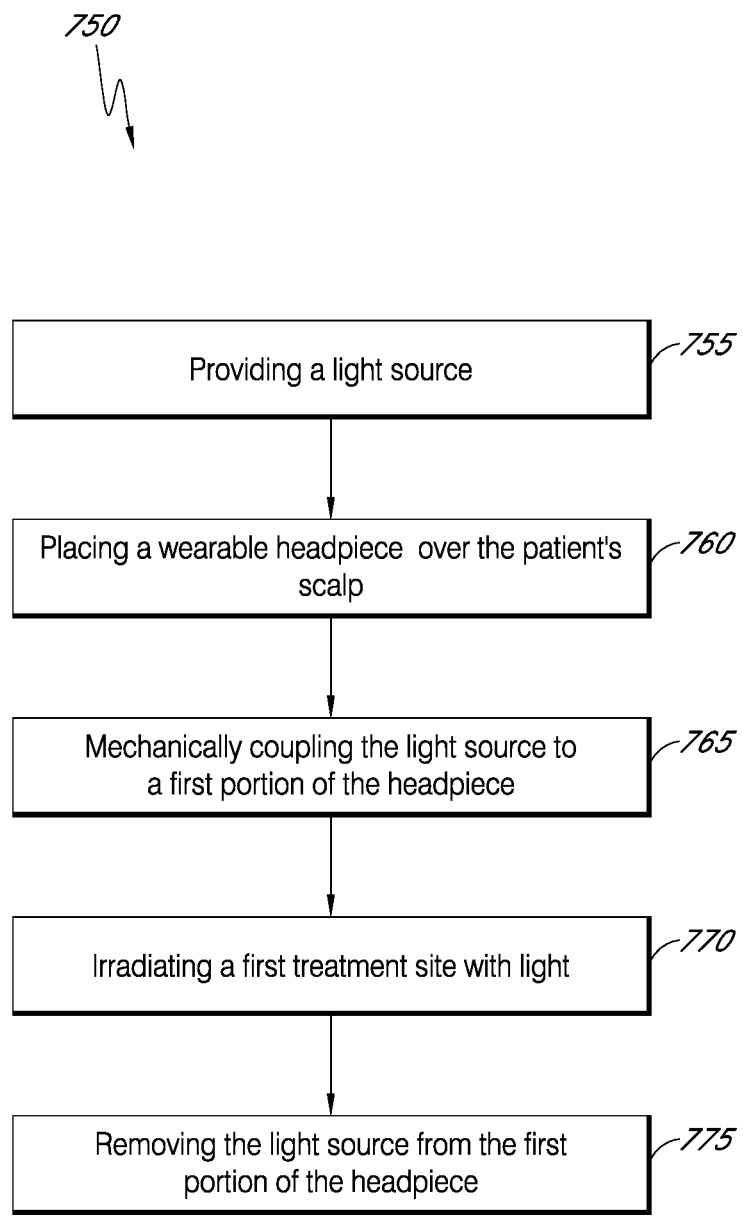
FIG. 29B is a flow diagram of an example method for providing phototherapy to at least a portion of a patient's brain using a wearable headpiece.

FIG. 29B is a flow diagram of an example method 750 for providing phototherapy to at least a portion of a patient's brain. As described more fully below, the method 750 is described by referring to the wearable headpiece 550 and a light source (e.g., the beam delivery apparatus 10) described herein. Other configurations of a wearable headpiece 550 and a light source are also compatible with the method 750 in accordance with embodiments described herein.

The method 750 comprises providing a light source (e.g., beam delivery apparatus 10) in an operational block 755. In certain embodiments, the light source comprises an emission surface configured to emit a light beam.

The method 750 further comprises placing a wearable headpiece 550 over the patient's scalp in an operational block 760. The headpiece 550 comprises a plurality of position indicators 555. In certain embodiments, at least one of the position indicators 555 includes an optically transmissive region that is substantially transmissive to the light emitted from the emission surface of the light source and a mating portion that is configured to releasably mate with a complementary portion of the light source. Other configurations of the wearable headpiece 550 besides those described above are also compatible with certain embodiments described herein.

The method 750 further comprises reversibly mechanically coupling the light source to a first portion of the headpiece 550 while the headpiece 550 is on the patient's head in an operational block 765. The mechanical coupling can occur via friction fit, threading, snap-fit members, or any other suitable coupling means. The method 750 further comprises irradiating a first treatment site with light emitted by the emission surface of the light source while the light source is mechanically coupled to the first portion of the headpiece 550 in an operation block 770. The first portion of the headpiece 550 applies a first force to the light source such that light emitted by the light source non-invasively irradiates at least a first portion of the patient's brain by propagating through the first treatment site of the patient's scalp.

The method 750 further comprises decoupling the light source from the first portion of the headpiece 550 while the headpiece 550 remains on the patient's head in an operational block 775. In certain embodiments, the method 750 further comprises irradiating additional treatment sites of the patient's scalp or skull during a treatment process. For example, operational blocks 765 through 775 can be repeated at a second portion of the headpiece 550 by reversibly mechanically coupling the light source to a second portion of the headpiece 550 while the headpiece 550 is on the patient's head, wherein the headpiece 550 applies a second force to the light source such that light emitted by the light source while the light source is mechanically coupled to the second portion of the headpiece 550 non-invasively irradiates at least a second portion of the patient's brain by propagating through a second treatment site of the patient's scalp and then decoupling the light source from the second portion of the headpiece 550 while the headpiece 550 remains on the patient's head.

In certain embodiments, the first portion of the patient's brain and the second portion of the patient's brain at least partially overlap one another and the first treatment site and the second treatment site do not at least partially overlap one another. In certain embodiments, the first portion of the headpiece 550 is a first position indicator 555 and the second portion of the headpiece 550 is a second position indicator 555.

In certain embodiments, the method 750 comprises verifying (e.g., through the use of pressure sensors) that a sufficient pressure exists between a mating portion of the light source and the first portion of the headpiece 550 before irradiating the first treatment site at operational block 770. In other embodiments, multiple light sources can be reversibly mechanically coupled to portions of the headpiece 550 simultaneously.

Figure 30:
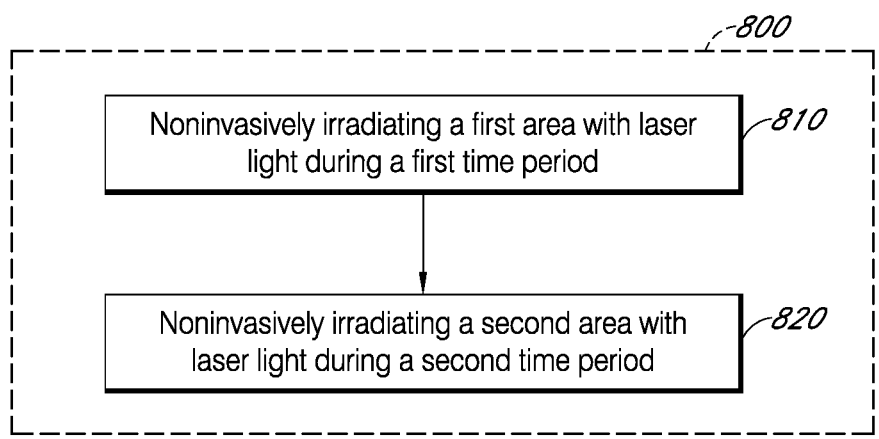
FIG. 30 is a flow diagram of another example method for treating a patient's brain.

FIG. 30 is a flow diagram of another example method 800 for treating a patient's brain. The method 800 is described below by referring to the wearable apparatus 500 and the beam delivery apparatus 10 described herein. Other configurations of a wearable apparatus 500 and a beam delivery apparatus 10 are also compatible with the method 700 in accordance with embodiments described herein.

The method 800 comprises noninvasively irradiating a first area of at least 1 cm² of the patient's scalp or skull with laser light during a first time period in an operational block 810. The method 800 further comprises noninvasively irradiating a second area of at least 1 cm² of the patient's scalp or skull with laser light during a second time period in an operational block 820. The first area and the second area do not overlap one another, and the first time period and the second time period do not overlap one another. In certain embodiments, the first area and the second area are spaced from one another by at least 10 millimeters. In certain embodiments, the first area is over a first hemisphere of the brain, and the second area is over a second hemisphere of the brain.

In certain embodiments, the method 800 further comprises identifying the first area and the second area by placing a template over the patient's scalp. The template comprises a first indicator of the first area and a second indicator of the second area. For example, the first indicator can comprise a first opening in the template and the second indicator can comprise a second opening in the template. In certain embodiments, the method 800 further comprises placing a laser light source at a first position to noninvasively irradiate the first area and moving the laser light source to a second position to noninvasively irradiate the second area.

In certain embodiments, the method 800 further comprises increasing the transmissivity of the first area to the laser light and increasing the transmissivity of the second area to the laser light. Increasing the transmissivity of the first area can comprise applying pressure to the first area to at least partially blanch the first area, removing hair from the first area prior to noninvasively irradiating the first area, applying an index-matching material to the first area, or a combination of two or more of these measures. Increasing the transmissivity of the second area can comprise applying pressure to the second area to at least partially blanch the second area, removing hair from the second area prior to noninvasively irradiating the second area, applying an index-matching material to the second area, or a combination of two or more of these measures.

FIG. 38 is a flow diagram of an example method 900 for treating a patient's brain in accordance with certain embodiments described herein. The method 900 comprises providing a patient in an operational block 910 whose brain has experienced at least one neurologic disorder (e.g., Alzheimer's Disease, Parkinson's Disease, Huntington's disease, depression) or physical trauma (e.g., an ischemic stroke or a traumatic brain injury) resulting in a blood flow reduction to at least some brain cells of the patient. The method 900 further comprises irradiating at least a portion of the patient's scalp or skull with a pulsed light beam comprising a plurality of pulses transmitted through the patient's skull in an operational block 920. The pulsed light beam has a temporal profile which supports one or more intercellular or intracellular biological processes involved in the survival or regeneration of brain cells. For example, the pulsed light beam of certain embodiments comprises an average irradiance per pulse and a temporal profile comprising a temporal pulse width and a duty cycle sufficient to penetrate the skull to modulate membrane potentials, thereby enhancing cell survival (e.g., to cause increased neuron survival), cell function, or both of the irradiated brain cells.

In certain embodiments, providing the patient comprises identifying a patient whose brain has experienced at least one neurologic disorder or physical trauma. In certain such embodiments, identifying the patient comprises communicating with the patient, or with another person with knowledge regarding the patient's health or experiences, and determining whether the patient has experienced a neurologic disorder or a physical trauma to the brain. In certain other embodiments, identifying the patient comprises examining the patient's body (e.g., head or skull) for evidence of the patient having experienced a physical trauma to the brain. This examination in certain embodiments includes use of invasive or non-invasive medical devices, techniques, or probes (e.g., a magnetic resonance imaging device). In certain other embodiments, identifying the patient comprises administering a test of the patient's mental faculties (e.g., to determine the patient's abilities on a neurologic function scale) for evidence indicating that the patient has experienced a neurologic disorder or a physical trauma to the brain. Persons skilled in the art are able to identify the patient in accordance with various embodiments described herein. In certain embodiments, providing the patient comprises receiving information regarding the results of a previous identification (e.g., communication, examination, or test administration) of the patient as one who has experienced at least one neurologic disorder or physical trauma.

In certain embodiments, irradiating at least a portion of the patient's scalp or skull with a pulsed light beam comprises generating the pulsed light beam and directing the pulsed light beam to irradiate at least a portion of the patient's scalp or skull. The pulsed light beam of certain embodiments has a wavelength, time-averaged irradiance, beam size, beam profile, divergence, temporal pulse width, duty cycle, repetition rate, and peak irradiance per pulse, as described herein. Various light delivery apparatuses can be used to generate the pulsed light beam and to direct the pulsed light beam towards the patient's scalp or skull, including but not limited to, the apparatus disclosed herein or by U.S. Pat. Nos. 6,214,035; 6,267,780; 6,273,905; 6,290,714; 7,303,578; and 7,575,589 and in U.S. Pat. Appl. Publ. Nos. 2005/0107851 A1 and 2009/0254154 A1, each of which is incorporated in its entirety by reference herein.

In certain embodiments, irradiating at least a portion of the patient's scalp or skull comprises identifying one or more treatment sites (e.g., at least 10, between 2 and 100, or between 15 and 25) and sequentially irradiating the treatment sites with the pulsed light beam. In certain embodiments, the one or more treatment sites are identified as described herein (e.g., by an apparatus worn by the patient and comprising one or more apertures, by markings made on the scalp, or by structures placed in proximity to the scalp or skull). In certain embodiments, each treatment site is irradiated by an apparatus in contact with the scalp or skull or not in contact with the scalp or skull as described herein. In certain such embodiments, the irradiated portion of the scalp is blanched during the irradiation, is not blanched during the irradiation, is cooled during the irradiation, or is not cooled during the irradiation.

In certain embodiments, the patient's scalp is prepared for treatment prior to irradiation. For example, in certain embodiments, preparing the patient's scalp for treatment comprises removing at least a portion of the hair or substantially all the hair from the predetermined areas of the patient's scalp to be irradiated. Removing the hair (e.g., by shaving so that the irradiated portion of the scalp is substantially free of hair) advantageously reduces heating of the patient's scalp by hair which absorbs the light from the light emitting apparatus. In certain other embodiments, the hair is not shaved or otherwise removed prior to irradiation. For example, irradiating the patient's scalp can be performed using pulsed light with wavelengths, temporal pulse widths, and duty cycles which avoid adverse heating of the patient's scalp due to absorption of light by the hair.

In certain embodiments, the parameters of the pulsed light beam used to irradiate the patient's scalp or skull are selected to perform one or more of the following: (i) to cause increased neuron survival of the brain cells following at least one physical trauma, (ii) to support one or more intercellular or intracellular biological processes involved in the survival or regeneration of brain cells, or (iii) to modulate membrane potentials in order to enhance, restore, or promote cell survival, cell function, or both of the irradiated brain cells following a traumatic brain injury. In one example such embodiment, the pulsed light beam at the emission surface of the apparatus has a beam diameter in a range between 10 millimeters and 40 millimeters, an average irradiance per pulse in a range between 10 mW/cm$^2$ and 10 W/cm$^2$, one or more wavelengths in a range between 780 nanometers and 840 nanometers, and a temporal pulsewidth in a range between 0.1 millisecond and 150 seconds or between 0.1 millisecond and 300 milliseconds. The duty cycle of certain embodiments can be in a range between 10% and 30%. Other ranges of these parameters of the pulsed light beam can be selected in accordance with various other embodiments described herein.

Neurologic Function Scales

Neurologic function scales can be used to quantify or otherwise characterize the efficacy of various embodiments described herein. Neurologic function scales generally use a number of levels or points, each point corresponding to an aspect of the patient's condition. The number of points for a patient can be used to quantify the patient's condition, and improvements in the patient's condition can be expressed by changes of the number of points. One example neurologic function scale is the National Institute of Health Stroke Scale (NIHSS) which can be used for short-term measurements of efficacy (e.g., at 24 hours). The NIHSS is a comprehensive and objective scale which utilizes a seven-minute physical exam, a 13 item scale, and 42 points. Zero points corresponds to a normal exam, 42 points (the maximum) corresponds to basically comatose, and over 15-20 points indicates that the effects of the stroke are particularly severe. The NIHSS has previously been used for tPA trials in the treatment of ischemic stroke, with a 4-point change over 24 hours and an overall score of 0 or 1 at three months indicative of a favorable outcome. Other neurologic function scales include, but are not limited to, modified Rankin Scale (mRS), Barthel Index (BI), Glasgow Outcome, Glasgow Coma Scale, Canadian Neurologic Scale, and stroke impact scales such as SIS-3 and SIS-16. In some scales, an improvement in the patient's condition is indicated by a reduction in the number of points. For example, the mRS has six points total, with zero corresponding to normal functioning, and six corresponding to death. In other scales, an improvement in the patient's condition is indicated by an increase in the number of points. For example, in the Glasgow Outcome which has five points, zero corresponds to death and five corresponds to full recovery. In certain embodiments, two or more of the neurologic function scales can be used in combination with one another, and can provide longer-term measurements of efficacy (e.g., at three months).

For stroke, the U.S. Food and Drug Administration (FDA) and the neurologic community have expressed interest in clinical patient outcomes at 90 days post stroke. Two of the most common and accepted instruments for measuring efficacy are the NIHSS and mRS. The FDA is flexible in the way that neurologic function scales can be used. For example, it is acceptable to use the mRS (i) in dichotomized fashion with success at score of 0-1 or (ii) it can be analyzed looking at shifts in the scale showing improvement of patients along the five-point scale.

In certain embodiments described herein, a patient exhibiting symptoms of an ischemic stroke is treated by irradiating a plurality of treatment sites on the patient's scalp. The irradiation is performed utilizing irradiation parameters (e.g., wavelength, irradiance, time period of irradiation, etc.) which, when applied to members of a treated group of patients, produce at least a 2% average difference between the treated group and a placebo group on at least one neurologic function scale analyzed in dichotomized or any other fashion and selected from the group consisting of: NIHSS, mRS, BI, Glasgow Outcome, Glasgow Coma Scale, Canadian Neurologic Scale, SIS-3, and SIS-16. Certain other embodiments produce at least a 4% average difference, at least a 6% average difference, or at least a 10% average difference between treated and placebo groups on at least one of the neurologic function scales analyzed in dichotomized or any other fashion and selected from the group consisting of: NIHSS, mRS, BI, Glasgow Outcome, Glasgow Coma Scale, Canadian Neurologic Scale, SIS-3, and SIS-16. In certain embodiments, the irradiation of the patient's scalp produces a change in the patient's condition. In certain such embodiments, the change in the patient's condition corresponds to a change in the number of points indicative of the patient's condition. In certain such embodiments, the irradiation produces a change of one point, a change of two points, a change of three points, or a change of more than three points on a neurologic function scale.

Various studies have been conducted to provide information regarding the interaction of laser light with the human body and the effectiveness and safety of transcranial light therapy (TLT). For example, (i) power density measurements have been made to determine the transmission of laser light having a wavelength of approximately 808 nanometers through successive layers of human brain tissue; (ii) in vivo thermal measurements have been made to determine the heating effect in living tissue of laser light having a wavelength of approximately 808 nanometers; (iii) NEST-1 and NEST-2 phototherapy trials ("*Infrared laser therapy for ischemic stroke: a new treatment strategy: Results of the NeuroThera Effectiveness and Safety Trial-1 (NEST-1),*" *Stroke*, 2007; 38:1843-1849, incorporated in its entirety by reference herein, and "*Effectiveness and safety of transcranial laser therapy for acute ischemic stroke,*" *Stroke*, 2009: 40:1359-1364, which is incorporated in its entirety by reference herein), suggest the safety and efficacy of transcranial light therapy (TLT) for treatment of humans with ischemic stroke; (iv) examination of continuous wave (CW) and pulse wave (PW) NILT delivery frequency settings to determine optimally efficacious treatment regimens using the RSCEM (see, P. A. Lapchak, L. De Taboada, "*Transcranial near infrared laser treatment (NILT) increases cortical adenosine-5'-triphosphate (ATP) content following embolic strokes in rabbits,*" *Brain Research*, Vol. 1306, pp. 100-105 (2010), which is incorporated in its entirety by reference herein; (v) study of low-level laser therapy (LLLT) for TBI using the mouse closed-head injury (CHI) model by studying the neurobehavioral and histological outcome of the traumatized mice (see, A. Oron et al., "*Low-Level Laser Therapy Applied Transcranially to Mice following Traumatic Brain Injury Significantly Reduces Long-Term Neurological Deficits,*" *Journal of Neurotrauma*, Volume 24, Number 4, 2007 which is incorporated in its entirety by reference herein); and (vi) study of infrared Transcranial Laser Therapy (TLT) for efficacy in an amyloid precursor peptide (APP) transgenic mouse model of Alzheimer's Disease (AD). These various studies are described more fully in U.S. Pat. Appl. Publ. No. US 2009/0254154 A1, which is incorporated in its entirety by reference herein.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method of treating a brain of a patient, the method comprising:

noninvasively irradiating a first area of at least 1 $cm^2$ of a head of the patient with light having an irradiance between 100 $\mu W/cm^2$ to 10 $W/cm^2$ and a wavelength between 630 nanometers to 1064 nanometers during a first time period to irradiate a first area of a target subsurface tissue of the brain of the patient below a dura of the patient;

noninvasively irradiating a second area of at least 1 $cm^2$ of the head of the patient with light having an irradiance between 100 $\mu W/cm^2$ to 10 $W/cm^2$ and a wavelength between 630 nanometers to 1064 nanometers during a second time period to irradiate a second area of the target subsurface tissue of the brain of the patient below the dura of the patient, the second area of the target subsurface tissue of the brain of the patient partially overlapping the first area of the target subsurface tissue of the brain of the patient; and identifying the first area of the head of the patient and the second area of the head of the patient by placing a template over the head of the patient, wherein the template comprises a first indicator of the first area of the head of the patient and a second indicator of the second area of the head of the patient, wherein the first area of the head of the patient and the second area of the head of the patient do not overlap one another, and wherein the first time period and the second time period do not overlap one another.

2. The method of claim 1, wherein the first indicator comprises a first opening in the template and the second indicator comprises a second opening in the template.

3. The method of claim 1, further comprising placing a light source at a first position to noninvasively irradiate the first area of the head of the patient and moving the light source to a second position to noninvasively irradiate the second area of the head of the patient.

4. The method of claim 1, further comprising increasing a transmissivity of the first area of the head of the patient and increasing a transmissivity of the second area of the head of the patient.

5. The method of claim 4, wherein increasing the transmissivity of the first area of the head of the patient comprises applying pressure to the first area of the head of the patient to at least partially blanch the first area of the head of the patient.

6. The method of claim 4, wherein increasing the transmissivity of the first area of the head of the patient comprises removing hair from the first area of the head of the patient prior to noninvasively irradiating the first area of the head of the patient.

7. The method of claim 4, wherein increasing the transmissivity of the first area of the head of the patient comprises applying an index-matching material to the first area of the head of the patient.

8. The method of claim 1, wherein the first area of the head of the patient and the second area of the head of the patient are spaced from one another by at least 10 millimeters.

9. The method of claim 1, wherein the patient has suffered an ischemic stroke or a traumatic brain injury.

10. The method of claim 1, wherein the light has a duty cycle between 1% to 80%.

11. The method of claim 10, wherein the light has a peak irradiance between 12.5 $mW/cm^2$ to 1000 $W/cm^2$.

12. The method of claim 10, wherein the light has a time-averaged irradiance between 10 $mW/cm^2$ to 10 $W/cm^2$.

13. The method of claim 10, wherein the light has a temporal pulsewidth between 0.001 millisecond to 150 seconds.

14. The method of claim 10, wherein the light has a time-averaged irradiance between 0.01 $mW/cm^2$ to 1 $W/cm^2$.

15. The method of claim 1, wherein no portion of the head of the patient is heated to a temperature greater than 60 degrees Celsius.

16. The method of claim 1, wherein no portion of the brain of the patient is heated to a temperature greater than 5 degrees Celsius above its baseline temperature.

17. The method of claim 1, wherein the light is laser light.

18. A method of treating a brain of a patient, the method comprising:

noninvasively irradiating a first area of at least 1 cm$^2$ of a head of the patient with light having an irradiance between 100 μW/cm$^2$ to 10 W/cm$^2$ and a wavelength between 630 nanometers to 1064 nanometers during a first time period to irradiate a first area of a target subsurface tissue of the brain of the patient below a dura of the patient; and noninvasively irradiating a second area of at least 1 cm$^2$ of the head of the patient with light having an irradiance between 100 μW/cm$^2$ to 10 W/cm$^2$ and a wavelength between 630 nanometers to 1064 nanometers during a second time period to irradiate a second area of the target subsurface tissue of the brain of the patient below the dura of the patient, the second area of the target subsurface tissue of the brain of the patient partially overlapping the first area of the target subsurface tissue of the brain of the patient, wherein the first area of the head of the patient and the second area of the head of the patient do not overlap one another, wherein the first time period and the second time period do not overlap one another, and wherein the first area of the head of the patient is over a first hemisphere of the brain of the patient, and the second area of the head of the patient is over a second hemisphere of the brain of the patient.

19. The method of claim 18, further comprising identifying the first area of the head of the patient and the second area of the head of the patient by placing a template over the head of the patient, wherein the template comprises a first indicator of the first area of the head of the patient and a second indicator of the second area of the head of the patient, wherein the first indicator comprises a first opening in the template and the second indicator comprises a second opening in the template.

20. The method of claim 18, further comprising placing a light source at a first position to noninvasively irradiate the first area of the head of the patient and moving the light source to a second position to noninvasively irradiate the second area of the head of the patient.

21. The method of claim 18, further comprising increasing a transmissivity of the first area of the head of the patient and increasing a transmissivity of the second area of the head of the patient.

22. The method of claim 21, wherein increasing the transmissivity of the first area of the head of the patient comprises applying pressure to the first area of the head of the patient to at least partially blanch the first area of the head of the patient.

23. The method of claim 21, wherein increasing the transmissivity of the first area of the head of the patient comprises removing hair from the first area of the head of the patient prior to noninvasively irradiating the first area of the head of the patient.

24. The method of claim 21, wherein increasing the transmissivity of the first area of the head of the patient comprises applying an index-matching material to the first area of the head of the patient.

25. The method of claim 18, wherein the first area of the head of the patient and the second area of the head of the patient are spaced from one another by at least 10 millimeters.

26. The method of claim 18, wherein the patient has suffered an ischemic stroke or a traumatic brain injury.

27. The method of claim 18, wherein the light has a duty cycle between 1% to 80%.

28. The method of claim 27, wherein the light has a peak irradiance between 12.5 mW/cm$^2$ to 1000 W/cm$^2$.

29. The method of claim 27, wherein the light has a time-averaged irradiance between 10 mW/cm$^2$ to 10 W/cm$^2$.

30. The method of claim 27, wherein the light has a temporal pulsewidth between 0.001 millisecond to 150 seconds.

31. The method of claim 27, wherein the light has a time-averaged irradiance between 0.01 mW/cm$^2$ to 1 W/cm$^2$.

32. The method of claim 27, wherein the light is laser light.

33. The method of claim 18, wherein no portion of the head of the patient is heated to a temperature greater than 60 degrees Celsius.

34. The method of claim 18, wherein no portion of the brain of the patient is heated to a temperature greater than 5 degrees Celsius above its baseline temperature.

* * * * *